United States Patent
Bontchev et al.

(10) Patent No.: US 10,023,503 B2
(45) Date of Patent: Jul. 17, 2018

(54) BIOCHARS AND BIOCHAR TREATMENT PROCESSES

(71) Applicant: Cool Planet Energy Systems, Inc., Greenwood Village, CO (US)

(72) Inventors: Ranko Panayotov Bontchev, Samarillo, CA (US); Han Suk Kim, Thousand Oaks, CA (US); Richard Wilson Belcher, Ventura, CA (US); Mark L. Jarand, Newbury Park, CA (US)

(73) Assignee: Cool Planet Energy Systems, Inc., Greenwood Village, CO (US)

( * ) Notice: Subject to any disclaimer, the term of this patent is extended or adjusted under 35 U.S.C. 154(b) by 0 days.

(21) Appl. No.: 15/213,122

(22) Filed: Jul. 18, 2016

(65) Prior Publication Data

US 2016/0326067 A1     Nov. 10, 2016

Related U.S. Application Data

(60) Division of application No. 14/873,053, filed on Oct. 1, 2015, which is a continuation-in-part of application
(Continued)

(51) Int. Cl.
| | |
|---|---|
| *C01B 32/05* | (2017.01) |
| *C05F 11/00* | (2006.01) |
| *C05F 11/02* | (2006.01) |
| *C10B 53/02* | (2006.01) |
| *C10B 57/02* | (2006.01) |

(Continued)

(52) U.S. Cl.
CPC .............. *C05F 11/00* (2013.01); *C05F 11/02* (2013.01); *C05G 3/00* (2013.01); *C05G 3/0047* (2013.01); *C09K 17/02* (2013.01); *C10B 53/02* (2013.01); *C10B 57/02* (2013.01); *C01B 32/05* (2017.08);
(Continued)

(58) Field of Classification Search
CPC ...................................................... C01B 31/02
See application file for complete search history.

(56) References Cited

U.S. PATENT DOCUMENTS

| | | |
|---|---|---|
| 1,369,428 A | 2/1921 | Hawley |
| 3,841,974 A | 10/1974 | Osborne |

(Continued)

FOREIGN PATENT DOCUMENTS

| | | |
|---|---|---|
| CN | 1997590 A | 7/2007 |
| CN | 103053244 A | 4/2013 |

(Continued)

OTHER PUBLICATIONS

Ahmad, et al., "Biochar as a Sorbent for Contaminant Management in Soil and Water: A Review," Chemosphere, vol. 99, pp. 19-33 (Nov. 27, 2013).

(Continued)

*Primary Examiner* — Wayne Langel
(74) *Attorney, Agent, or Firm* — Avyno Law P.C.

(57) ABSTRACT

Treated biochar and methods for treating biochar are provided. The method for treating the biochar includes forcing, assisting or accelerating the movement of an infiltrant into the pores of the biochar, whereby the treatment affects properties of the biochar that provide for a more reliable and predictable biochar for use in various applications, including, but not limited to, agricultural applications.

17 Claims, 29 Drawing Sheets

Related U.S. Application Data

No. 14/385,986, filed as application No. PCT/US2012/039862 on May 29, 2012, which is a continuation of application No. 13/154,213, filed on Jun. 6, 2011, now Pat. No. 8,317,891.

(51) Int. Cl.
  *C05G 3/00* (2006.01)
  *C09K 17/02* (2006.01)
  *C09K 17/04* (2006.01)

(52) U.S. Cl.
  CPC .............. C09K 17/04 (2013.01); Y02E 50/14 (2013.01); Y02P 20/145 (2015.11); Y10S 71/903 (2013.01)

(56) References Cited

U.S. PATENT DOCUMENTS

| | | | |
|---|---|---|---|
| 4,153,514 A | 5/1979 | Garrett et al. |
| 4,268,275 A | 5/1981 | Chittick |
| 4,383,391 A | 5/1983 | Thomas et al. |
| 4,421,524 A | 12/1983 | Chittick |
| 4,487,958 A | 12/1984 | Ream et al. |
| 4,495,165 A | 1/1985 | Gurza |
| 4,497,637 A | 2/1985 | Purdy et al. |
| 4,501,644 A | 2/1985 | Thomas |
| 4,530,702 A | 7/1985 | Fetters et al. |
| 4,618,735 A | 10/1986 | Bridle et al. |
| 4,861,351 A | 8/1989 | Nicholas et al. |
| 4,992,480 A | 2/1991 | Mahajan et al. |
| 5,015,423 A | 5/1991 | Eguchi et al. |
| 5,032,618 A | 7/1991 | Marchionna et al. |
| 5,087,786 A | 2/1992 | Nubel et al. |
| 5,204,102 A | 4/1993 | Coles et al. |
| 5,221,290 A | 6/1993 | Dell |
| 5,462,908 A | 10/1995 | Liang et al. |
| 5,504,259 A | 4/1996 | Diebold et al. |
| 5,508,060 A | 4/1996 | Perman et al. |
| 5,756,194 A | 5/1998 | Shogren et al. |
| 5,820,640 A | 10/1998 | Ikura et al. |
| 5,857,807 A | 1/1999 | Longo, Sr. |
| 5,863,467 A | 1/1999 | Mariner et al. |
| 6,133,328 A | 10/2000 | Lightner |
| 6,227,473 B1 | 5/2001 | Arnold |
| 6,228,806 B1 | 5/2001 | Mehta |
| 6,339,031 B1 | 1/2002 | Tan |
| 6,548,026 B1 | 4/2003 | Dales et al. |
| 6,747,067 B2 | 6/2004 | Melnichuk et al. |
| 6,811,703 B2 | 11/2004 | Elliott |
| 6,841,085 B2 | 1/2005 | Werpy et al. |
| 6,923,838 B2 | 8/2005 | Maubert et al. |
| 6,994,827 B2 | 2/2006 | Safir et al. |
| 7,033,972 B2 | 4/2006 | Shikada et al. |
| 7,226,566 B2 | 6/2007 | Beierle |
| 7,282,189 B2 | 10/2007 | Zauderer |
| 7,458,999 B2 | 12/2008 | Schenck |
| 7,846,979 B2 | 12/2010 | Rojey et al. |
| 7,888,540 B2 | 2/2011 | Deluga et al. |
| 7,947,155 B1 | 5/2011 | Green et al. |
| 8,173,044 B1 | 5/2012 | Cheiky et al. |
| 8,197,573 B2 | 6/2012 | Scharf |
| 8,236,085 B1 | 8/2012 | Cheiky et al. |
| 8,317,891 B1 | 11/2012 | Cheiky et al. |
| 8,317,892 B1 | 11/2012 | Cheiky et al. |
| 8,318,997 B2 | 11/2012 | McAlister |
| 8,361,186 B1 | 1/2013 | Shearer et al. |
| 8,430,937 B2 | 4/2013 | Cheiky et al. |
| 8,431,757 B2 | 4/2013 | Cheiky et al. |
| 8,568,493 B2 | 10/2013 | Cheiky et al. |
| 8,747,797 B2 | 6/2014 | Shearer et al. |
| 9,260,666 B2 | 2/2016 | Aelion et al. |
| 9,478,324 B1 | 10/2016 | Favetta et al. |
| 9,493,379 B2 | 11/2016 | Cheiky et al. |
| 2002/0012725 A1 | 1/2002 | Carlson |
| 2003/0119552 A1 | 6/2003 | Laumen et al. |
| 2004/0111968 A1 | 6/2004 | Day et al. |
| 2004/0128909 A1 | 7/2004 | Smiley |
| 2006/0225345 A1 | 10/2006 | Westrate |
| 2007/0123420 A1 | 5/2007 | Hayashi et al. |
| 2007/0172408 A1* | 7/2007 | Takagi .................. C04B 14/022 423/445 R |
| 2008/0006519 A1 | 1/2008 | Badger |
| 2008/0016769 A1 | 1/2008 | Pearson |
| 2008/0093209 A1 | 4/2008 | Noto |
| 2008/0216391 A1 | 9/2008 | Cortright et al. |
| 2008/0223269 A1 | 9/2008 | Paoluccio |
| 2008/0300435 A1 | 12/2008 | Cortright et al. |
| 2008/0317657 A1 | 12/2008 | Hall et al. |
| 2008/0317907 A1 | 12/2008 | Thomas et al. |
| 2009/0007484 A1 | 1/2009 | Smith |
| 2009/0081292 A1 | 3/2009 | Otomo et al. |
| 2009/0126433 A1 | 5/2009 | Piskorz et al. |
| 2009/0139139 A1 | 6/2009 | Tilman et al. |
| 2009/0151251 A1 | 6/2009 | Manzer et al. |
| 2009/0183430 A1 | 7/2009 | Schubert et al. |
| 2009/0217575 A1 | 9/2009 | Raman et al. |
| 2009/0217584 A1 | 9/2009 | Raman et al. |
| 2009/0253947 A1 | 10/2009 | Brandvold et al. |
| 2009/0308787 A1 | 12/2009 | O'Connor et al. |
| 2010/0040510 A1 | 2/2010 | Randhava et al. |
| 2010/0162780 A1* | 7/2010 | Scharf ........................ C05B 7/00 71/36 |
| 2010/0180805 A1 | 7/2010 | Cheiky |
| 2010/0218417 A1 | 9/2010 | Bauldreay et al. |
| 2010/0223839 A1 | 9/2010 | Garcia-Perez et al. |
| 2010/0236309 A1 | 9/2010 | Celia |
| 2010/0236987 A1 | 9/2010 | Kreis |
| 2010/0240900 A1* | 9/2010 | Zhang .................... B82Y 30/00 546/330 |
| 2010/0257775 A1 | 10/2010 | Cheiky |
| 2010/0270505 A1 | 10/2010 | Gallaspy et al. |
| 2010/0300866 A1 | 12/2010 | van Aardt et al. |
| 2010/0310447 A1 | 12/2010 | Yaniv et al. |
| 2010/0311157 A1 | 12/2010 | Van Alstyne et al. |
| 2011/0003693 A1 | 1/2011 | Spittle |
| 2011/0023566 A1 | 2/2011 | Lodwig et al. |
| 2011/0081336 A1 | 4/2011 | Medoff |
| 2011/0092726 A1 | 4/2011 | Clarke |
| 2011/0100359 A1 | 5/2011 | North |
| 2011/0172092 A1 | 7/2011 | Lee et al. |
| 2011/0177466 A1 | 7/2011 | Cheiky |
| 2011/0209386 A1 | 9/2011 | Cheiky et al. |
| 2011/0212004 A1 | 9/2011 | Cheiky et al. |
| 2011/0258912 A1 | 10/2011 | O'connor et al. |
| 2012/0103040 A1 | 5/2012 | Wolf et al. |
| 2012/0125064 A1 | 5/2012 | Joseph et al. |
| 2012/0208254 A1 | 8/2012 | Smith et al. |
| 2012/0220454 A1 | 8/2012 | Chen et al. |
| 2012/0237994 A1 | 9/2012 | Das et al. |
| 2012/0283493 A1 | 11/2012 | Olson et al. |
| 2012/0286209 A1 | 11/2012 | Cheiky et al. |
| 2012/0304718 A1 | 12/2012 | Cheiky et al. |
| 2012/0304719 A1 | 12/2012 | Cheiky et al. |
| 2013/0025188 A1 | 1/2013 | Cheiky et al. |
| 2013/0025190 A1 | 1/2013 | Cheiky et al. |
| 2013/0123103 A1 | 5/2013 | Anderson et al. |
| 2013/0213101 A1 | 8/2013 | Shearer et al. |
| 2014/0016709 A1 | 1/2014 | Ko et al. |
| 2014/0024528 A1 | 1/2014 | Smith et al. |
| 2014/0037536 A1 | 2/2014 | Reimerink-Schats et al. |
| 2014/0118884 A1* | 5/2014 | Lin ........................ C04B 35/14 361/502 |
| 2014/0161709 A1 | 6/2014 | Karthikeyan |
| 2014/0177136 A1 | 6/2014 | Kim et al. |
| 2014/0345341 A1 | 11/2014 | Fiato et al. |
| 2014/0345343 A1 | 11/2014 | Wilson et al. |
| 2014/0349847 A1 | 11/2014 | Schrader |
| 2014/0352378 A1 | 12/2014 | Shearer et al. |
| 2015/0101372 A1 | 4/2015 | Cheiky et al. |
| 2015/0128672 A1 | 5/2015 | Shearer et al. |
| 2015/0157661 A1 | 6/2015 | Eddy et al. |
| 2015/0361369 A1 | 12/2015 | Tait et al. |
| 2016/0023959 A1 | 1/2016 | Bontchev et al. |

(56) References Cited

U.S. PATENT DOCUMENTS

| | | | |
|---|---|---|---|
| 2016/0102024 A1 | 4/2016 | Schrader et al. | |
| 2016/0362607 A1 | 12/2016 | Weaver et al. | |
| 2016/0368831 A1 | 12/2016 | Bontchev et al. | |
| 2017/0187041 A1* | 6/2017 | Yamada | H01M 4/587 |

FOREIGN PATENT DOCUMENTS

| | | |
|---|---|---|
| EP | 01140811 A2 | 5/1985 |
| GB | 2479469 A | 10/2011 |
| KR | 100819505 B1 | 4/2008 |
| WO | 8204223 A1 | 12/1982 |
| WO | 2004037747 A2 | 5/2004 |
| WO | 2009004652 A1 | 1/2009 |
| WO | 2010084230 A1 | 7/2010 |
| WO | 2010129988 A1 | 11/2010 |
| WO | 2011006717 A2 | 1/2011 |
| WO | 2011014916 A1 | 2/2011 |
| WO | 2011097183 A2 | 8/2011 |
| WO | 2011143380 A2 | 11/2011 |
| WO | 2011143718 A1 | 11/2011 |
| WO | 2012094736 A1 | 7/2012 |
| WO | 2014091279 A1 | 6/2014 |
| WO | 2014146205 A1 | 9/2014 |
| WO | 2016054431 A1 | 4/2016 |
| WO | 2016187161 A1 | 11/2016 |

OTHER PUBLICATIONS

Berek, et al., "Improving Soil Productivity with Biochar," ICGAI, Yogyakarta, Indonesia, 23 pgs. (Nov. 11-14, 2013).
Beesley, et al., "A review of Biochars? Potential Role in the Remediation, Revegetation and Restoration of Contaminated Soils," Environmental Pollution 159, pp, 3269-3282 (Jul. 23, 2011).
Biliaderis, et al., "Functional Food Carbohydrates," CRC Press 2006, Ch. 16, pp. 517-518.
Bucheli, et al., "Polycyclic Aromatic Hydrocarbons and Polychlorinated Aromatic Compounds in Biochar," Biochar for Environmental Management, Ch. 21, pp. 595-622 (Jan. 2015).
Buerschaper, R., "Thermal & Electrical Conductivity of Graphite & Carbon at Low Temperatures," Jour. of App. Physics, pp. 452-454 (1944).
Cheng, et al., "Stability of Black Carbon in Soils Across a Climatic Gradient," Jour. of Geophysical Research Biogeosciences, vol. 113, G02027, pp. 1-10 (2008).
Chew, T.L. and Bhatia, S., "Catalytic Processes Towards the Production of Biofuels in a Palm Oil and Oil Palm Biomass-based Biorefinery," Bioresource Tech., vol. 99, pp. 7911-8922 (2008).
Demirbas, A., "Effects of Temperature & Particle Size on Bio-Char Yield from Pyrolysis of Agricultural Residues," J. Anal. Pyrolysis, vol. 72, pp. 243-248 (2004).
Downie: Biochar Production and Use: Environmental Risks and Rewards: PhD Thesis: The University of New South Wales; Sydney, Australia, p. 1-16, p. 155-168 (2011).
Elliott, D.C. and Neuenschwander, G.G., "Liquid Fuels by Low-Severity Hydrotreating of Biocrude," Dev. in Thermochemical Biomass Conversion, vol. 1, pp. 611-621 (1996).
Extended European Search Report issued by the European Patent Office for European Patent Application No. 12797129.9 dated Mar. 6, 2015 (7 pgs.).
Extended European Search Report issued by the European Patent Office for European Patent Application No. 12817137.8 dated Jul. 13, 2015 (8 pgs.).
Faludi, J., "World Changing Change Your Thinking a Carbon-Negative Fuel," Oct. 16, 2007; www.worldchanging.com (9 pgs.).
Gehrer, r. And Hayek, K., "A Fully Programmable System for the Study of Catalytic Gas Reactions," J. Physe. E: Sci. Instrum., vol. 18, pp. 836-838 (1985).
Gray, et al., "Water Update in Biochars: The Roles of Porosity and Hydrophobicity; Biomass and Bioenergy," vol. 6, No. 1, pp, 196-205 (Jan. 23, 2014).
Greenfacts, "Facts on Health and the Environment," Dioxins, Apr. 13, 2017, 3 pp.; retrieved from https://www.greenfacts.org/en/d on Aug. 15, 2004.
Hadjittofi, et al., "Activated Biochar Derived from Cactus Fibres—Preparation, Characterization and Application on CU(II) Removal from Aqueous Solutions," Bioresource Technology, vol. 159, pp. 460-464 (May 2014).
Hua, et al., "impacts Upon Soil Quality and Plant Growth of Bamboo Charcoal Addition to Composted Sludge," Environmental Technology, vol. 33, No. 1, pp. 61-68 (Jan. 18, 2012).
Innovation Fluides Supercritiques, Explore, Use, Make the Most of Supercritical Fluids, Nov. 27, 2015. Online, retrieved from the Internet on Mar. 6, 2017; <http://web/archive.org/web/20151127045828/http://www.supercriticalfluid.org/supercritical-fluids.146.0>html; 2 pp.
Jindo, et al., "Biochar Influences the Microbial Community Structure During Manure Composting with Agricultural Wastes," Science of the Total Environment, vol. 416, pp. 476-481 (Feb. 2012).
Karmakar, et al., "Plant Defence Activators Inducing Systematic Resistance in Zingiber Officinale Rosc. Against Pythium Aphanidermatum (Edson) Fitz.," Indian Journal of Biotechnology, vol. 2, pp. 591-595 (2003).
Kim, et al., "Characteristics of Crosslinked Potato Starch & Starch-Filled Linear Low-Density Polyethylene Films," Carbohydrate Polymers, vol. 50, pp. 331-337 (2002).
Kolton, et al., "Impact of Biochar Application to Soil on the R oot-Associated Bacterial Community Structure of Fully Developed Greenhouse Pepper Plants," Appl. Env. Micro., pp. 4924-4930, Abstract (Jul. 2011).
Laird, D., "The Charcoal Vision: A Win Win Scenario," Agron, J., vol. 100, No. 1, pp. 178-181 (2008).
Lashari, et al,, "Effect of Amendment of Biochar-manure Compost in Conjunction with Pyroligneous Solution on Soil Quality and Wheat Yield of a salt-stressed Cropland from Central China Great Plain," Field Crops Research, vol. 144, pp. 113-118 (Mar. 20, 2013).
Lehmann, J., "Nutrient Avail. & Leaching in an Archaeological Anthrosol & Ferraisol of the Central Amazon Basin: Fertilizer, Manure and Charcoal Amendments," Plant Soil, vol. 249, pp. 343-357 (2003).
Lima, et al., "Physiochemical and Adsorption Properties of Fast-Pyrolysis Bio-Chars and their Steam Activated Counterparts," J.Chem. Tech. Biotechnical, vol. 85, pp. 1515-1521 (2010).
Liu, et al., "An Experimental Study of Rheological Properties and Stability Characteristics of Biochar-Glycerol-Water Slurry Fuels," Fuel Processing Technology, vol. 153, Issue 1, pp. 37-42 (Aug. 5, 2016).
Mathews, J.A., "Carbon-negative Biofuels", Energy Policy, vol. 36, pp. 940-945 (2008).
McHenry, Mark P., "Agricultural Bio-char Production, Renewable Energy Generation and Farm Carbon Sequestration in Western Australia: Certainty, Uncertainty, and Risk," Agriculture, Ecosystems and Environments, vol. 129, pp. 1-7 (2009).
Mohan, et al., "Pyrolysis of Wood/Biomass for Bio-Oil: A Critical Review," Energy & Fuels, vol. 20, pp. 848-889 (2006).
Norman, et al.; "Best Management Practices for Reclaiming Surface Mines in Washington and Oregon," Open-File Report 0-92-2, revised ed. Dec. 1997: www.oregongeology.org Feb. 9, 2010 (128 pgs.).
Oh, et al., "Ulitization of Biochar Impregnated with Anaerobically Digested Slurry as Slow-Release Fertilizer," Journal of Plant Nutrition and Soil Science, vol. 177, Issue 1, pp. 97-103 (Feb. 2014).
Omata, et al., "Optimization of Cu Oxide Catalyst for Methanol Synthesis under High CO2 Partial Pressure Using Combinatorial Tools," App. Catalyst A: General, vol. 262, pp. 207-214 (2004).
Preston, C.M. and Schmidt, M.W., "Black (Pyrogenic) Carbon; a Synthesis of Current Knowledge & Uncertainties w/ Special Consideration of Boreal Regions," Biogeosciences, vol. 3, pp. 397-420 (2006).
Rosenberg, et al., "More on Commercial Carbon Resistors as Low Pressure Gauges," Intl. Jour of Impat. Eng., vol. 34, pp. 732-742 (2007).
Schmidt, et al., "Biochar and Biochar-compost as Soil Amendments to a Vineyard Soil: Influence on Plant Growth, Nutrient Update,

(56) References Cited

OTHER PUBLICATIONS

Plant Health and Grape Equality," Agriculture, Ecosystems and Environment, vol. 191, Issue 15, pp. 117-123 (Jun. 2014).
Sharma, R.K. and Bakhshi, N.N., "Catalytic Upgrading of Pyrolysis Oil," Energy & Fuels, vol. 7, pp. 306-314 (1993).
Shivaram, et al., "Flow and Yield Behavior of Ultrafine Mallee Biochar Slurry Fuels: The Effect of Particle Size Distributon and Additives," 10th Japan/China Symposium on Coal and C1 Chemistry, vol. 104, pp, 326-332 (Feb. 2013).
Sorrenti, G. (Doctoral Thesis): "Biochar in Perennial Crops: Nutritional, Agronomical and Environmental Implications," University of Bologna, Abstract, Chs. 4, 5, 7, p. 101 Table 4.2 (Mar. 1, 2015).
Takeishi, K., "Dimethy Ether & Catalyst Development for Production of Syngas," Biofuels, vol. 1(1), pp. 217-226 (2010).
Tryon, E.H.; "Effect of Charcoal on Certain Physical, Chemical, & Biological Properties of Forest Soils," Ecological Monographs, vol. 18, No. 1, pp. 81-115 (Jan. 1948).
Xusheng, et al., "Implications of Production and Agricultural Utilization of Biochar and its International Dynamic," Transactions of the CSAE, vol. 27, No. 2, 7 pgs. (2011) with English Abstract.
Wikipedia; Bacillus Thuringiensis; Dec. 27, 2015; online, retrieved from the Internet on Mar. 6, 2017; <https://en/wikipedia.org/w/index.php?title=bacillus+thuringlensis&oldid=696970111>: 6 pp.
Supplemental European Search Report dated Aug. 17, 2017 for EP 14875314.8.
EPO; Supplementary European Search Report; dated May 17, 2018; 8 pps.

\* cited by examiner

Greater nutrient retention in the 1 ton/acre
and 3 tons/acre biochar amended soils
than in the controls

BIOCHARS AND BIOCHAR TREATMENT PROCESSES

CROSS-REFERENCE TO RELATED APPLICATIONS

This application is a divisional of and claims priority of U.S. patent application Ser. No. 14/873,053 filed Oct. 1, 2015, titled Biochars and Biochar Treatment Processes, U.S. Provisional Application Ser. No. 62/058,445, titled Methods, Materials and Applications for Controlled Porosity and Release Structures and Applications, which was filed on Oct. 1, 2014 and U.S. Provisional Application Ser. No. 62/058,472, titled High Additive Retention Biochars, Methods and Application, which was filed on Oct. 1, 2014 and which is a continuation-in-part of U.S. patent application Ser. No. 14/385,986, filed on May 29, 2012, which is a 371 filing of international application PCT/US12/39862, which claims priority to U.S. patent application Ser. No. 13/154,213, filed on Jun. 6, 2011, now U.S. Pat. No. 8,317,891, all of the above of which are incorporated into this application by reference in their entirety.

FIELD OF INVENTION

The invention relates to porous carbonaceous structures, materials and compositions having a variety of varied and complex pores, pore properties, and pore morphologies, as well as, methods to treat, process and affect the properties of those structures, materials and compositions. In particular, certain implementations of the present inventions relate to treated biochars having increased capabilities to retain additives for use in applications, including, but not limited to, agriculture applications.

BACKGROUND

Many types of materials have pores and porous morphologies. Such materials can be inorganic, organic-inorganic, and organic, and combinations and variations of these. Recently, much attention has been directed toward controlling the properties of these materials through affecting the nature of their porous structures, including, among other things, the nature of the pore surfaces. In spite of these efforts, the solutions that have been developed are largely limited in scope and applicable only to a specific or narrow type of material.

For example, much attention has been focused on the use of porous carbonaceous materials, such as biochars, in conjunction with controlling and regulating the growth of plants and vegetation, e.g., crops. Although such uses of biochar have generally been known for a considerable amount of time, their commercial and widespread adoption has not occurred. It is believed there are several reasons for these failures.

Porous carbonaceous materials, and in particular biochar, come from many varied and different sources. As a result, biochars have very inconsistent and unpredictable properties. These inconsistencies and lack of predictability make their use difficult and in many cases problematic. Jeffery et al. in *Agriculture, Ecosystems, and Environment* (2011) ("Jeffery") recently compiled the results from several biochar field trials from around the globe. The trials show at best a modest improvement with biochar applications and the application rates required to achieve these modest results is significant. (See Jeffery, at page 175 and FIG. 1) In Lehmann, et al, *Biochar for Environmental Management* (2006) ("Lehmann") Lehmann, a pioneer researcher, is quoted about biochar, " . . . but variability is high and it is not yet clear under what soil and climatic conditions high or low yields can be expected." (Lehmann, Chp. 12, at page 207) It is believed that these inconsistencies and lackluster outcomes are common among biochar work. It is indicative that one ordinarily skilled in the art does not produce a biochar with predictable properties and outcomes. Thus, the use of these materials, e.g., biochar, can have limited, sporadic or little to no beneficial effect and may be problematic and detrimental, e.g., lower crop yield, and in some situations death of the crops.

Similarly, these porous carbonaceous materials, e.g., biochar, can be made by many varied and different processes and conditions for those processes, which in turn result in materials that have very inconsistent and again unpredictable properties. These processes and processing related inconsistencies are in addition to, and typically compound, the problems arising from the material's source. Because of these inconsistencies and unpredictabilities, the substantial potential and anticipated benefits from using biochar and other carbonaceous porous materials, has not been realized. As a result, biochar has at most been a scientific curiosity, not found wide spread use, not found large scale commercial applications, and at most been relegated to small niche applications. Thus, prior to the present inventions, it is believed that methods and systems to produce a biochar for applications with predictable, controllable, and beneficial results had not been obtained.

In general, the art has focused on the failings, and problems, of biochars by attempting to refine the process to make the biochar, or the selection of starting material from which a particular biochar is made. Typically, these attempts were done with the hope that increased process control, material selection and refinements would overcome the unpredictabilities, inconsistencies, and harmful effects found with existing biochars. It is believed that these attempts have been to a lesser or greater extent failures. It is believed that to date, and prior to the present inventions, there has not existed a widely available biochar having predictable properties; nor, prior to the present inventions, has there existed a process for making such biochars.

The present inventions go against the teachings and direction of the art. Rather than focus on the manner in which a particular biochar is made, or selecting a particular starting material for a biochar, embodiments of the present inventions directly address the long-standing and unsolved problems with biochars' lack of consistency and predictability.

SUMMARY

The present invention relates to treated biochar and methods and systems for treating the biochar. The present invention teaches treating the biochar in a manner that forces, accelerates or assists the infusion of liquid solutions into the pores of the biochar, thereby allowing for at least part of the surface of the pores of the biochar to be washed, cleaned and to have physical properties (such as usable pore volume) or chemical properties (such as pH) adjusted. It optionally allows for the impregnation or inoculation of the pores of the biochar with additives, which can be beneficial for the intended use of the biochar or can be effective in further adjusting the physical and/or chemical properties of the biochar.

In one example of an implementation of the present invention, the method for treating the biochar includes placing porous carbonaceous materials in a tank or chamber; adding a washing liquid to the tank; and changing the pressure in the tank by, for example, placing the contents of the tank under a partial vacuum. In this example, the washing liquid may be added to the tank either before the pressure change is applied or while the pressure change is being applied. The washing liquid may be water, may be an acid for adjusting the pH of the surface of the pores or may include other additives. Thereafter, the moisture content of the biochar may be adjusted to remove excess liquids and/or to dry the biochar, as desired. The biochar may also be subject to further treatment, for example, inoculating the pores with an additive. The pores of the biochar may be impregnated with an additive in the same manner as the pores were washed with the washing liquid or by using a surfactant solution as further described below. Through the above treatment method, at least 10% and, in certain implementation, 50% or more of the pore volume of the pores of the porous carbonaceous material may be filled with the washing liquid and/or the additive.

In another example of an implementation of the present invention, the method for treating the biochar includes placing the porous carbonaceous material in a tank; adding a surfactant solution to the tank; and mixing the surfactant with the porous carbonaceous material. In one example, the surfactant solution is a liquid solution containing 0.1-20% surfactant, which may, for example, be a *yucca* extract. The liquid solution may further include an additive. As in the previous example, the moisture content of the biochar may be adjusted to remove excess liquids and/or to dry the biochar, as desired. The biochar may then be subject to further treatment, for example, inoculating the pores with an additive. The pores of the biochar may be impregnated with an additive by using a surfactant or a vacuum to force the infusion of the additive into the pores. Through the above treatment method at least 10% or more of the pore volume of the pores of the porous carbonaceous material may be filled with solution. In certain implementations, 50% or more of the pore volume of the pores of the porous carbonaceous material may be filled with solution.

As explained further below, treatment, in accordance with the present invention, can (i) repurpose problematic biochars, (ii) handle changing biochar material sources, e.g., seasonal and regional changes in the source of biomass, (iii) provide for custom features and functions of biochar for particular soils, regions or agricultural purposes; (iv) increase the retention properties of biochar, (v) provide for large volumes of biochar having desired and predictable properties, (vi) provide for biochar having custom properties; (vii) handle differences in biochar caused by variations in pyrolysis conditions or manufacturing of the "raw" biochar; and (viii) address the majority, if not all, of the problems that have, prior to the present invention, stifled the large scale adoption and use of biochars.

Other devices, apparatus, systems, methods, features and advantages of the invention are or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE FIGURES

The invention may be better understood by referring to the following figures. The components in the figures are not necessarily to scale, emphasis instead being placed upon illustrating the principles of the invention.

DESCRIPTION OF THE INVENTION

Figure 1:
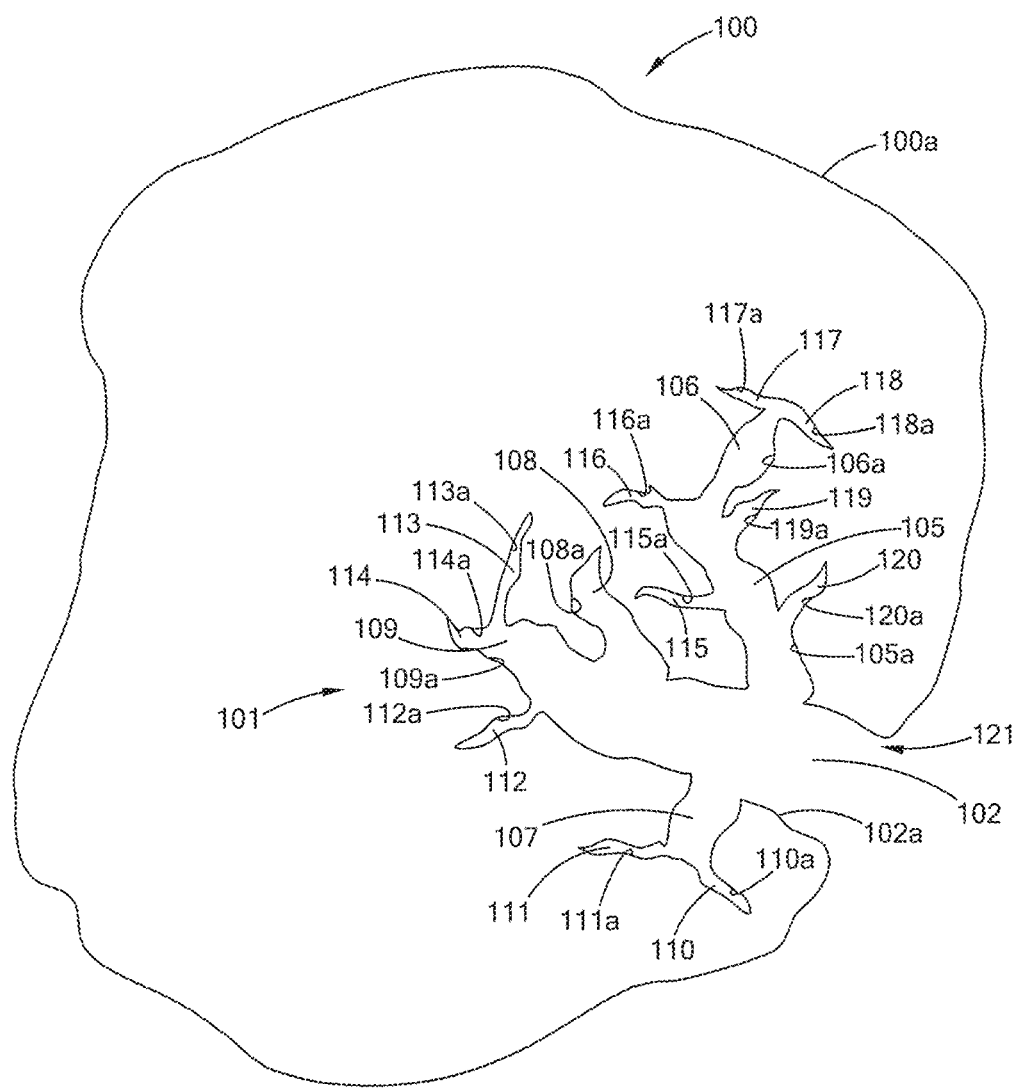
FIG. 1 illustrates a cross-section of one example of a raw biochar particle.

As illustrated in the attached figures, the present invention relates to treated biochar and methods for treating biochar having varied and complex pores, pore properties, and pore morphologies. The treatment processes of the present invention are able to affect the properties of the biochar structures creating biochar having enhanced abilities to retain additives useful for an end application. Generally, for agricultural applications, such enhanced abilities could include holding water, and nutrients, e.g. fertilizer. Further, these treated biochars may have the ability to take up and hold materials from a location or process, which materials need to be removed and may be undesirable, such as heavy metals or other contaminants.

For example, through treatment, the properties of the raw biochar can be modified to significantly increase the biochar's ability to retain water and/or nutrients while also, in many cases, creating an environment beneficial to microorganisms and providing structure to the soil to allow for pockets of air necessary for efficient root operation. In addition to nutrients, other material additives, e.g., herbicide, pesticide, can be utilized and benefit from the increased holding and retention capacities of the treated biochar. The processing of the biochar can also ensure that the pH of biochar used in the present application is suitable for creating soil conditions beneficial for plant growth, which has been a challenge for raw biochars.

Generally, treated biochar of the present invention can be used throughout the world, in numerous soil types, agricultural applications, horticultural, large and small scale farming, organic farming, and in a variety of soil management applications and systems, and combinations and variations of these. Examples of these applications include for example, use in acidic and highly weathered tropical field soils, use in temperate soils of higher fertility, use in large commercial applications, use for the production of large scale crops such as, soybean, corn, sugarcane and rice, in forestry applications, for golf courses (e.g., greens, fairways), for general purpose turf grasses, wine grapes, table grapes, raisin grapes, fruit and nut trees, ground fruits (e.g., strawberries, blueberries, blackberries), row crops (e.g., tomatoes, celery, lettuce, leafy greens), root crops (e.g., tubers, potatoes, beets, carrots), mushrooms, and combinations and variations of these and other agricultural applications. As discussed in more detail below, biochar treated in this way may also be used in other applications, such as animal feed, composting, water treatment, and heavy metal remediation, to name a few.

For purposes of this application, the term "biochar" shall be given its broadest possible meaning and shall include any solid carbonaceous materials obtained from the pyrolysis, torrefaction, gasification or any other thermal and/or chemical conversion of a biomass. For purposes of this application, the solid carbonaceous material may include, but not be limited to, BMF char disclosed and taught by U.S. Pat. No. 8,317,891, which is incorporated into this application by reference. Pyrolysis is generally defined as a thermochemical decomposition of organic material at elevated temperatures in the absence of, or with reduced levels of oxygen. When the biochar is referred to as "treated" or undergoes "treatment," it shall mean raw biochar that has undergone additional physical, biological, and/or chemical processing.

As used herein, unless specified otherwise, the terms "carbonaceous", "carbon based", "carbon containing", and similar such terms are to be given their broadest possible meaning, and would include materials containing carbon in various states, crystallinities, forms and compounds.

As used herein, unless stated otherwise, room temperature is 25° C. And, standard temperature and pressure is 25° C. and 1 atmosphere. Unless stated otherwise, generally, the term "about" is meant to encompass a variance or range of ±10%, the experimental or instrument error associated with obtaining the stated value, and preferably the larger of these.

A. Biochars

Typically, biochars include porous carbonaceous materials, such as charcoal, that are used as soil amendments or other suitable applications. Biochar most commonly is created by pyrolysis of a biomass. In addition to the benefits to plant growth, yield and quality, etc.; biochar provides the benefit of reducing carbon dioxide ($CO2CO_2$) in the atmosphere by serving as a method of carbon sequestration. Thus, biochar has the potential to help mitigate climate change, via carbon sequestration. However, to accomplish this important, yet ancillary benefit, to any meaningful extent, the use of biochar in agricultural applications must become widely accepted, e.g., ubiquitous. Unfortunately, because of the prior failings in the biochar arts, this has not occurred. It is believed that with the solutions of the present invention may this level of use of biochar be achieved; and more importantly, yet heretofore unobtainable, realize the benefit of significant carbon dioxide sequestration.

In general, one advantage of putting biochar in soil includes long term carbon sequestration. It is theorized that as worldwide carbon dioxide emissions continue to mount, benefits may be obtained by, controlling, mitigating and reducing the amount of carbon dioxide in the atmosphere and the oceans. It is further theorized that increased carbon dioxide emissions are associated with the increasing industrial development of developing nations, and are also associated with the increase in the world's population. In addition to requiring more energy, the increasing world population will require more food. Thus, rising carbon dioxide emissions can be viewed as linked to the increasing use of natural resources by an ever increasing global population. As some suggest, this larger population brings with it further demands on food production requirements. Biochar uniquely addresses both of these issues by providing an effective carbon sink, e.g., carbon sequestration agent, as well as, an agent for improving and increasing agricultural output. In particular, biochar is unique in its ability to increase agricultural production, without increasing carbon dioxide emission, and preferably reducing the amount of carbon dioxide in the atmosphere. However, as discussed above, this unique ability of biochar has not been realized, or seen, because of the inherent problems and failings of prior biochars including, for example, high pH, phytotoxicity due to high metals content and/or residual organics, and dramatic product inconsistencies.

Biochar can be made from basically any source of carbon, for example, from hydrocarbons (e.g., petroleum based materials, coal, lignite, peat) and from a biomass (e.g., woods, hardwoods, softwoods, waste paper, coconut shell, manure, chaff, food waste, etc.). Combinations and variations of these starting materials, and various and different members of each group of starting materials can be, and are, used. Thus, having the large number of vastly different starting materials, each of which potentially leads to a biochar having different properties, begins to frame the substantial nature of one of the problems that the present inventions address and solve.

Many different pyrolysis or carbonization processes can be, and are used, to create biochars. In general, these processes involve heating the starting material under positive pressure, reduced pressure, vacuum, inert atmosphere, or flowing inert atmosphere, through one or more heating cycles where the temperature of the material is generally brought above about 400° C., and can range from about 300° C. to about 900° C. The percentage of residual carbon formed and several other initial properties are strong functions of the temperature and time history of the heating cycles. In general, the faster the heating rate and the higher the final temperature the lower the char yield. Conversely, in general, the slower the heating rate or the lower the final temperature the greater the char yield. The higher final temperatures also lead to modifying the char properties by changing the inorganic mineral matter compositions, which in turn, modify the char properties. Ramp, or heating rates, hold times, cooling profiles, pressures, flow rates, and type of atmosphere can all be controlled, and typically are different from one biochar supplier to the next. These differences potentially lead to a biochar having different properties, further framing the substantial nature of one of the problems that the present inventions address and solve. Generally, in carbonization most of the non-carbon elements, hydrogen and oxygen are first removed in gaseous form by the pyrolytic decomposition of the starting materials, e.g., the biomass. The free carbon atoms group or arrange into crystallographic formations known as elementary graphite crystallites. Typically, at this point the mutual arrangement of the crystallite is irregular, so that free interstices exist between them. Thus, pyrolysis involves thermal decomposition of carbonaceous material, e.g., the biomass, eliminating non-carbon species, and producing a fixed carbon structure.

As noted above, raw or untreated biochar is generally produced by subjecting biomass to either a uniform or varying pyrolysis temperature (e.g., 300° C. to 550° C. to 750° C. or more) for a prescribed period of time in a reduced oxygen environment. This process may either occur quickly, with high reactor temperature and short residence times, slowly with lower reactor temperatures and longer residence times, or anywhere in between. The biomass from which the char is obtained may minimize debris, such as bark, leaves and small branches. The biomass may further include feedstock to help adjust the pH and particle size distribution in the resulting raw biochar. In some applications, it is desirous to have biomass that is fresh, less than six months old, and with an ash content of less than 3%. Further, by using biochar derived from different biomass, e.g., pine, oak, hickory, birch and coconut shells from different regions, and understanding the starting properties of the raw biochar, the treatment methods can be tailored to ultimately yield a treated biochar with predetermined, predictable physical and chemical properties.

In general, biochar particles can have sizes ranging from less than ¾ to less than ½ of an inch. By way of example, the biochar particles can have particle sizes as shown or measured in Table 1 below. When referring to a batch having ¾ inch particles ¾, the batch would have particles that will pass through a 3 mesh sieve, but will not pass through (i.e., are caught by or sit atop) a 4 mesh sieve.

TABLE 1

| U.S. Mesh (i.e., mesh) | Inches | Microns (μm) | Millimeters (mm) |
|---|---|---|---|
| 3 | 0.2650 | 6730 | 6.370 |
| 4 | 0.1870 | 4760 | 4.760 |
| 5 | 0.1570 | 4000 | 4.000 |
| 6 | 0.1320 | 3360 | 3.360 |
| 7 | 0.1110 | 2830 | 2.830 |
| 8 | 0.0937 | 2380 | 2.380 |
| 10 | 0.0787 | 2000 | 2.000 |
| 12 | 0.0661 | 1680 | 1.680 |
| 14 | 0.0555 | 1410 | 1.410 |
| 16 | 0.0469 | 1190 | 1.190 |
| 18 | 0.0394 | 1000 | 1.000 |
| 20 | 0.0331 | 841 | 0.841 |
| 25 | 0.0280 | 707 | 0.707 |
| 30 | 0.0232 | 595 | 0.595 |
| 35 | 0.0197 | 500 | 0.500 |
| 40 | 0.0165 | 400 | 0.400 |
| 45 | 0.0138 | 354 | 0.354 |
| 50 | 0.0117 | 297 | 0.297 |
| 60 | 0.0098 | 250 | 0.250 |
| 70 | 0.0083 | 210 | 0.210 |
| 80 | 0.0070 | 177 | 0.177 |
| 100 | 0.0059 | 149 | 0.149 |
| 120 | 0.0049 | 125 | 0.125 |
| 140 | 0.0041 | 105 | 0.105 |
| 170 | 0.0035 | 88 | 0.088 |
| 200 | 0.0029 | 74 | 0.074 |
| 230 | 0.0024 | 63 | 0.063 |
| 270 | 0.0021 | 53 | 0.053 |
| 325 | 0.0017 | 44 | 0.044 |
| 400 | 0.0015 | 37 | 0.037 |

For most applications, it is desirable to use biochar particles having particle sizes from about ¾ mesh to about 60/70 mesh, about ⅘ mesh to about 20/25 mesh, or about ⅘ mesh to about 30/35 mesh. It being understood that the desired mesh size, and mesh size distribution can vary depending upon a particular application for which the biochar is intended.

FIG. 1 illustrates a cross-section of one example of a raw biochar particle. As illustrated in FIG. 1, a biochar particle 100 is a porous structure that has an outer surface 100a and a pore structure 101 is formed within the biochar particle 100. As used herein, unless specified otherwise, the terms "porosity", "porous", "porous structure", and "porous morphology" and similar such terms are to be given their broadest possible meaning, and would include materials having open pores, open and closed pores, and combinations of these, and would also include macropores, mesopores, and micropores and combinations, variations and continuums of these morphologies. Unless specified otherwise, the term "pore volume" is the total volume occupied by the pores in a particle or collection of particles; the term "inter-particle void volume" is the volume that exists between a collection of particle; the term "solid volume or volume of solid means" is the volume occupied by the solid material and does not include any free volume that may be associated with the pore or inter-particle void volumes; and the term "bulk volume" is the apparent volume of the material including the particle volume, the inter-particle void volume, and the internal pore volume.

The pore structure 101 forms an opening 121 in the outer surface 100a of the biochar particle 100. The pore structure 101 has a macropore 102, which has a macropore surface 102a, and which surface 102a has an area, i.e., the macropore surface area. (In this diagram only a single micropore is shown. If multiple micropores are present than the sum of their surface areas would equal the total macropore surface area for the biochar particle.) From the macropore 102, several mesopores 105, 106, 107, 108 and 109 are present, each having its respective surfaces 105a, 106a, 107a, 108a and 109a. Thus, each mesopore has its respective surface area; and the sum of all mesopore surface areas would be the total mesopore surface area for the particle. From the mesopores, e.g., 107, there are several micropores 110, 111, 112, 113, 114, 115, 116, 117, 118, 119 and 120, each having its respective surfaces 110a, 111a, 112a, 113a, 114a, 115a, 116a, 117a, 118a, 119a and 120a. Thus, each micropore has its respective surface area and the sum of all micropore surface areas would be the total micropore surface area for the particle. The sum of the macropore surface area, the mesopore surface area and the micropore surface area would be the total pore surface area for the particle.

Macropores are typically defined as pores having a diameter greater than 300 nm, mesopores are typically defined as diameter from about 1-300 nm, and micropores are typically defined as diameter of less than about 1 nm, and combinations, variations and continuums of these morphologies. The macropores each have a macropore volume, and the sum of these volumes would be the total macropore volume. The mesopores each have a mesopore volume, and the sum of these volumes would be the total mesopore volume. The micropores each have a micropore volume, and the sum of these volumes would be the total micropore volume. The sum of the macropore volume, the mesopore volume and the micropore volume would be the total pore volume for the particle.

Additionally, the total pore surface area, volume, mesopore volume, etc., for a batch of biochar would be the actual, estimated, and preferably calculated sum of all of the individual properties for each biochar particle in the batch.

It should be understood that the pore morphology in a biochar particle may have several of the pore structures shown, it may have mesopores opening to the particle surface, it may have micropores opening to particle surface, it may have micropores opening to macropore surfaces, or other combinations or variations of interrelationship and structure between the pores. It should further be understood that the pore morphology may be a continuum, where moving inwardly along the pore from the surface of the particle, the pore transitions, e.g., its diameter becomes smaller, from a macropore, to a mesopore, to a micropore, e.g., macropore 102 to mesopore 109 to micropore 114.

In general, the biochars have porosities that can range from 0.2 $cm^3/cm^3$ to about 0.8 $cm^3/cm^3$ and more preferably about 0.2 $cm^3/cm^3$ to about 0.5 $cm^3/cm^3$. (Unless stated otherwise, porosity is provided as the ratio of the total pore volumes (the sum of the micro+ meso+ macro pore volumes) to the solid volume of the biochar. Porosity of the biochar particles can be determined, or measured, by measuring the micro-, meso-, and macro pore volumes, the bulk volume, and the inter particle volumes to determine the solid volume by difference. The porosity is then calculated from the total pore volume and the solid volume.

Figure 2:
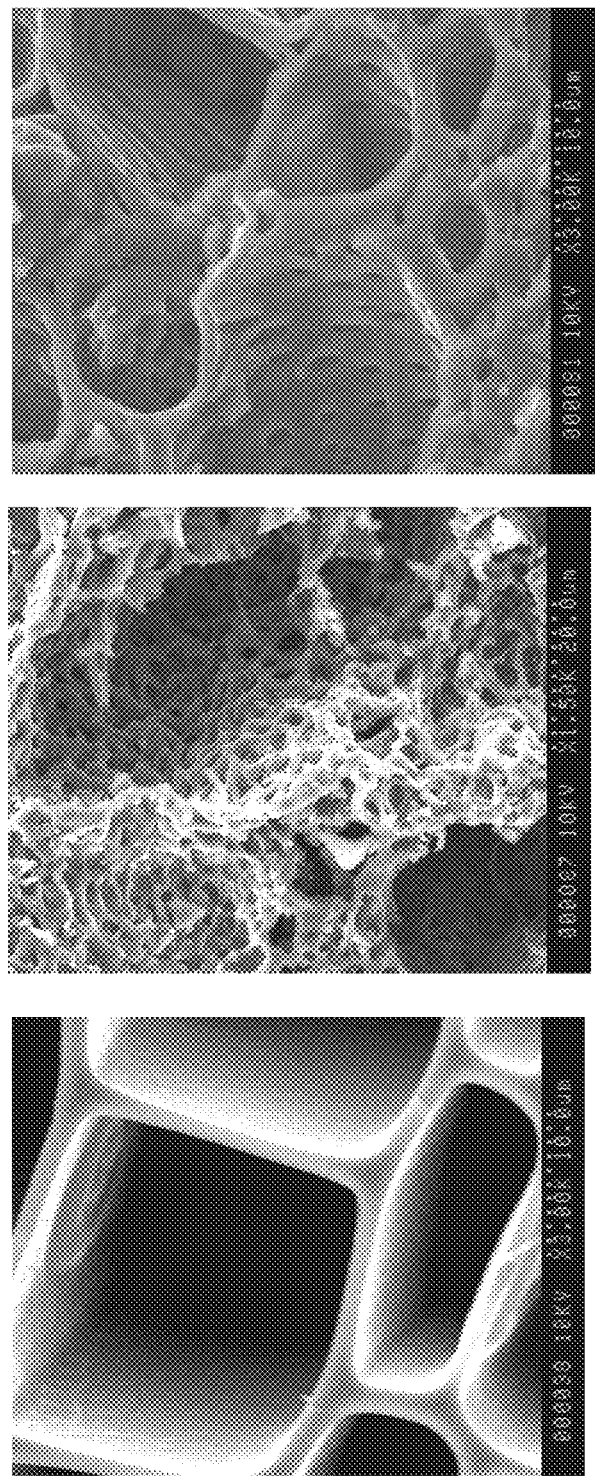
FIG. 2*a* is a SEM (10 KV×3.00K 10.0 μm) of a pore morphology of treated biochar made from pine.
FIG. 2*b* is a SEM (10 KV×3.00K 10.0 μm) of a pore morphology of treated biochar made from birch.
FIG. 2*c* is a SEM (10 KV×3.00K 10.0 μm) of a pore morphology of treated biochar made from coconut shells.

As noted above, the use of different biomass potentially leads to biochars having different properties, including, but not limited to different pore structures. By way of example, FIGS. 2A, 2B and 2C illustrate Scanning Electron Microscope ("SEM") images of various types of treated biochars showing the different nature of their pore morphology. FIG. 2A is biochar derived from pine. FIG. 2B is biochar derived from birch. FIG. 2C is biochar derived from coconut shells.

The surface area and pore volume for each type of pore, e.g., macro-, meso- and micro- can be determined by direct measurement using CO2 adsorption for micro-, N2 adsorption for meso- and macro pores and standard analytical surface area analyzers and methods, for example, particle analyzers such as Micrometrics instruments for meso- and micro pores and impregnation capacity for macro pore volume. Mercury porosimetry, which measures the macroporosity by applying pressure to a sample immersed in mercury at a pressure calibrated for the minimum pore diameter to be measured, may also be used to measure pore volume.

Figure 3:
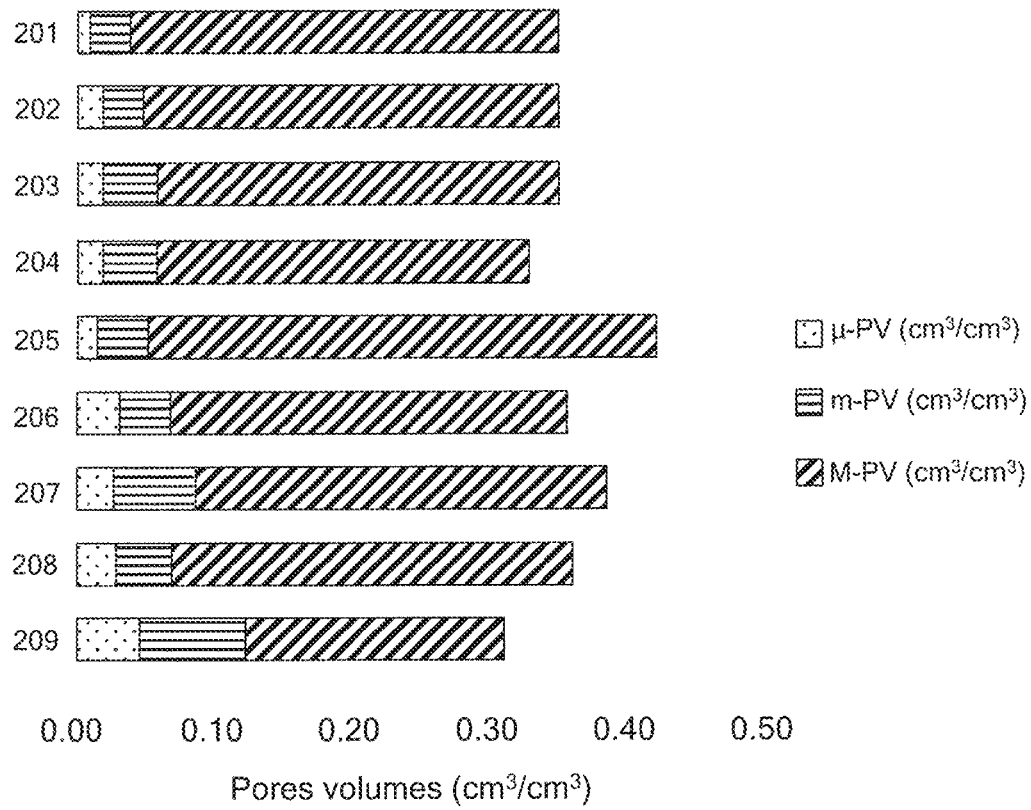
FIG. 3 is a chart showing porosity distribution of various biochars.

The total micropore volume can be from about 2% to about 25% of the total pore volume. The total mesopore volume can be from about 4% to about 35% of the total pore volume. The total macropore volume can be from about 40% to about 95% of the total pore volume. By way of example, FIG. 3 shows a bar chart setting out examples of the pore volumes for sample biochars made from peach pits 201, juniper wood 202, a first hard wood 203, a second hard wood 204, fir and pine waste wood 205, a first pine 206, a second pine 207, birch 208 and coconut shells 209.

As explained further below, treatment can increase usable pore volumes, which leads to increased retention properties and promotes further performance characteristics of the biochar. Knowing the properties of the starting raw biochar, one can treat the biochar to produce controlled, predictable and optimal resulting physical and chemical properties.

B. Treatment

Testing has demonstrated that if the biochar is then treated, at least partially, in a manner that causes the forced infusion and/or diffusion of liquids into and/or out of the biochar pores (through mechanical, physical, or chemical means), certain beneficial properties of the biochar can be altered or improved through treatment over and above simply contacting these liquids with the biochar. By knowing the properties of the raw biochar and the optimal desired properties of the treated biochar, the raw biochar can then be treated in a manner that results in the treated biochar having controlled optimized properties and greater levels of consistency between batches as well as between treated biochars arising from various feedstocks.

The basis for treating biochar is that given the large pore volume of biochars, the physical and chemical properties of biochars can be altered, mitigated or enhanced by altering pore surface properties. In particular, effective treatment processes can mitigate or remove deleterious pore surface properties and modify anywhere from between 10% to 99% or more of pore surface area of a biochar particle. By modifying the pore surfaces through treatment, the treated biochars exhibit a greater capacity to retain water and/or other nutrients while at the same time providing structure to the soil to allow for pockets of air necessary for efficient root operation. Through the use of treated biochars, agricultural applications can realize increased moisture control, increased nutrient retention, reduced water usages, reduced water requirements, reduced runoff, reduced nutrient needs, reduced nutrient usage, increased yields, increased yields with lower water requirements and/or nutrient requirements, and any combination and variation of these and other benefits.

Treatment further allows the biochar to be modified to possess certain known properties that enhance the benefits received from the use of biochar. While the selection of raw biochar and/or pyrolysis conditions under which the biochar was manufactured can make treatment processes less cumbersome, more efficient and further controlled, treatment processes can be utilized that provide for the biochar to have desired and generally sustainable resulting properties regardless of the biochar source or pyrolysis conditions. As explained further below, treatment can (i) repurpose problematic biochars, (ii) handle changing biochar material sources, e.g., seasonal and regional changes in the source of biomass, (iii) provide for custom features and functions of biochar for particular soils, regions or agricultural purposes; (iv) increase the retention properties of biochar, (v) provide for large volumes of biochar having desired and predictable properties, (vi) provide for biochar having custom properties, (vii) handle differences in biochar caused by variations in pyrolysis conditions or manufacturing of the "raw" biochar; and (viii) address the majority, if not all, of the problems that have, prior to the present invention, stifled the large scale adoption and use of biochars.

Treatment can wash both the interior and exterior pore surfaces, remove harmful chemicals and properties, and alter certain properties of the biochar and the pore surfaces. This is in stark contrast to simple washing which generally only impacts the exterior surfaces and a small percentage of the interior surface area. Treatment can further be used to coat substantially all, or all of the biochar pore surfaces with a surface modifying agent or impregnate the pores with additives or treatment to provide a predetermined feature to the biochar, e.g., surface charge and charge density, surface species and distribution, targeted nutrient addition, magnetic modifications, root growth facilitator, and water absorptivity and water retention properties.

Figure 4:
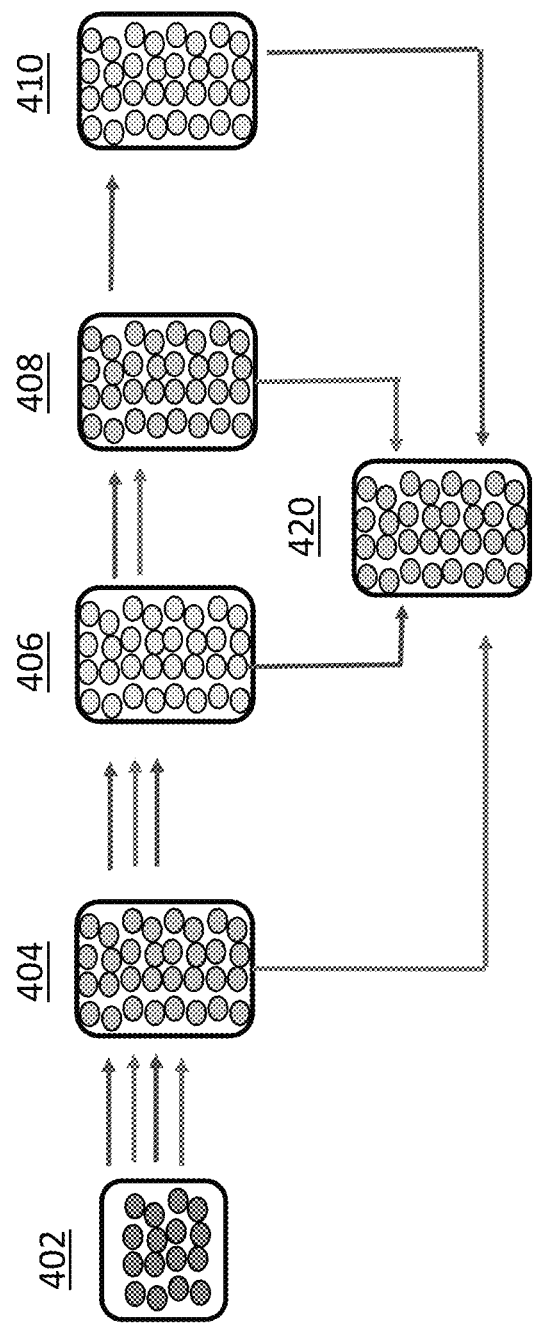
FIG. 4 is a flow chart process diagram of one implementation of a process for treating the raw biochar in accordance with the invention.

FIG. 4 is a schematic flow diagram of one example treatment process 400 for use in accordance with the present invention. As illustrated, the treatment process 400 starts with raw biochar 402 that may be subjected to one or more reactors or treatment processes prior to bagging 420 the treated biochar for resale. For example, 404 represents reactor 1, which may be used to wash the biochar. The wash may be a simple water wash or may be an acid wash used for the purpose of altering the pH of the raw biochar particles 402. The wash may also contain a surfactant or detergent to aid the penetration of the wash solution into the pores of the biochar. The wash may optionally be heated or may be used at ambient temperature or less. For some applications, depending upon the properties of the raw biochar, a water and/or acid/alkaline wash 404 (the latter for pH adjustment) may be the only necessary treatment prior to bagging the biochar 420. If, however, the moisture content of the biochar needs to be adjusted, the washed biochar may then be put into a second reactor 406 for purposes of reducing the moisture content in the washed biochar. From there, the washed and moisture adjusted biochar may be bagged 420.

Again, depending upon the starting characteristics of the raw biochar and the intended application for the resale product, further processing may still be needed or desired. In this case, the washed moisture adjusted biochar may then be passed to a third reactor 408 for inoculation, which may include the impregnation of biochar with beneficial bacteria, microbes, fertilizers or other additives. Thereafter, the inoculated biochar may be bagged 420, or may be yet further processed, for example, in a fourth reactor 410 to have further moisture removed from or added to the biochar. Further moisture adjustment may be accomplished by placing the inoculated biochar in a fourth moisture adjustment reactor 410 or circulating the biochar back to a previous moisture adjustment reactor (e.g. reactor 406). Those skilled in the art will recognize that the ordering in which the raw biochar is processed and certain processes may be left out, depending on the properties of the starting raw biochar and the desired application for the biochar. For example, the wash and inoculation processes may be performed without the moisture adjustment step, inoculation processes may also be performed with or without any washing, pH adjustment or any moisture adjustment. All the processes may be completed alone or in the conjunction with one or more of the others.

Figure 4A:
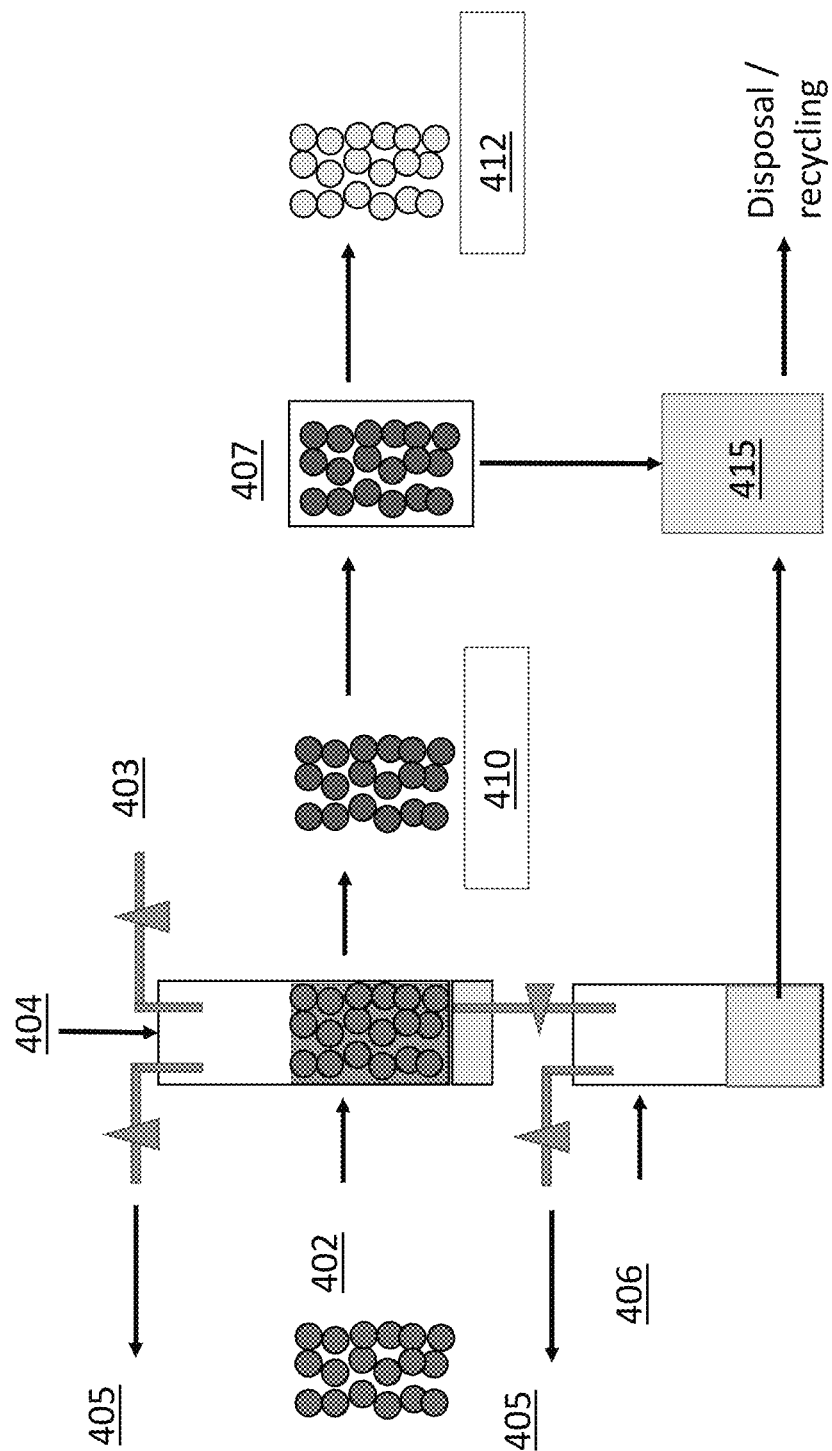
FIG. 4*a* illustrates a schematic of one example of an implementation of a biochar treat processes that that includes washing, pH adjustment and moisture adjustment.
Figure 4B:
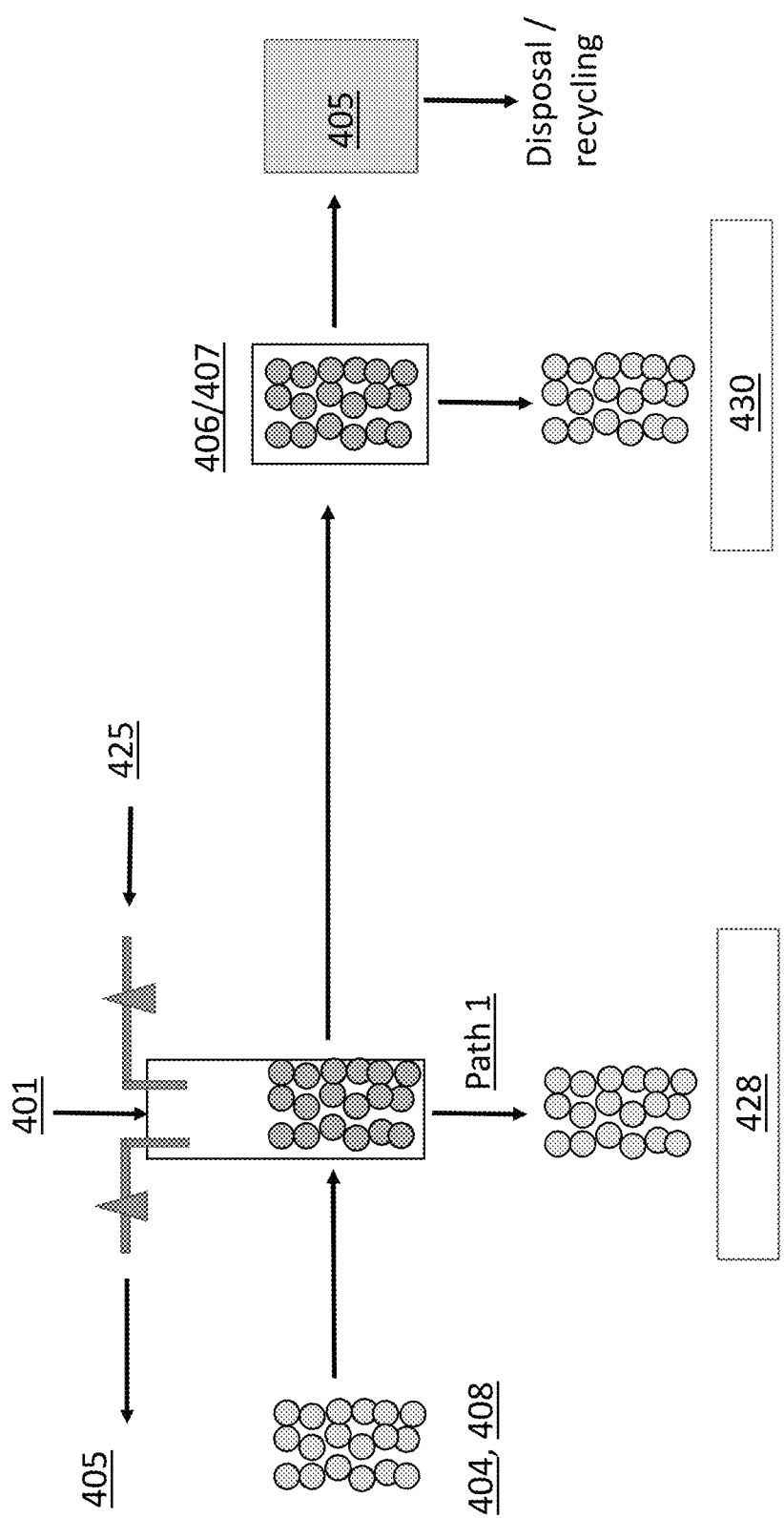
FIG. 4*b* illustrates yet another example of an implementation of a biochar treatment processing that includes inoculation.

For example, FIG. 4a illustrates a schematic of one example of an implementation of biochar processing that includes washing and both pH and moisture adjustment. FIG. 4b illustrates yet another example of an implementation of biochar processing that includes inoculation.

As illustrated in FIG. 4a, raw biochar 402 is placed into a reactor or tank 404. A washing or treatment liquid 403 is then added to a tank and a partial vacuum, using a vacuum pump, 405 is pulled on the tank. The treating or washing liquid 403 may be used to clean or wash the pores of the biochar 402 or adjust the pH level of the surface, or both, among other things. The vacuum can be pulled after the treatment liquid 403 is added or while the treatment liquid 403 is added. Thereafter, the washed/pH adjusted biochar 410 may be moisture adjusted by vacuum exfiltration 406 to pull the extra liquid from the washed/moisture adjusted biochar 410 or may be placed in a centrifuge 407, heated or subjected to pressure gradient changes (e.g., blowing air) for moisture adjustment. The moisture adjusted biochar 412 may then be bagged or subject to further treatment. Any excess liquids 415 collected from the moisture adjustment step may be disposed of or recycled, as desired. Optionally, biochar fines may be collected from the excess liquids 415 for further processing, for example, to create a slurry, cakes, or biochar extrudates.

Optionally, rather than using a vacuum pump 405, a positive pressure pump may be used to apply positive pressure to the tank 404. In some situations, applying positive pressure to the tank may also function to force or accelerate the washing or treating liquid 403 into the pores of the biochar 402. Any change in pressure in the tank 404 or across the surface of the biochar could facilitate the exchange of gas and/or moisture into and out of the pores of the biochar with the washing or treating liquid 403 in the tank. Accordingly, changing the pressure in the tank and across the surface of the biochar, whether positive or negative, is within the scope of this invention.

As illustrated FIG. 4b, the washed/pH adjusted biochar 410 or the washed/pH adjusted and moisture adjusted biochar 412 may be further treated by inoculating or impregnating the pores of the biochar with an additive 425. The biochar 410, 412 placed back in a reactor 401, an additive solution 425 is placed in the reactor 401 and a vacuum, using a vacuum pump, 405 is pulled on the tank. Again, the vacuum can be pulled after the additive solution 425 is added to the tank or while the additive solution 425 is being added to the tank. Thereafter, the washed, pH adjusted and inoculated biochar 428 can be bagged. Alternatively, if further moisture adjustment is required, the biochar can be further moisture adjusted by vacuum filtration 406 to pull the extra liquid from the washed/moisture adjusted biochar 410 or may be placed in a centrifuge 407 for moisture adjustment. The resulting biochar 430 can then be bagged. Any excess liquids 415 collected from the moisture adjustment step may be disposed of or recycled, as desired. Optionally, biochar fines may be collected from the excess liquids 415 for further processing, for example, to create a slurry or biochar extrudates. As described above, both processes of the FIGS. 4a and 4b can be performed with a surfactant solution in place of, or in conjunction with, the vacuum 405.

While known processes exist for the above described processes, research associated with the present invention has shown improvement and the ability to better control the properties and characteristics of the biochar if the processes are performed through the infusion and diffusion of liquids into and out of the biochar pores. One such treatment process that can be used is vacuum impregnation and vacuum and/or centrifuge extraction. Another such treatment process that can be used is the addition of a surfactant to infused liquid, which infused liquid may be optionally heated or used at ambient temperature or less.

Since research associated with the present invention has identified what physical and chemical properties have the highest impact on plant growth and/or soil health, the treatment process can be geared to treat different forms of raw biochar to achieve treated biochar properties known to enhance these characteristics. For example, if the pH of the biochar needs to be adjusted to enhance the raw biochar performance properties, the treatment may be the infusion of an acid solution into the pores of the biochar using vacuum, surfactant, or other treatment means. This treatment of pore infusion through, for example, the rapid, forced infusion of liquid into and out the pores of the biochar, has further been proven to sustain the adjusted pH levels of the treated biochar for much longer periods than biochar that is simply immersed in an acid solution. By way of another example, if the moisture content needs to be adjusted, then excess liquid can be extracted from the pores using vacuum and/or centrifuge extraction or by using various heating techniques. The above describes a few examples of treatment that result in treated biochar having desired performance properties identified to enhance soil health and plant life.

Figure 5:
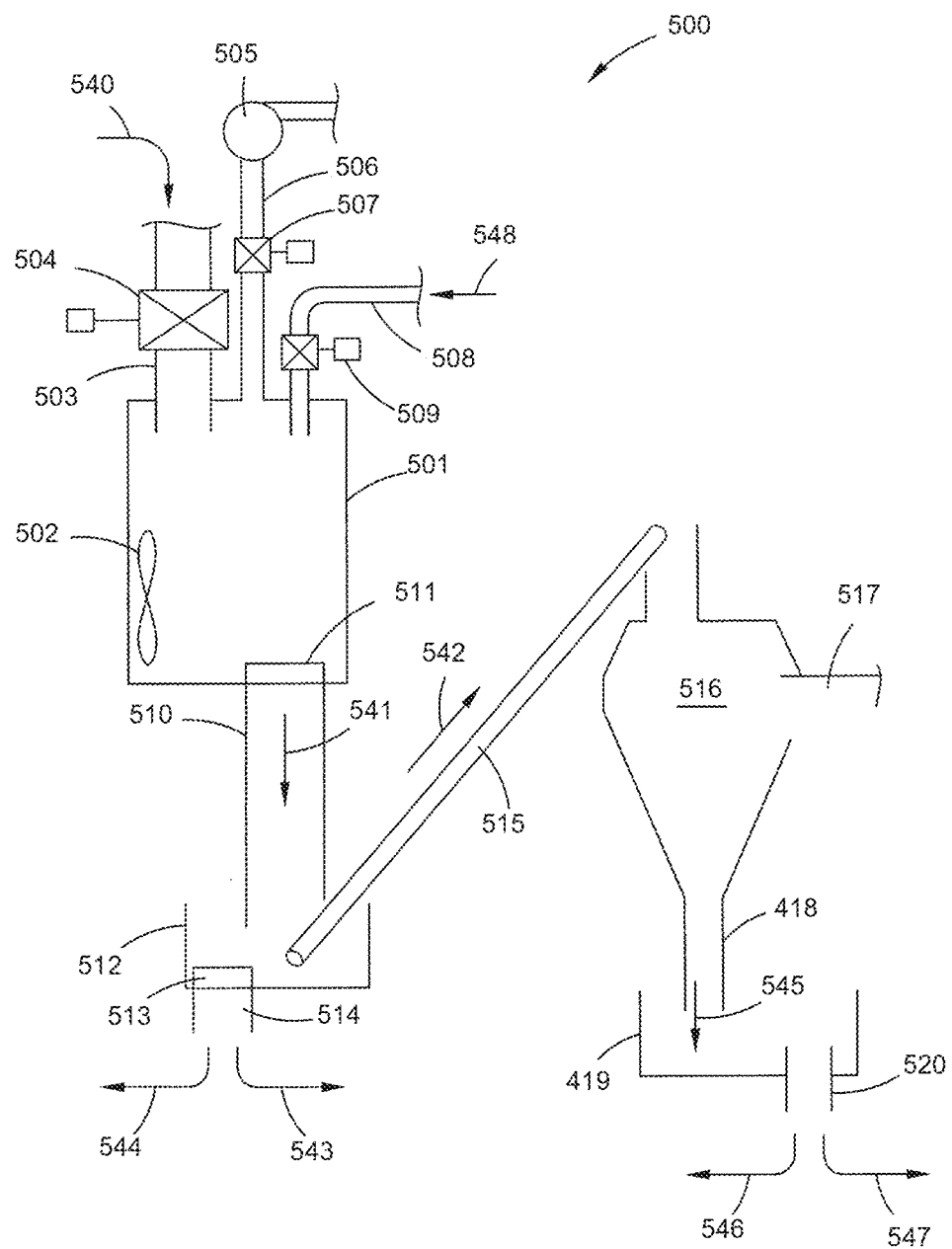
FIG. 5 is a schematic flow diagram of one example of a treatment system for use in accordance with the present invention.

FIG. 5 illustrates one example of a system 500 that utilizes vacuum impregnation to treat raw biochar. Generally, raw biochar particles, and preferably a batch of biochar particles is placed under a vacuum, e.g., ranging from 750 Torr to 400 Torr to 10 Torr or less. The biochar is maintained under vacuum ("vacuum hold time") for anywhere from seconds to 1 minute to 10 minutes, to 100 minutes, or possibly longer. By way of example, for about a 500 pound batch of biochar, a vacuum hold time of from about 1 to about 5 minutes can be used if the reactor is of sufficient size and sufficient infiltrant is available. While under the vacuum an infiltrant may then be introduced into the vacuum chamber containing the biochar. Alternatively, the infiltrant may be introduced into the vacuum chamber before the biochar is placed under a vacuum. Optionally, treatment may also include subjecting the biochar to temperatures during vacuum treatment from ambient to about 250° C.

The infiltrant is drawn into the biochar pore, and preferably drawn into the macropores, the mesopores and the micropores. The infiltrant can coat anywhere from 10% to 50% to 100% of the total pore surface area. The infiltrant can fill and/or coat anywhere from 10% to 50% to 100% of the total pore volume and/or pore surface area, including mesopore and macropore surface area and/or volume.

As described above, the infiltrant can be left in the biochar, with the batch being a treated biochar batch ready for packaging, shipment and use in an agricultural or other application. The infiltrant may also be removed through drying, subsequent vacuum processing, centrifugal force (e.g., cyclone drying machines), with the batch being a treated biochar batch ready for packaging, shipment and use in an agricultural application. A second, third or more infiltration, removal, infiltration and removal, and combinations and variations of these may also be performed on the biochar with optional drying steps between infiltrations to remove residual liquid from the pore structure if needed. In any of these stages the infiltrant may contain organic or inorganic surfactants to assist with the penetration of the infiltrant.

As illustrated in FIG. 5, a system 500 for providing a biochar, preferably having predetermined and uniform properties. The system 500 has a vacuum infiltration tank 501. The vacuum infiltration tank 501 has an inlet line 503 that has a valve 504 that seals the inlet line 503. In operation, the starting biochar is added to vacuum infiltration tank 501 as shown by arrow 540. Once the tank is filled with the starting biochar, a vacuum is pulled on the tank, by a vacuum pump connected to vacuum line 506, which also has valve 507. The starting biochar is held in the vacuum for a vacuum hold time. Infiltrant, as shown by arrow 548 is added to the tank 501 by line 508 having valve 509. The infiltrant is mixed with the biochar in the tank 501 by agitator 502. The mixing process is done under vacuum for a period of time sufficient to have the infiltrant fill the desired amount of pore volume, e.g., up to 100% of the macropores, mesopores and micropores.

Alternatively, the infiltrant may be added to the vacuum infiltration tank 501 before vacuum is pulled on the tank. In this manner, infiltrant is added in the tank in an amount that can be impregnated into the biochar. As the vacuum is pulled, the biochar is circulated in the tank to cause the infiltrant to fill the pore volume. To one skilled in the art, it should be clear that the agitation of the biochar during this process can be performed through various means, such as a rotating tank, rotating agitator, pressure variation in the tank itself, or other means. Additionally, the biochar may be dried using conventional means before even the first treatment. This optional pre-drying can remove liquid from the pores and in some situations may increase the efficiency of impregnation due to pressure changes in the tank.

Pressure is then restored in the tank 501 and the infiltrated biochar is removed, as shown by arrow 541, from the tank 501 to bin 512, by way of a sealing gate 511 and removal line 510. The infiltrated biochar is collected in bin 512, where it can be further processed in several different ways. The infiltrated biochar can be shipped for use as a treated biochar as shown by arrow 543. The infiltrated biochar can be returned to the tank 501 (or a second infiltration tank). If returned to the tank 501 the biochar can be processed with a second infiltration step, a vacuum drying step, a washing step, or combinations and variations of these. The infiltrated biochar can be moved by conveyor 514, as shown by arrow 542, to a drying apparatus 516, e.g., a centrifugal dryer or heater, where water, infiltrant or other liquid is removed by way of line 517, and the dried biochar leaves the dryer through discharge line 518 as shown by arrow 545, and is collected in bin 519. The biochar is removed from the bin by discharge 520. The biochar may be shipped as a treated biochar for use in an agriculture application, as shown by arrow 547. The biochar may also be further processed, as shown by 546. Thus, the biochar could be returned to tank 501 (or a second vacuum infiltration tank) for a further infiltration step. The drying step may be repeated either by returning the dry biochar to the drying apparatus 516, or by running the biochar through a series of drying apparatus, until the predetermined dryness of the biochar is obtained, e.g., between 50% to less than 1% moisture.

The system 500 is illustrative of the system, equipment and processes that can be used for, and to carry out the present inventions. Various other implementations and types of equipment can be used. The vacuum infiltration tank can be a sealable off-axis rotating vessel, chamber or tank. It can have an internal agitator that also when reversed can move material out, empty it, (e.g., a vessel along the lines of a large cement truck, or ready mix truck, that can mix and move material out of the tank, without requiring the tank's orientation to be changed). Washing equipment may be added or utilized at various points in the process, or may be carried out in the vacuum tank, or drier, (e.g., wash fluid added to biochar as it is placed into the drier for removal). Other steps, such as bagging, weighing, the mixing of the biochar with other materials, e.g., fertilized, peat, soil, etc. can be carried out. In all areas of the system referring to vacuum infiltration, optionally positive pressure can be applied, if needed, to enhance the penetration of the infiltrant or to assist with re-infusion of gaseous vapors into the treated char.

As noted above, the biochar may also be treated using a surfactant. The same or similar equipment used in the vacuum infiltration process can be used in the surfactant treatment process. Although it is not necessary to pull a vacuum in the surfactant treatment process, the vacuum infiltration tank or any other rotating vessel, chamber or tank can be used. In the surfactant treatment process, a surfactant, such as *yucca* extract, is added to the infiltrant, e.g., acid wash or water. The rate at with the surfactant is added to the infiltrant may vary depending upon the surfactant used. For example, *yucca* extract can be added at a rate of between 0.1-20%, but more preferably 1-5% by volume of the infiltrant. The infiltrant with surfactant is then mixed with the biochar in a tumbler for several minutes, e.g., 3-5 minutes, without applied vacuum. Optionally, a vacuum or positive pressure may be applied with the surfactant to improve efficiency, but is not necessary. Additionally, infiltrant to which the surfactant or detergent is added may be heated or may be ambient temperature or less. Similarly, the mixture of the surfactant or detergent, as well as the char being treated may be heated, or may be ambient temperature, or less. After tumbling, excess free liquid can be spun-off in the same manner as described above in connection with the vacuum infiltration process. Drying, also as described above in connection with the vacuum infiltration process, is an optional additional step.

C. Benefits of Treatment

As illustrated above, the treatment process, whether using vacuum or surfactant treatment, may include two steps, which in certain applications, may be combined: (i) washing and (ii) inoculation of the pores with an additive. When the desired additive is the same and that being inoculated into the pores, e.g., water, the step of washing the pores and inoculating the pores with an additive may be combined.

While not exclusive, washing is generally done for one of three purposes: (i) to modify the surface of the pore structure of the biochar (i.e., to allow for increased retention of liquids); (ii) to modify the pH of the biochar; and/or (iii) to remove undesired and potentially harmful compounds or gases.

1. Increases Water Holding Capacity/Water Retention Capacity

As demonstrated below, the treatment processes of the invention modify the surfaces of the pore structure to provide enhanced functionality and to control the properties of the biochar to achieve consistent and predicable performance. Using the above treatment processes, anywhere from at least 10% of the total pore surface area up to 90% or more of the total pore surface area may be modified. In some implementations, it may be possible to achieve modification of up to 99% or more of the total pore surface area of the biochar particle. Using the processes set forth above, such modification may be substantially and uniformly achieved for an entire batch of treated biochar.

For example, it is believed that by treating the biochar as set forth above, the hydrophilicity of the surface of the pores of the biochar is modified, allowing for a greater water retention capacity. Further, by treating the biochars as set forth above, gases and other substances are also removed from the pores of the biochar particles, also contributing to the biochar particles' increased water holding capacity. Thus, the ability of the biochar to retain liquids, whether water or additives in solution, is increased, which also increases the ability to load the biochar particles with large volumes of inoculant, infiltrants and/or additives.

A batch of biochar has a bulk density, which is defined as weight in grams (g) of 1 $cm^3$ of loosely poured material that has or retains some free space between the particles. The biochar particles in this batch will also have a solid density, which is the weight in grams (g) of 1 cm3 of just particles, i.e., with the free space between the particles removed. The solid density includes the air space or free space that is contained within the pores, but not the free space between particles. The actual density of the particles is the density of the material in grams (g) of 1 $cm^3$ of material, which makes up the biochar particles, i.e., the particle material with pore volume removed.

In general, as bulk density increases the pore volume would be expected to decrease and with it, the ability to hold infiltrant, e.g., inoculant. Thus, with the infiltration processes, the treated biochars can have impregnation capacities that are larger than could be obtained without infiltration, e.g., the treated biochars can readily have 10%, 30%, 40%, 50%, or most preferably, 60%-100% of their total pore volume filled with an infiltrant, e.g., an inoculant. The impregnation capacity is the amount of a liquid that a biochar particle, or batch of particles, can absorb. The ability to make the pores surface hydrophilic, and to infuse liquid deep into the pore structure through the application of positive or negative pressure and/or a surfactant, alone or in combination, provides the ability to obtain these high impregnation capabilities. The treated biochars can have impregnation capacities, i.e., the amount of infiltrant that a particle can hold on a volume held/total volume of a particle basis, that is greater than 0.2 cm³/cm³ to 0.8 cm³/cm³.

Figure 6:
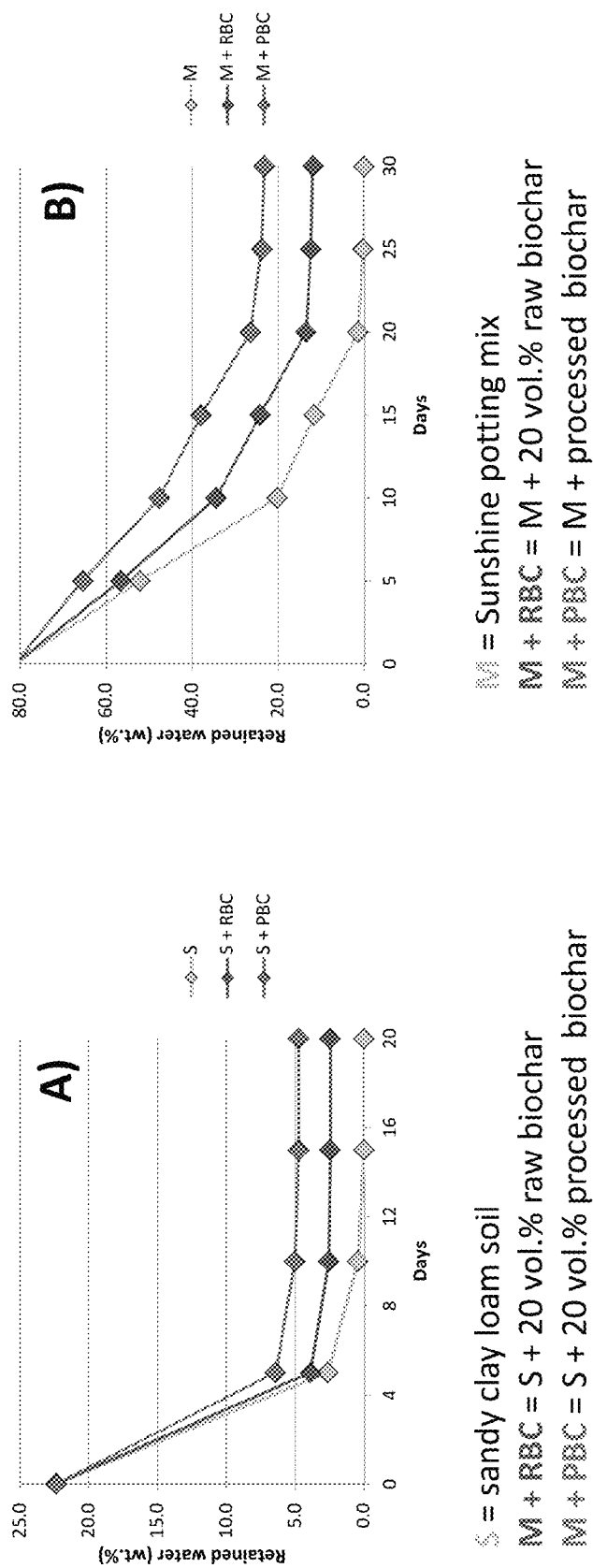
FIG. 6 is a chart showing the water holding capacities of treated biochar as compared to raw biochar and sandy clay loam soil and as compared to raw biochar and sunshine potting soil.

Accordingly, by using the treatment above, the water retention capacity of biochar can be greatly increased over the water retention capacities of various soil types and even raw biochar, thereby holding water and/or nutrients in the plant's root zone longer and ultimately reducing the amount of applied water (through irrigation, rainfall, or other means) needed by up to 50% or more. FIG. 6 is a chart showing the water retention capacities of soils versus raw and treated biochar. In this example, the raw and treated biochar are derived from coconut biomass. The soils sampled are loam and sandy clay soil and sunshine potting soil. The charts show the retained water as a function of time.

In chart A, the bottom line represents the retained water in the sandy claim loam soil over time. The middle line represents the retained water in the sandy clay soil with 20% by volume percent of unprocessed raw biochar. The top line represents the retained water in the sandy clay loam soil with 20% by volume percent of treated biochar (pH adjusted and inoculated biochar). Chart B represents the same using sunshine potting soil rather than sandy clay loam soil.

As illustrated in FIG. 6, the treated biochar has an increased water retention capacity over raw biochar of approximately 1.5 times the raw biochar. Similarly, results are shown with treated biochar derived from pine, also showing an approximate 1.5 times increase in water retention capacity over raw biochar. With certain biochar, the water retention capacity of treated biochar could be as great as three time that of raw biochar.

"Water holding capacity," which may also be referred to as "Water Retention Capacity," is the amount of water that can be held both internally within the porous structure and in the interparticle void spaces in a given batch of particles. While a summary of the method of measure is provided above, a more specific method of measuring water holding capacity/water retention capacity is measured by the following procedure: (i) drying a sample of biochar under temperatures of 105° C. for a period of 24 hours or using another scientifically acceptable technique to reduce the moisture content of the biochar to less than 2%, less than 1%; and preferably less than 0.5% (ii) placing a measured amount of dry biochar in a container; (iii) filling the container having the measured amount of biochar with water such that the biochar is completely immersed in the water; (iv) letting the water remain in the container having the measured amount of biochar for at least ten minutes or treating the biochar in accordance with the invention by infusing with water when the biochar is a treated biochar; (v) draining the water from the container until the water ceases to drain; (vi) weighing the biochar in the container (i.e., wet weight); (vii) again drying the biochar by heating the biochar under temperatures of 105° C. for a period of 24 hours or using another scientifically acceptable technique to reduce the moisture content of the biochar to less than 2% and preferably less than 1%; and (viii) weighing the dry biochar again (i.e., dry weight) and, for purposes of a volumetric measure, determining the volume of the biochar.

Figure 7:
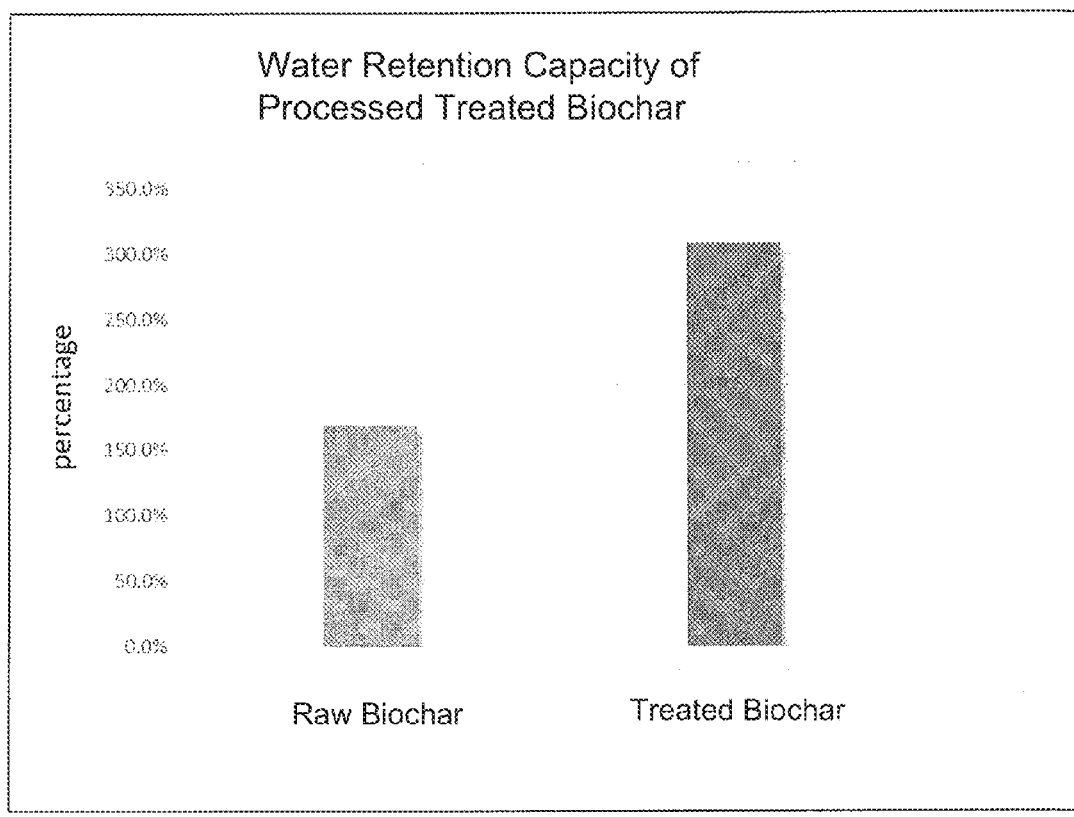
FIG. 7 illustrates the different water retention capacities of raw biochar versus treated biochar measured gravimetrically.

Measured gravimetrically, the water holding/water retention capacity is determined by measuring the difference in weight of the biochar from step (vi) to step (viii) over the weight of the biochar from step (viii) (i.e., wet weight-dry weight/dry weight). FIG. 7 illustrates the different water retention capacities of raw biochar verse treated biochar measured gravimetrically. As illustrated, water retention capacity of raw biochar can be between 100-200%, whereas treated biochar can have water retention capacities measured gravimetrically between 200-400%.

Water holding capacity can also be measured volumetrically and represented as a percent of the volume of water retained in the biochar after gravitationally draining the excess water/volume of biochar The volume of water retained in the biochar after draining the water can be determined from the difference between the water added to the container and water drained off the container or from the difference in the weight of the wet biochar from the weight of the dry biochar converted to a volumetric measurement. This percentage water holding capacity for treated biochar may be 50-55 percent and above by volume.

Given biochar's increased water retention capacity, the application of the treated biochar and even the raw biochar greatly assists with the reduction of water and/or nutrient application. It has been discovered that these same benefits can be imparted to agricultural growth.

Figure 8:
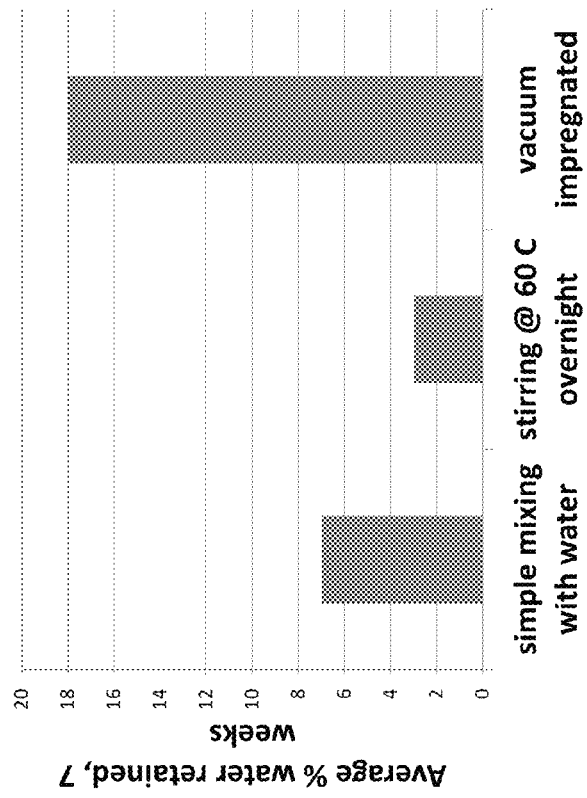
FIG. 8 is a chart showing the retained water in vacuum impregnated biochar over other biochars after a seven week period.

Treated biochar of the present invention has also demonstrated the ability to retain more water than raw biochar after exposure to the environment for defined periods of time. For purposes of this application "remaining water content" can be defined as the total amount of water that remains held by the biochar after exposure to the environment for certain amount of time. Exposure to environment is exposure at ambient temperature and pressures. Under this definition, remaining water content can be measured by (i) creating a sample of biochar that has reached its maximum water holding capacity; (ii) determining the total water content by thermogravimetric analysis ($H_2O$ (TGA)), as described above on a sample removed from the output of step (i) above, (iii) exposing the biochar in the remaining sample to the environment for a period of 2 weeks (15 days, 360 hrs.); (iv) determining the remaining water content by thermogravimetric analysis ($H_2O$ (TGA)); and (v) normalizing the remaining (retained) water in mL to 1 kg or 1 L biochar. The percentage of water remaining after exposure for this two week period can be calculated by the remaining water content of the biochar after the predetermined period over the water content of the biochar at the commencement of the two week period. Using this test, treated biochar has shown to retain water at rates over 4× that of raw biochar. Testing has further demonstrated that the following amount of water can remain in treated biochar after two weeks of exposure to the environment: 100-650 mL/kg; 45-150 mL/L; 12-30 gal/ton; 3-10 gal/yd3 after 360 hours (15 days) of exposure to the environment. In this manner, and as illustrated in FIG. 8, biochar treated through vacuum impregnation can increase the amount of retained water in biochar about 3× compared to other methods even after seven weeks. In general, the more porous and the higher the surface area of a given material, the higher the water retention capacity. Further, it is theorized that by modifying the hydrophilicity/hydrophobicity of the pore surfaces, greater water holding capacity and controlled release may be obtained. Thus, viewed as a weight percent, e.g., the weight of retained water to weight of biochar, examples of the present biochars can retain more than 5% of their weight, more than 10% of their weight, and more than 15% of their weight, and even more than 50% of their weight compared to an average soil which may retain 2% or less, or between 100-600 ml/kg by weight of biochar.

Tests have also shown that treated biochars that show weight loss of >1% in the interval between 43-60° C. when analyzed by the Thermal Gravimetric Analysis (TGA) (as described below) demonstrate greater water holding and content capacities over raw biochars. Weight loss of >5%-15% in the interval between 38-68° C. when analyzed by the Thermal Gravimetric Analysis (TGA) using sequences of time and temperature disclosed in the following paragraphs or others may also be realized. Weight percentage ranges may vary from between >1%-15% in temperature ranges between 38-68° C., or subsets thereof, to distinguish between treated biochar and raw biochar.

Figure 9:
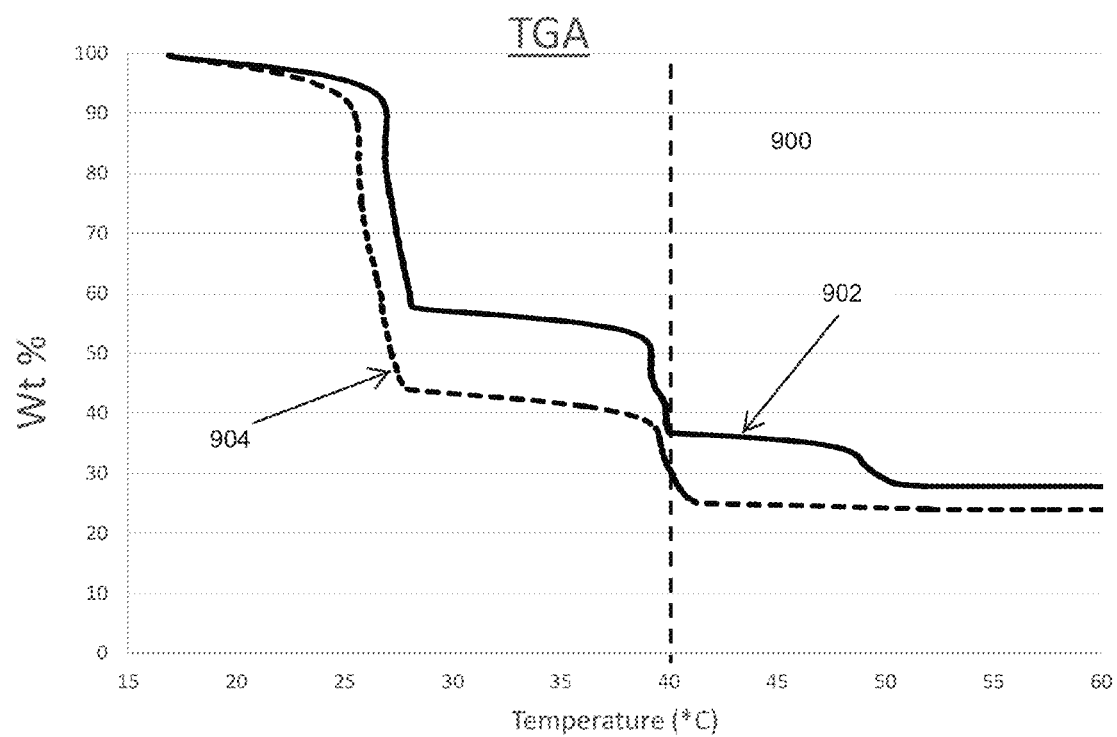
FIG. 9 is a chart showing the weight loss of treated biochars versus raw biochar samples when heated at varying temperatures using a TGA testing method.

FIG. 9 is a chart 900 showing the weight loss of treated biochars 902 versus raw biochar samples 904 when heated at varying temperatures using the TGA testing described below. As illustrated, the treated biochars 902 continue to exhibit weight loss when heated between 40-60° C. when analyzed by the Thermal Gravimetric Analysis (TGA) (described below), whereas the weight loss in raw biochar 804 between the same temperature ranges levels off. Thus, testing demonstrates the presence of additional moisture content in treated biochars 902 versus raw biochars 904.

In particular, the treated biochars 902 exhibit substantial water loss when heated in inert gas such as nitrogen following treatment. More particularly, when heated for 25 minutes at each of the following temperatures 20, 30, 40, 50 and 60° C. the treated samples lose about 5-% to 15% in the interval 43-60° C. and upward of 20-30% in the interval between 38-68° C. The samples to determine the water content of the raw biochar were obtained by mixing a measured amount of biochar and water, stirring the biochar and water for 2 minutes, draining off the water, measuring moisture content and then subjecting the sample to TGA. The samples for the treated biochar were obtained by using the same measured amount of biochar as used in the raw biochar sample, and impregnating the biochar under vacuum. Similar results are expected with biochar treated with a treatment process consistent with those described in this disclosure with the same amount of water as used with the raw biochar. The moisture content is then measured and the sample is subjected to TGA described above.

The sequences of time and temperature conditions for evaluating the effect of biochars heating in inert atmosphere is defined in this application as the "Bontchev-Cheyne Test" ("BCT"). The BCT is run using samples obtained, as described above, and applying Thermal Gravimetric Analysis (TGA) carried out using a Hitachi STA 7200 analyzer under nitrogen flow at the rate of 110 mL/min. The biochar samples are heated for 25 minutes at each of the following temperatures: 20, 30, 40, 50 and 60° C. The sample weights are measured at the end of each dwell step, at the beginning and at the end of the experiment. The analyzer also continually measures and records weight over time. Biochars treated with vacuum infiltration to enhance water holding or retention capacities typically exhibit weight loss of >5% in the interval between 38-68° C., >1% in the interval between 43-60° C. Biochars with greater water holding or retention capacities can exhibit >5% weight loss in the interval between 43-60° C. measured using the above described BCT.

Figure 10:
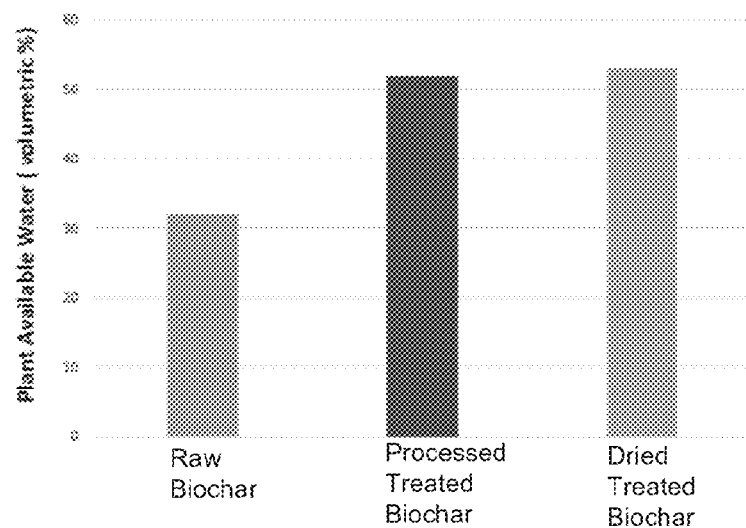
FIG. 10 illustrates the plant available water in raw biochar, versus treated biochar and treated dried biochar.

Lastly, as illustrated in FIG. 10, plant available water is greatly increased in treated biochar over that of raw biochar. FIG. 10 illustrates the plant available water in raw biochar, versus treated biochar and treated dried biochar and illustrates that treated biochar can have a plant available water percent of greater than 35% by volume.

"Plant Available Water" is the amount of unbound water in the biochar available for plants to uptake. This is calculated by subtracting the volumetric water content at field capacity from the volumetric water content at the permanent wilting point, which is the point when no water is available for the plants. Field capacity is generally expressed as the bulk water content retained in at −33 J/kg (or −0.33 bar) of hydraulic head or suction pressure. Permanent wilting point is generally expressed as the bulk water content retained at −1500 J/kg (or −15 bar) of hydraulic head or suction pressure. Methods for measuring plant available water are well-known in the industry and use pressure plate extractors, which are commercially available or can be built using well-known principles of operation.

2. Adjusts pH

Figure 11:
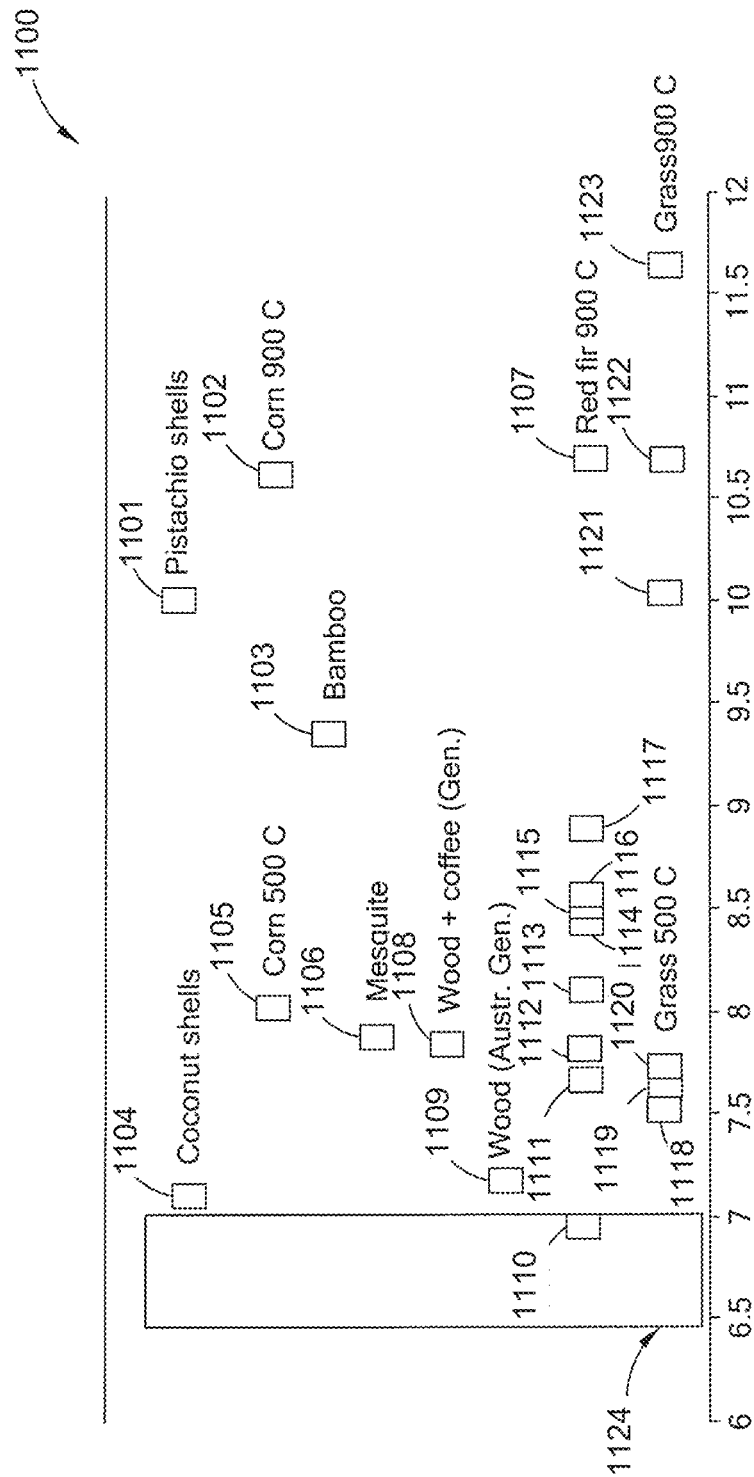
FIG. 11 is a graph showing the pH of various starting biochars that were made from different starting materials and pyrolysis process temperatures.
Figure 12:
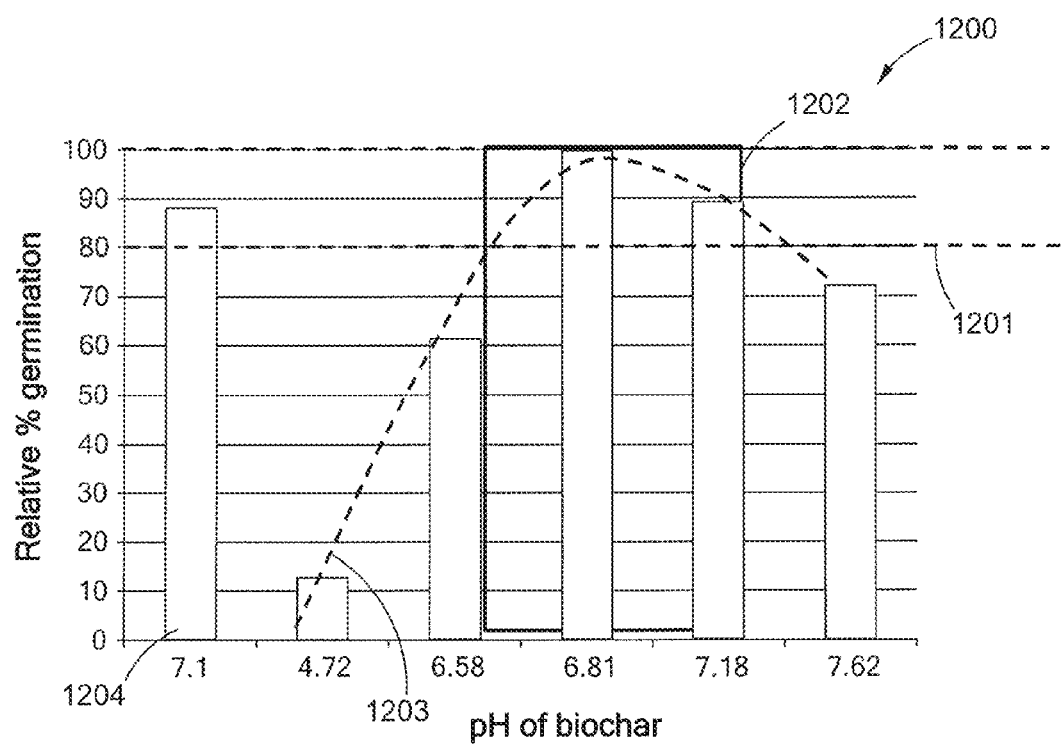
FIG. 12 is a chart showing various pH ranges and germination for treated biochars.

With regard to treatment for pH adjustment, the above described vacuum infiltration processes and/or surfactant treatment processes have the ability to take raw biochars having detrimental or deleterious pHs and transform those biochars into a treated biochar having pH that is in an optimal range for most plant growth, and soil health. Turning to FIG. 11, a graph 1100 is provided that shows the pH of various starting raw biochars that were made from different starting materials and pyrolysis process temperatures, including coconut shells 1104, pistachio shells 1101, corn at 500° C. 1105, corn at 900° C. 1102, bamboo 1103, mesquite 1106, wood and coffee 1108, wood (Australia) 1109, various soft woods 1110, 1111, 1112, 1113, 1114, 1115, 1116, 1117, red fir at 900° C. 1107, various grasses at 500° C. 1118, 1119, 1120, grass 1121, and grass at 900° C. 1123. The vacuum infiltration process, among other processes, can alter the pH from the various undesirable pH levels and bring the pH into the preferred, optimal range 1124 for most plant growth, soil health and combinations of these. FIG. 12 is a chart 1200 showing percentage of germination for lettuce plants for particular pHs, and an desired germination range 1201. A control 1204 is compared with an optimal pH range 1202, and a distribution 1203 of growth rates across pHs is shown.

If treated for pH adjustment, the treated biochar takes a few days after treatment for the pH to normalize. Once normalized, tests have proven that pH altered biochar remains at a stable pH, typically lower than the pH of the raw biochar, for up to 12 months or more after treatment.

For example, the treatment process of the present invention can remove and/or neutralize inorganic compounds, such as the calcium hydroxide ($(CaOH)2$), potassium oxide ($K_2OK_2OK_2O$), magnesium oxide (MgO), magnesium hydroxide ($Mg(OH)_2$), and many others that are formed during pyrolysis, and are fixed to the biochar pore surfaces. These inorganics, in particular calcium hydroxide, adversely affect the biochar's pH, making the pH in some instances as high as 8.5, 9.5, 10.5 and 11.2. These high pH ranges are deleterious, detrimental to crops, and may kill or adversely affect the plants, sometimes rendering an entire field a loss.

The calcium hydroxide, and other inorganics, cannot readily and quickly be removed by simple washing of the biochar, even in an acid bath. It cannot be removed by drying the biochar, such as by heating, vacuum, or centrifugal force. It is theorized that these techniques and methodologies cannot reach or otherwise affect the various pore surfaces, e.g., macro-, meso- and micro- in any viable or efficacious manner; and thus cannot remove or otherwise neutralize the calcium hydroxide.

Upon modification of the pore surface area by removal and/or neutralization of the calcium hydroxide the pH of the biochar can be reduced to the range of about pH 5 to about pH 8, and more preferably from about pH 6.4 to about 7.2, and still more preferably around 6.5 to 6.8, recognizing that other ranges and pHs are contemplated and may prove useful, under specific environmental situations. Thus, the present treated biochars, particles, batches and both, have most, essentially all, and more preferably all, of their pore surfaces modified by the removal, neutralization and both, of the calcium hydroxide that is present in the starting biochar material. These treated biochars have pHs in the range of about 5 to about 8, about 6.5 to about 7.5, about 6.4 to about 7, and about 6.8. Prior to and before testing, biochar is passed through a 2 mm sieve before pH is measured. All measurements are taken according to Rajkovich et. al, *Corn growth and nitrogen nutrition after additions of biochars with varying properties to a temperate soil*, Biol. Fertil. Soils (2011), from which the IBI method is based.

There are a wide variety of tests, apparatus and equipment for making pH measurements. For example, and preferably when addressing the pH of biochar, batches, particles and pore surfaces of those particles, two appropriates for measuring pH are the Test Method for the US Composting Council ("TMCC") 4.11-A and the pH Test Method promulgated by the International Biochar Initiative. The test method for the TMCC comprises mixing biochar with distilled water in 1:5 [mass:volume] ratio, e.g., 50 grams of biochar is added to 250 ml of pH 7.0±0.02 water and is stirred for 10 minutes; the pH is then the measured pH of the slurry. The pH Test Method promulgated by the International Biochar Initiative comprises 5 grams of biochar is added to 100 ml of water pH=7.0±0.02 and the mixture is tumbled for 90 minutes; the pH of the slurry is measured at the end of the 90 minutes of tumbling.

3. Removing/Neutralizing Deleterious Materials

Further, the treatment processes are capable of modifying the pore surfaces to remove or neutralize deleterious materials that are otherwise difficult, if not for all practical purpose, impossible to mitigate. For example, heavy metals, transition metals, sodium and phytotoxic organics, polycyclic aromatic hydrocarbons, volatile organic compounds (VOCs), and perhaps other phytotoxins. Thus, by treating the biochar in accordance with the treatment processes set forth and described above, the resulting treated biochar has essentially all, and more preferably all, of their pore surfaces modified by the removal, neutralization and both, of one or more deleterious, harmful, potentially harmful material that is present in the starting biochar material.

For example, washing can reduce the total percentage of residual organic compounds (ROC), including both the percentage of heavy ROCs and percentage of VOCs. Through treatment, the total ROC can be reduced to 0-25% wt. %, percentage heavy ROC content can be reduced to 0-20% wt. % and VOC content can be reduced to less than 5% wt. %. For purposes of this application, "Residual organic compounds" (ROCs) are defined as compounds that burn off during thermogravimetric analysis, as defined above, between 150 degrees C. and 950 degrees C. Residual organic compounds include, but are not limited to, phenols, polyaromatic hydrocarbons, monoaromatic hydrocarbons, acids, alcohols, esters, ethers, ketones, sugars, alkanes and alkenes. Of the ROCs, those that burn off using thermogravimetric analysis between 150 degrees C. and 550 degrees are considered light organic compounds (volatiles or VOCs), and those that burn off between 550 degrees C. and 950 degrees C. are heavy organic compounds. It should be noted that there may be some inorganic compounds which also are burned off during TGA analysis in these temperature ranges, but these are generally a very low percentage of the total emission and can be disregarded in the vast majority of cases as slight variations. In any of these measurements, a gas chromatograph/mass spectrometer may be used if needed for higher degrees of precision.

Figure 13:
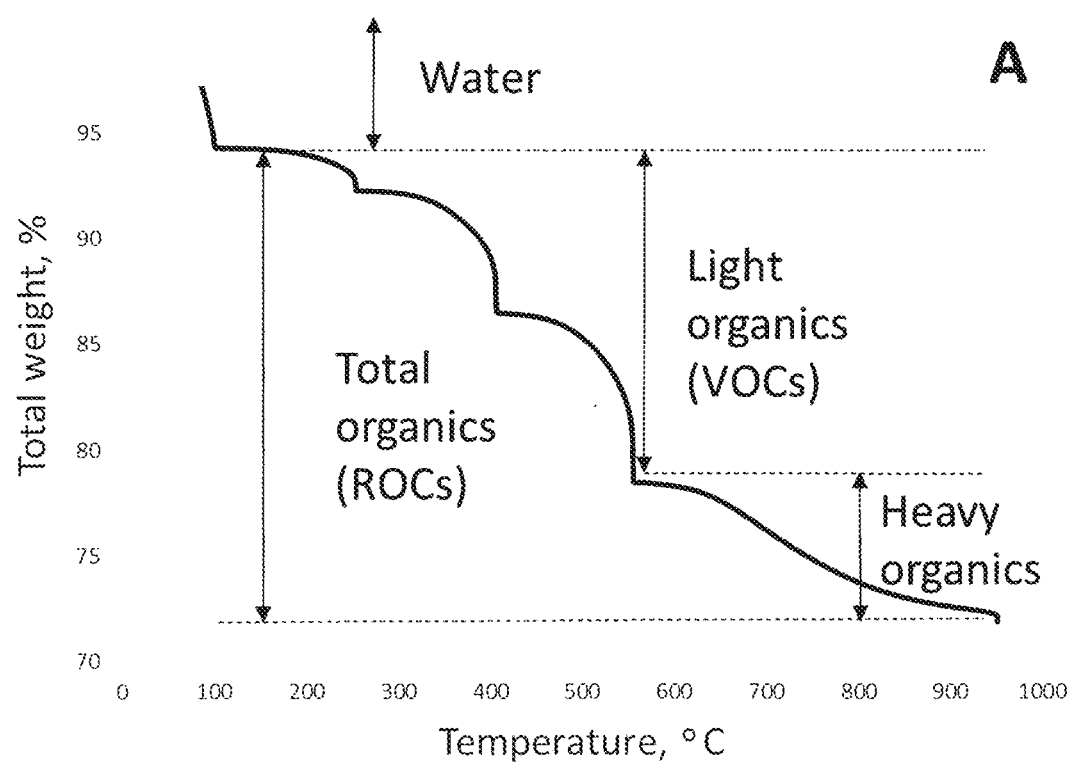
FIG. 13 is a Thermogravimetric Analysis (TGA) plot showing the measurement of water content, heavy organics and light organics in a sample.

The percent water, total organic compounds, total light organic compounds (volatiles or VOC) and total heavy organic compounds, as referenced in this application as contained in a biochar particle or particles in a sample may all be measured by thermogravimetric analysis. Thermogravimetric analysis is performed by a Hitachi STA 7200 analyzer or similar piece of equipment under nitrogen flow at the rate of 110 mL/min. The biochar samples are heated for predetermined periods of time, e.g., 20 minutes, at a variety of temperatures between 100 and 950° C. The sample weights are measured at the end of each dwell step and at the beginning and at the end of the experiment. Thermogravimetric analysis of a given sample indicating percentage water in a sample is determined by % mass loss measured between standard temperature and 150 degrees C. Thermogravimetric analysis of a given sample indicating percentage of residual organic compounds is measured by percentage mass loss sustained between 150 degrees C. and 950 degrees C. Thermogravimetric analysis of a given sample indicating percentage of light organic compounds (volatiles) is measured by percentage mass loss sustained between 150 degrees C. and 550 degrees C. Thermogravimetric analysis of a given sample indicating percentage of heavy organic compounds is measured by percentage mass loss sustained between 550 degrees C. and 950 degrees C. FIG. 13 is an example of a Thermogravimetric Analysis (TGA) plot outlining the above explanation and the measure of water, light organics and heavy organics.

4. Impregnation and/or Inoculation with Infiltrants or Additives

In addition to mitigating or removing deleterious pore surface properties, by treating the pores of the biochar through a forced or rapid infiltration process, such as those described above, the pore surface properties of the biochar can be enhanced. Such treatment processes may also permit subsequent processing, may modify the pore surface to provide predetermined properties to the biochar, and/or provide combinations and variations of these effects. For example, it may be desirable or otherwise advantageous to coat substantially all, or all of the biochar pore surface with a surface modifying agent or treatment to provide a predetermined feature to the biochar, e.g., surface charge and charge density, surface species and distribution, targeted nutrient addition, magnetic modifications, root growth facilitator, and water absorptivity and water retention properties.

Accordingly, after washing, pH adjustment and/or moisture modification, the biochar may be subject to further treatment, using the same methods to inoculate the pores of the biochar with an additive. For example, the pores may be substantially filled or completely filled with agents to provide enhanced performance features to the biochar, such as increased plant growth, nutrient delivery, water retention, nutrient retention, disadvantageous species control, e.g., weeds, disease causing bacteria, insects, volunteer crops, etc. By infusing liquid deep into the pore structure through the application of positive or negative pressure and/or a surfactant, alone or in combination, provides the ability to impregnate the macropores of the biochar with soil enhancing solutions and solids. The soil enhancing agent may include, but not be limited to, any of the following: water, water solutions of salts, inorganic and organic liquids of different polarities, liquid organic compounds or combinations of organic compounds and solvents, mineral and organic oils, slurries and suspensions, supercritical liquids, fertilizers, plant growth promoting rhizobacteria, free-living and nodule-forming nitrogen fixing bacteria, organic decomposers, nitrifying bacteria, phosphate solubilizing bacteria, biocontrol agents, bioremediation agents, saprotrophic fungi, ectomycorrhizae and endomycorrhizae, among others.

Fertilizers that may be infused into the biochar include, but are not limited to, the following sources of nitrogen, phosphorous, and potassium: urea, ammonium nitrate, calcium nitrate, ammonium sulfate, monoammonium phosphate, ammonium polyphosphate, potassium sulfate, or potassium chloride Similar beneficial results are expected from other additives, such as fungicides, insecticides, nematicides, plant hormones, beneficial microbial spores, or secondary signal activators, which may also be added to the biochar in a similar manner as a fertilizer. Additionally, beneficial macro- and micro-nutrients such as, calcium, magnesium, sulfur, boron, zinc, iron, manganese, molybdenum, copper and chloride may also be infused into the biochar.

Examples of compounds, in addition to fertilizer, that may be infused into the pores of the biochar include, but are not limited to: 2,1,3-Benzothiadiazole (BTH), an inducer of systemic acquired resistance that confers broad spectrum disease resistance (including soil borne pathogens); signaling agents similar to BTH in mechanism or structure that protects against a broad range or specific plant pathogens; biopesticides; herbicides; and fungicides.

In one example, a 1000 ppm $NO_3^-$ N fertilizer solution is infused into the pores of the biochar. As discussed above, the method to infuse biochar with the fertilizer solution may be accomplished generally by placing the biochar in a vacuum infiltration tank or other sealable rotating vessel, chamber or tank. When using vacuum infiltration, a vacuum may be pulled on the biochar and then the solution may be introduced into the tank. Alternatively, the solution and biochar may both be introduced into the tank and, once introduced, a vacuum is pulled. Based upon the determined total pore volume of the biochar or the incipient wetness, the amount of solution to introduce into the tank necessary to fill the pore of the biochar can be determined. When infused in this manner, significantly more nutrients can be held in a given quantity of biochar versus direct contact with the nutrients alone.

When using a surfactant, the biochar and fertilizer solution may be added to a tank along with 0.1-20% of surfactant, but more preferably 1-5% of surfactant by volume of fertilizer solution. The surfactant or detergent aids in the penetration of the wash solution into the pores of the biochar. The same or similar equipment used in the vacuum infiltration process can be used in the surfactant treatment process. Although it is not necessary to pull a vacuum in the surfactant treatment process, the vacuum infiltration tank or any other rotating vessel, chamber or tank can be used. Again, while it is not necessary to pull a vacuum, a vacuum may be pulled. Further, the surfactant can be added with or without heat.

Beneficial bacteria includes, for example, plant growth promoting rhizobacteria, free-living and nodule-forming nitrogen fixing bacteria, organic decomposers, nitrifying bacteria, phosphate solubilizing bacteria, biocontrol agents, bioremediation agents, archea, actinomycetes, and combinations and variations of these. Beneficial fungi include, for example, saprotrophic fungi, ectomycorrhizae, endomycorrhizae, and combinations and variations of these.

Biochar may be infused in the same manner as described above with nutrients, vitamins, drugs and/or other supplements, or a combination of any of the foregoing, for consumption by either humans and/or animals.

Thus, treated biochar can have a microbial community in its pores (macro-, meso-, micro-, and combinations and variations of these), on its pore surfaces, embedded in it, located on its surface, and combinations and variations of these. The microbial community can have several different types, e.g., species, of biologics, such as different types of bacteria, or fungi, or it may have only a single type. A primary purpose, among many purposes, in selecting the microbial population is looking toward a population that will initiate a healthy soil, e.g., one that is beneficial for, enhances or otherwise advance the desired growth of plants under particular environmental conditions. However, the microbes may also be targeted towards increasing animal health.

Typically the prior art teaches placing biochar on soils without 'precharging' with bacteria or combining the biochar with compost and using this mixture as a soil amendment. The nature of the microbial population in this compost mixture is poorly disclosed by the prior art. Thus, through impregnation of the biochar particles, one can achieve a predetermined and controllable amount of a microbial community, e.g., population, into the soil. This integration of a microbial community with a biochar particle, and biochar batches provides the ability to have controlled addition, use and release of the microbes in the community. This integration further enhances, promotes and facilitates the growth of roots, e.g., micro-roots, in the biochar pores, e.g., pore morphology, pore volume.

One manner in which the population of a microbial community can be determined is by PLFA (Phospholipid-derived fatty acids) analysis. Biological cell membranes are composed of a phospholipid bilayer with fatty acid side chains that are unique to certain families of organisms. PLFA analysis extracts the fatty acid side chains of phospholipid bilayers and measures the quantity of these biomarkers using GC-MS. An estimate of the microbial community population can thus be determined through PLFA analysis. The microbial activity may also be inferred through PLFA analysis by monitoring the transformation of specific fatty acids. Next generation sequencing of the conserved ribosomal RNA regions of the bacteria and fungi may allow for more direct and accurate measurements than PLFA.

Treated biochars can have a mixture of bacteria and fungi. For example, a preferred functional biochar, can have a preferred range for bacterial population of from about 50-5000000 micrograms/g biochar; and for fungi, from about 5 to 500000 micrograms/g biochar.

Compared to a biochar that has been bathed with a compost tea, which may have a relatively short, e.g., a few days for the life of the microbes, the impregnated populations of examples of the present treated biochars, are stable over substantially longer periods of time, e.g., at least an 8 week period and in some cases 1 year or more as measured by PLFA. Thus, the impregnation of the biochar with a microbial population provides for extended life of the microbes by at least 5×, 10×, or more. In fact, some microbes may be better suited to surfactant infiltration versus vacuum infiltration and vice versa and this may impact the shelf life, penetration, viability, or other characteristics of the microbes.

Figure 14:
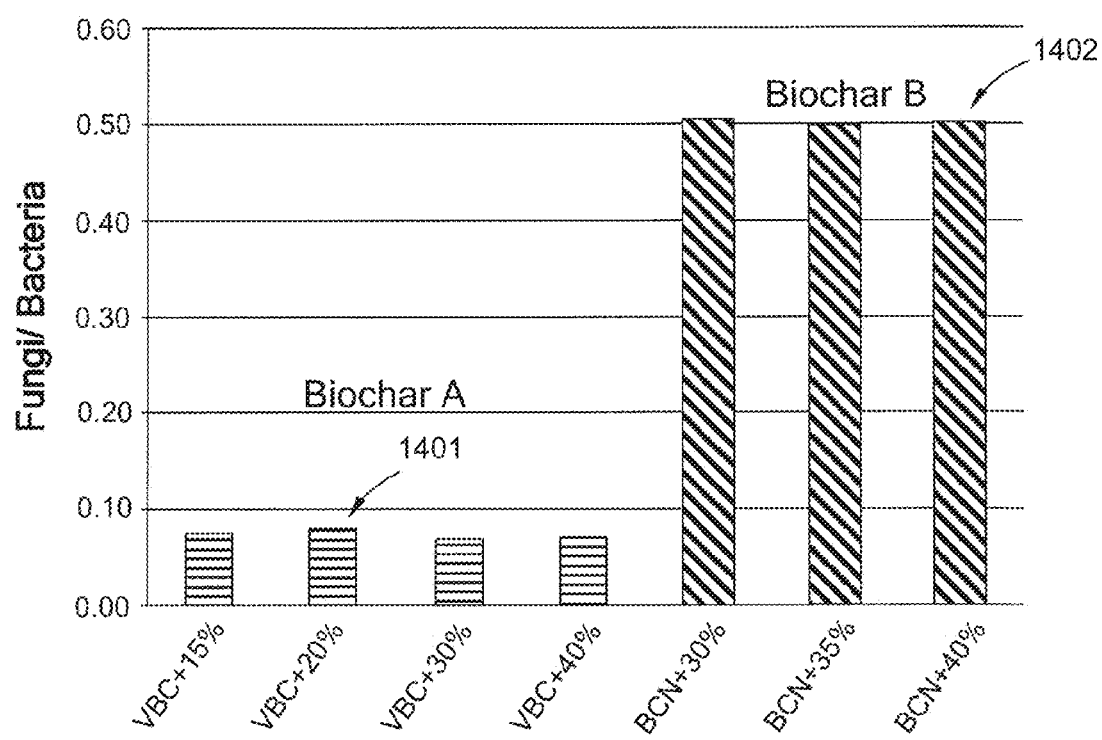
FIG. 14 is a chart comparing examples of biochars.

FIG. 14 shows the total fungi/bacteria ratio for two biochars derived from different biochar starting materials, e.g., feedstocks. Each biochar was loaded with different levels of moisture, and the total fungi/bacteria ratio was monitored during the first week. Biochar A 1401 showed a constant total fungi/bacteria ratio of 0.08 across moisture levels ranging from 15% to 40%, while Biochar B 1402 showed a constant total fungi/bacteria ratio of 0.50 for moisture levels ranging from 30% to 40%. It is theorized that, a fungi/bacteria ratio between 0.05 and 0.60 is an effective prescription for a stable biochar composition. This composition allows a commercially viable product, which has sufficient shelf life that it can be delivered to storage houses waiting for the proper planting window.

As used herein, unless stated otherwise, the stable shelf life of an example of a biochar product having a microbial population is the period of time over which the product can be stored in a warehouse, e.g., dry environment, temperature between 40° F.-90° F., with a less than 50% decrease in microbial population.

It is theorized that the difference in the observed total fungi/total bacteria ratios of may also be explainable by the structures of the biochars. Biochar's having an open pore structure, e.g., more interconnected pores, promotes more bacteria formation; while closed pores, e.g., relatively non-connected nature of the pores, tends to promote fungi formation. Biochars with differing microbial communities may be beneficial for specific applications in commercial agriculture. Thus, custom or tailored loading of the microbial population may be a desired implementation of the present invention.

Figure 16:
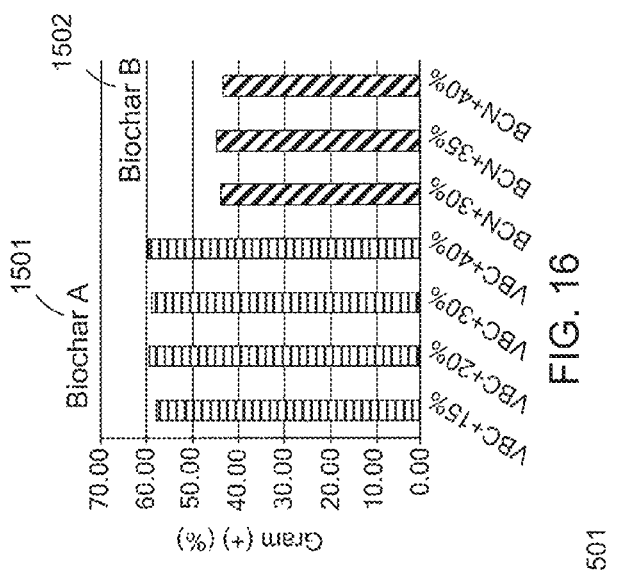
FIGS. 15, 16, 17 are charts comparing different examples of biochars.
Figure 15:
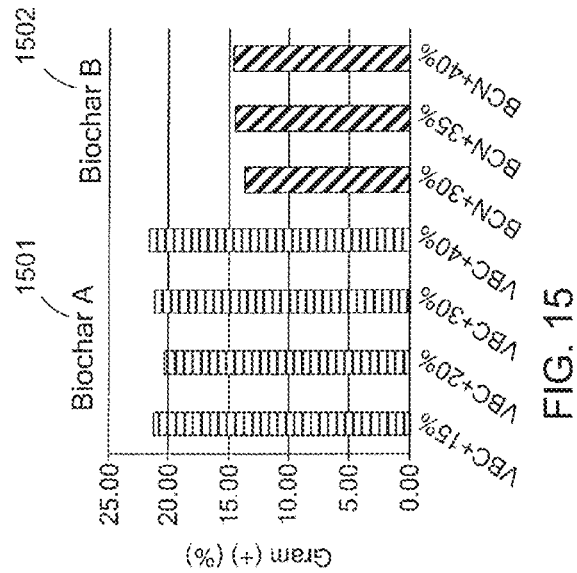
Figure 17:
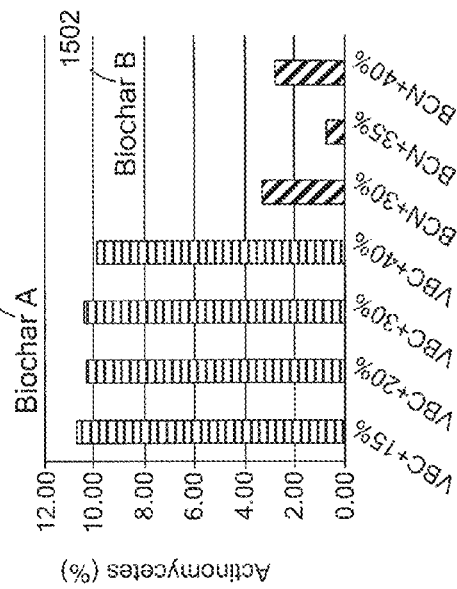

For example, as shown in FIGS. 15, 16 and 17, Biochar A 1501 shows that it has a greater population of, e.g., is inhabited by, more gram negative, gram positive and actinomycetes than Biochar B 1502. Thus, for example, Biochar A would be more applicable for use with certain agricultural crops in which plant growth promoting rhizobacterial (PGPR) species in the actinomycetes, gram (−)*pseudomonas*, and *bacillus* groups are used for nutrient utilization and uptake. Many vegetable and short cycle row crops such as tomatoes, lettuce, and celery form mutualistic relationships with bacteria that lead to the formation of biofilms on root hairs that function not only in nutrient uptake but also in plant pathogen resistance. The presence of biofilms in Biochar A would consequently promote bacterial colonization of plant root hairs as they encounter the biochar in the soil.

It is further theorized that, in general, biochars with greater fungal development may be better suited for perennial crops such as grapes, almonds, blueberries, and strawberries in which symbiotic relationships with arbuscular mycorrhizal fungi (AMF) are favored over PGPRs. The presence of high concentrations of AMF spores in biochars can therefore rapidly promote fungal colonization of plant root hairs leading to extensive mycelial development. Increased plant root associations with mycelial filaments would consequently increase nutrient and water uptake.

In general, bacteria communicate via the distribution of signaling molecules which trigger a variety of behaviors like swarming (rapid surface colonization), nodulation (nitrogen fixation), and virulence. Biochars can bind signaling molecules and in particular it is believed can bind a major signaling molecule to their surface. This binding ability can be dependent upon many factors including on the pyrolysis temperature. This dependency on pyrolysis temperature and other factors can be overcome, mitigated, by the use of examples of the present vacuum infiltration techniques. For example, a signaling molecule that is involved in quorum sensing-multicellular-like cross-talk found in prokaryotes can be bound to the surface of biochars. Concentration of biochars required to bind the signaling molecule decreased as the surface area of biochars increased. These signaling molecules may be added to the surface of a biochar and may be used to manipulate the behavior of the bacteria. An example of such a use would be to bind the molecules which inhibit cell-to-cell communication and could be useful in hindering plant pathogens; using techniques in the present invention signaling molecules may be added to the surface of a biochar to engineer specific responses from various naturally occurring bacteria.

Further, a benefit of examples of biochars of the present inventions is the ability to provide an environment where bacteria communities can flourish. Bacterial communities can shift their morphology to increase nutritional access and decrease predation. One such modification is that the bacteria may attach to surfaces, such as those found in biochar, in a densely compacted community. In this compacted form they may form an extracellular polymeric substance (EPS) matrix called a biofilm. These communities can contain a few hundred different species which find shelter under the protective EPS coating from predatory protozoa, pathogens, contaminants, and other environmental stressors. Thus, examples of biochars produced in accordance with the vacuum infiltration methods may be used as carriers for established biofilms; and thus biochars with such films many used in agricultural settings.

5. Batch Treatment/Bulk Production

As demonstrated above, the treatment processes described above are particularly well suited for large scale production of biochar. The processes and biochars of the present invention provides a unique capability to select starting materials and pyrolysis techniques solely on the basis of obtaining a particular structure, e.g., pore size, density, pore volume, amount of open pores, interconnectivity, tortuosity, etc. Thus, these starting materials and processes can be selected without regard to adverse, harmful, phytotoxic side effects that may come from the materials and processes. This is possible, because the infiltration steps have the capability of mitigating, removing or otherwise address those adverse side effects. In this manner, a truly custom biochar can be made, with any adverse side effects of the material selection and pyrolysis process being mitigated in later processing steps.

Further, the processes are capable of treating a large, potentially variable, batch of biochar to provide the same, generally uniform, predetermined customized characteristics for which treatment was designed to achieve, e.g., pH adjustment. Treatment can result in treated biochar batches in which 50% to 70% to 80% to 99% of the biochar particles in the batch have same modified or customized characteristic, e.g., deleterious pore surface materials mitigated, pore surface modified to provide beneficial surface, pore volume containing beneficial additives.

Accordingly, the ability to product large quantities of biochar having a high level of consistency, predictability and uniformity, provides numerous advantages in both large and small agricultural applications, among other things. For example, the ability to provide large quantities of biochar having predetermined and generally uniform properties will find applications in large scale agriculture applications. Thus, treated biochar batches from about 100 lbs up to 50,000+lbs and between may have treated biochar particles with predetermined, uniform properties.

As the treated biochar batches are made up of individual biochar particles, when referring to uniformity of such batches it is understood that these batches are made up of tens and hundreds of thousands of particles. Uniformity is thus based upon a sampling and testing method that statistically establishes a level of certainty that the particles in the batch have the desired uniformity.

Thus, when referring to a treated batch of biochar as being "completely uniform" or having "complete uniformity" it means that at least about 99% (e.g., two nines) of all particles in the batch have at least one or more property or feature that is the same. When a treated batch of biochar is referred to as "substantially uniform" or having "substantial uniformity" it means that at least about 95% of all particles in the batch have at least one or more property or feature that is the same. When a treated batch of biochar is referred to as "essentially uniform" or having "essential uniformity" it means that at least about 80% of all particles in the batch have at least one or more property or feature that is the same. The batches can have less than 25%, 20% to 80%, and 80% or more particles in the batch that have at least one or more property or feature that is the same. Further, the batches can have less than 25%, 20% to 80%, and 80% or more particles in the batch that have at one, two, three, four, or all properties or features that are the same.

D. Applications

Generally, treated biochar of the present inventions can be used throughout the world, in numerous soil types, agricultural applications, horticultural, large and small scale farming, organic farming, and in a variety of soil management applications and systems, and combinations and variations of these. In fact, this particular solution provides the capability to custom-manufacture biochar for a particular climate, environment, geographical area, soil type, or application by more precisely controlling key characteristics.

Examples of these applications include for example, use in acidic and highly weathered tropical field soils, use in temperate soils of higher fertility, use in large commercial applications, use for the production of large scale crops such as, soybean, corn, sugarcane and rice, in forestry applications, for golf courses (e.g., greens, fairways), for general purpose turf grasses, wine grapes, table grapes, raisin grapes, fruit and nut trees, ground fruits (e.g., strawberries, blueberries, blackberries), row crops (e.g., tomatoes, celery, lettuce, leafy greens), root crops (e.g., tubers, potatoes, beets, carrots), mushrooms, and combinations and variations of these.

Treated biochars and agriculture practices and methods, provide for improved soil structure, increased water retention capability, increased water holding ability of the soil over time, reduced runoff or leaching, increased holding ability for nutrients, increase holding of nutrients over time, and combinations and variations of these, and other features that relate to the increased holding and retention features and soil aggregation of the present biochars and processes. It further being understood that in addition to nutrients, other material additives, (e.g., herbicide, pesticide), can be utilized and benefit from the increased holding and retention capacities of the present biochars and methods.

Treated biochar may also be used in other applications, for example, such mixing with manure in holding ponds to potentially reduce gaseous nitrogen losses, soil remedial (for example absorption and capture of pesticide, contaminates, heavy metals, or other undesirable, disadvantageous soil components), ground water remediation, other bioremediations, storm water runoff remediation, mine remediation, mercury remediation and as a cattle or poultry feed additive.

Further, the present invention could be used to clean and/or infiltrate the pores of biochar with a variety of substances, for a number of purposes, including but not limited to, infiltrating the pores of biochar with nutrients, vitamins, drugs and/or other supplements, or a combination of any of the foregoing, for consumption by either humans and/or animals. The treated biochar may also be applied to animal pens, bedding, and/or other areas where animal waste is present to reduce odor and emission of unpleasant or undesirable vapors. Furthermore it may be applied to compost piles to reduce odor, emissions, and temperature to enable the use of the food waste and animal feed in composting. Biochar can also be applied to areas where fertilizer or pesticide runoff is occurring to slow or inhibit leaching and runoff. The biochar may also be treated with additives which make it easier to dispense or apply, such as non-toxic oils, anti-clumping/binding additives, surface drying agents, or other materials.

Biochar may also be used in other applications, for example, such mixing with manure in holding ponds to among other things potentially reduce gaseous nitrogen losses, soil remedial (for example absorption and capture of pesticide, contaminates, heavy metals, or other undesirable, disadvantageous soil components), ground water remediation, other bioremediations, storm water runoff remediation, mine remediation, mercury remediation, and as a cattle or poultry feed additive.

In general, in the agricultural application of biochar to soil, the biochar should be located near the soil's surface in the root zone, or in or adjacent to the rhizosphere, where the bulk of nutrient cycling and uptake by plants takes place. Although benefits may be obtained from the application of biochar in layers above, below, in and combinations and variation of these, the root zone, for example during landscaping for carbon sequestration, or if using biochar for moisture management. Layering of biochar at various depths above, below, in and combinations and variation of these, the root zone, the surface, and combinations and variations of these, may also be employed. The biochar layers may have different predetermined properties for each layer, based upon, for example, the depth of the layer, soil type, geography, crop, climate and other factors.

Those skilled in the art will further recognize that the present invention can be used on any type of soil application, including, but not limited to, the following: crops, turf grasses, potted plants, flowering plants, annuals, perennials, evergreens and seedlings. By way of example, treated biochar may be incorporated into or around the root zone of a plant. As most trees, rows, and specialty crops extract large percentage of their water from the first twenty-four inches below the soil surface, the above applications will generally be effective incorporating the biochar around the root zone from the top surface of the soil and up to a depth of 24" below the top surface of the soil, depending on the plant type and species, or alternatively, within a 24" radius surrounding the roots regardless of root depth or proximity from the top surface of the soil. When the plant roots are closer to the surface, the incorporation of the biochar within the top 2-6" inches of the soil surface may also be effective. Greater depths are more beneficial for plants having larger root zones, such as trees.

In certain examples of biochar applications, the treated biochar can be applied in amounts (e.g., rates of addition as measured by weight of treated biochar per area of field) of from about 0.001 ton of treated biochar per acre to about 150 tons of treated biochar per acre, from about 2.5 tons of treated biochar per acre to about 100 tons of treated biochar per acre, and from about 5 tons of treated biochar per acre to about 70 tons of treated biochar per acre, although larger and smaller amounts may be used. Additional rates of from about ½ tons of treated biochar to about 10 tons of treated biochar may be used. For example, application rates of 1 ton of treated biochar was added per acre to a soil for a lettuce crop where the soil had a pH of about 7. In another example, about 3 tons per acre of treated biochar was added to soil for a strawberry crop. In these examples, the plants showed enhanced growth rates and yields.

Generally, for conventional field cropping systems, biochar can be preferably added using existing farm equipment and incorporated into existing farming operations. For example, treated biochar can be applied and incorporated together with lime, since lime is often applied as a fine solid, which must be well incorporated into soil. However, it is also contemplated that the examples of the present inventions may give rise to new equipment and utilizations based upon the features, performance and capabilities of the present inventions. Generally, treated biochar may be applied to fields, by way of example through the use of manure or compost spreaders, lime spreaders, plowing method (e.g., from hand hoes, animal draft plows, disc harrows, chisels, rotary hoes, etc.), large scale tillage equipment, including rotary tillers, mulch finishers, draw offset discs, and disc harrows (such as for example JOHN DEERE DH51, DH52F, PC10, RT22, and RC22). Treated biochar may also be applied by modified large scale nutrient applicators (such as, for example, JOHN DEERE 2410C, 2510H, 25105 Strip-Till Medium Residue Applicator), large scale draw dry spreaders (such as JOHN DEERE DN345), large scale no-till planters, large scale dry fertilizer sub-surface applicators, and liquid slurry surface or subsurface applicators. Similar, and various other types of large farming, and earth moving and manipulation equipment may be used to apply the treated biochar to the field, such as for example, drop spreaders or drills.

For example, treated biochar may be applied using banding techniques, which is an operation involving applying the biochar in a narrow band, using equipment that cuts the soil open, without disturbing the entire soil surface. Using this technique the biochar can be placed inside the soil while minimizing soil disturbance, making it possible to apply biochar after crop establishment, among other applications.

In other examples, treated biochar may be mixed with other soil amendments, or other materials, such as for example manure, sand, topsoil, compost, turf grass substrate, peat, peat moss, or lime before soil application, which are already scheduled or part of the existing operations, and in this manner by combining these steps (e.g., biochar application with existing application step) can improve efficiency by reducing the number of field operations required. In other examples, treated biochar can also be mixed with liquid, (e.g., liquid manures) and applied as a slurry. Finer biochar particles may be preferably used with this type of slurry application using existing application equipment, and dust problems associated with these finer particles may be mitigated, managed or eliminated.

In further examples, treated biochar can be top dressed on perennial pastures or other perennial vegetation, such as spaces between fruit trees in orchards. Treated biochar may also be applied with individual plants while transplanting or mixed with topsoil and other amendments while preparing raised beds. In forestry or similar operations where replanting of seedlings takes place, treated biochar can be applied by broadcasting (e.g., surface application) or incorporation over the entire planting area, it can be added in the planting holes, and combinations and variations of these. Before or after tree establishment, biochar could also be applied by traditional and subsurface banding or top-dressed over perennial vegetation in orchards, but care should be taken to minimize root damage and soil compaction.

In other examples of applications, treated biochar can be applied in trenches radiating out from the base of established trees ("radial trenching") or in holes dug at some distance from the base of the tree ("vertical mulching"); biochar could also potentially be applied to soil using "air excavation tools". These tools use pressurized air to deliver material, e.g., compost, under the soil surface and reduce compaction. Alternatively, the soil around tree roots can be excavated and treated biochar applied before covering with soil.

While, in some examples, particle size distribution of treated biochar materials may vary widely depending on the feedstock and the pyrolysis technique used to produce the biochar, uniformity if required or preferred, can be achieved by various milling and grinding techniques that may be employed during processing or during the distribution and application to soil. When smaller particles are utilized, and in particular for surface applications, care should be taken to apply the treated biochar in ways that minimize loss due to wind or water erosion.

Examples of the benefits of treated biochar on plant growth and in agricultural applications are demonstrated below in connection with FIGS. 18-25.

Figure 18:
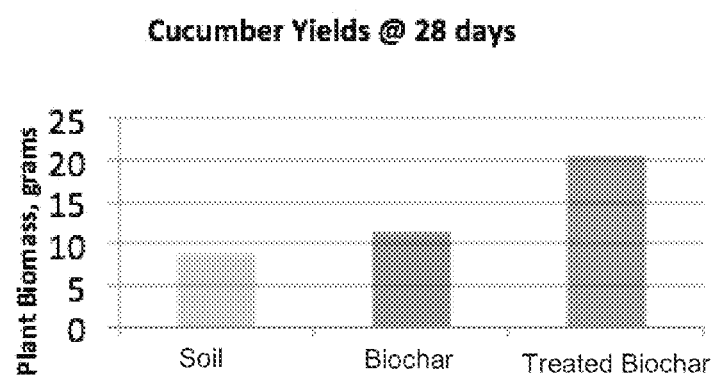
FIG. 18 is a chart showing the plant biomass of cucumber plants grown in standard soil, soil enhanced with raw biochar and soil enhanced with treated biochar.

FIG. 18 illustrates one example of the potential benefit of biochar and treated biochar to plant growth. FIG. 18 is a chart showing the plant biomass, measured in grams, of cucumber plants after twenty-eight days of growth in one soil type and in that soil type with biochar and treated biochar added to the soil. As illustrated, the soil with the treated biochar yielded a cucumber plant over 2× the size, in weight, to the plant grown in the soil. The additional of raw biochar also showed a benefit to plant growth, but not to the same degree as the soil with the treated biochar.

Figure 19A:
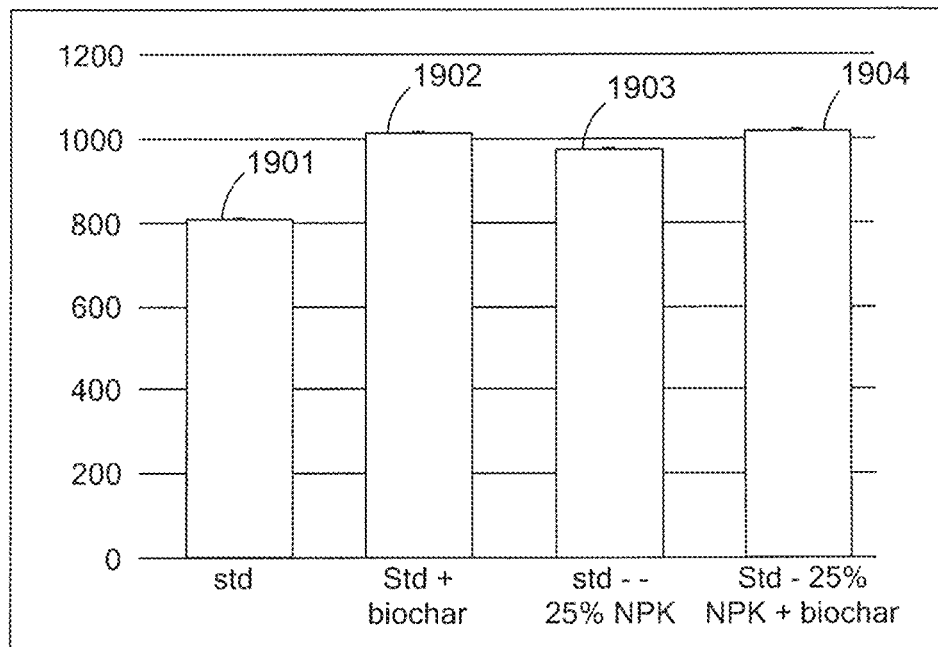
FIG. 19A is a chart showing results for a celery shoot biomass yield results from a field trial incorporating treatments without and with biochar treated in accordance with the present inventions.
Figure 19B:
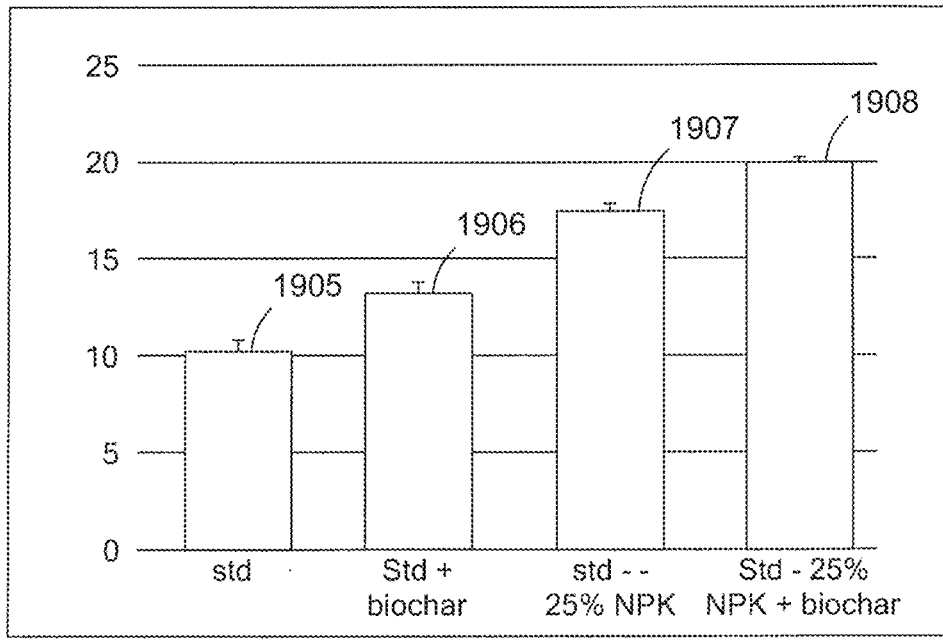
FIG. 19B is a chart showing results of root biomass growth for a celery field trial incorporating treatments without and with biochar in accordance with the present inventions.

Turning to FIGS. 19A and 19B there are provided charts showing the significant difference between, and improvements over, the absence of biochar and of various examples of biochar. Thus, biochar increases biomass yields by 25% using the growers' standard, typical, nitrogen and water programs. FIG. 19A shows celery sheet biomass yields in grams, with the standard 1901, standard plus biochar 1902, standard plus 25% NPK 1903, and standard plus 25% NPK and biochar 1904. FIG. 19B shows celery root biomass in grams, with the standard 1905, standard plus biochar 1906, standard plus 25% NPK 1907, and standard plus 25% NPK and biochar 1908.

Figure 20A:
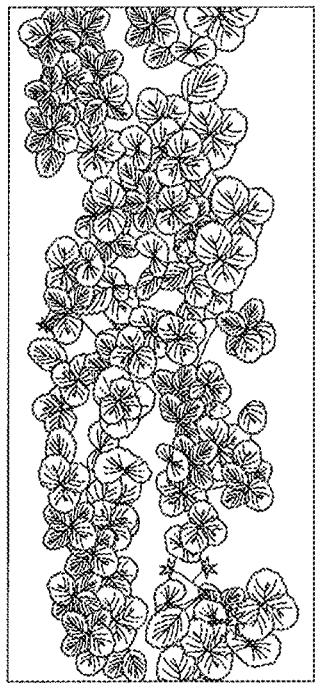
FIG. 20A is a pictorial of a photograph showing the results of a strawberry trial in accordance with growers' standard conditions.
Figure 20B:
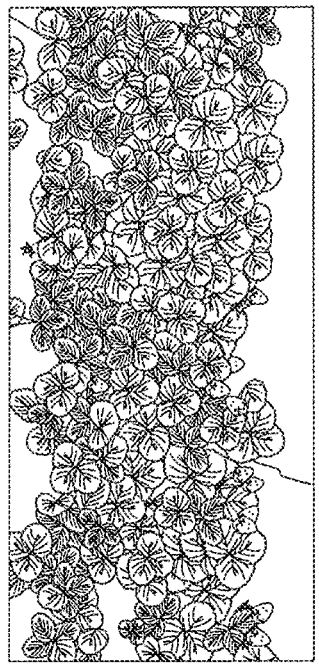
FIG. 20B is a pictorial of a photograph showing the results of a strawberry trial using a growers' standard conditions in which biochar produced in accordance with the present inventions was added at 3 ton/acre to the soil.
Figure 20D:
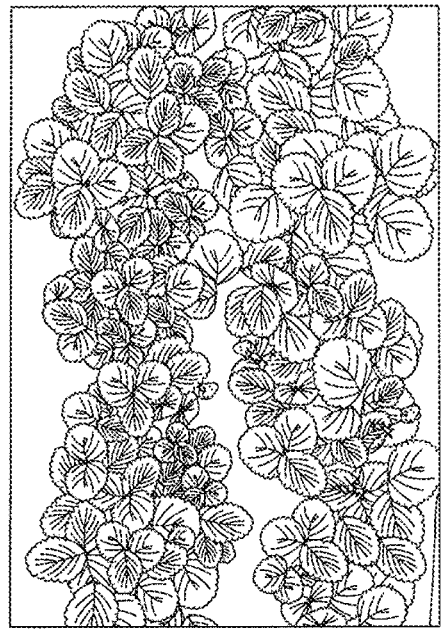
FIG. 20D is a pictorial of a photograph showing the results of a strawberry trial using biochar in accordance with the present inventions with a reduced water application rate.
Figure 20C:
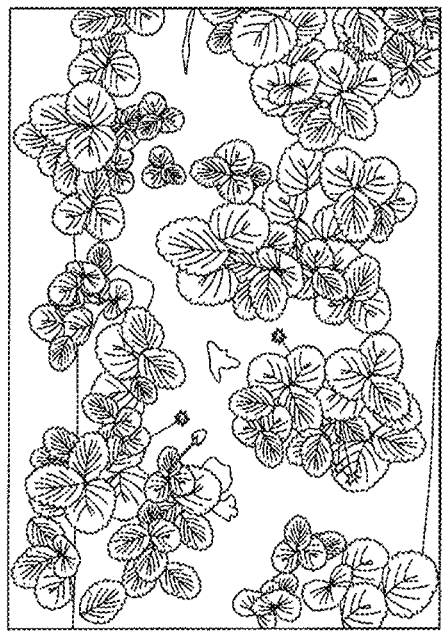
FIG. 20C is a pictorial of a photograph showing the results of a strawberry trial in accordance with a growers' standard at a reduced water application rate.
Figure 21:
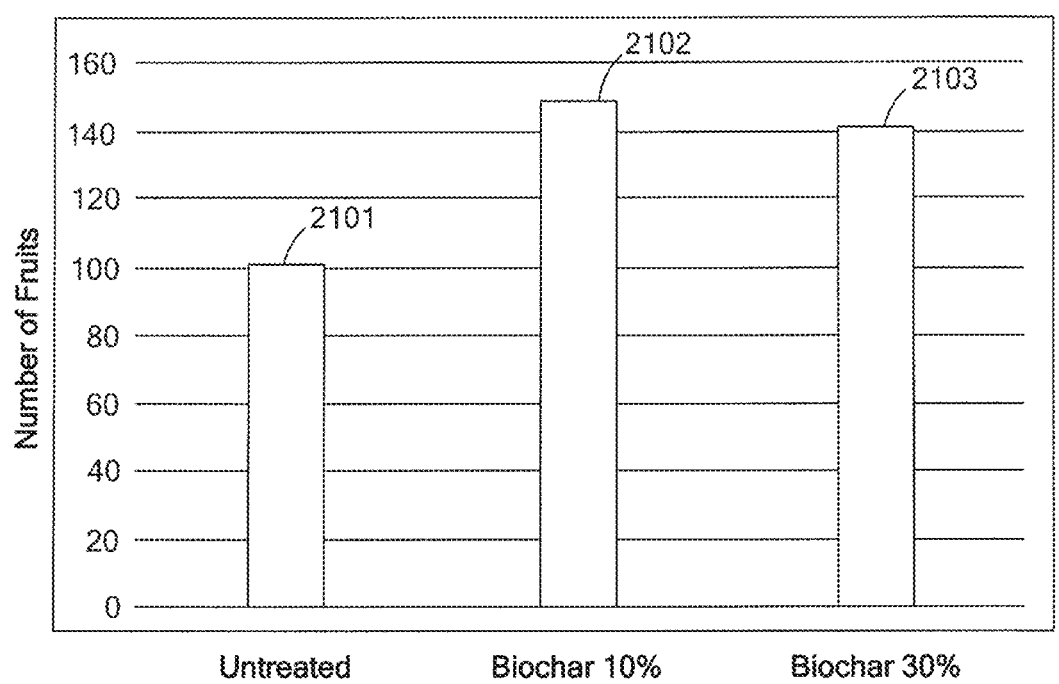
FIG. 21 is a chart showing the yield of fruit for an untreated soil compared to two applications of biochar treated in accordance with the present inventions.

Turning to FIG. 20A showing a pictorial of a photograph of strawberry plants under nitrogen and water deficiencies, when compared against strawberry plants grown under the same deficiencies, but with the utilization of treated biochar. The strawberries grown under these deficiencies with biochar are substantially larger, having greater biomass, as seen in FIG. 20B. Similarly, turning to FIGS. 20C (no biochar) and 20D (with treated biochar) show that strawberry plants grown under 40% reduced water conditions with biochar do substantially better, e.g., more biomass, etc., than those without. For example, FIG. 21 shows the increase in the number of fruits present in strawberries from untreated 2101, compared to biochar at 10% 2102, and biochar at 30% 2103.

Figure 22:
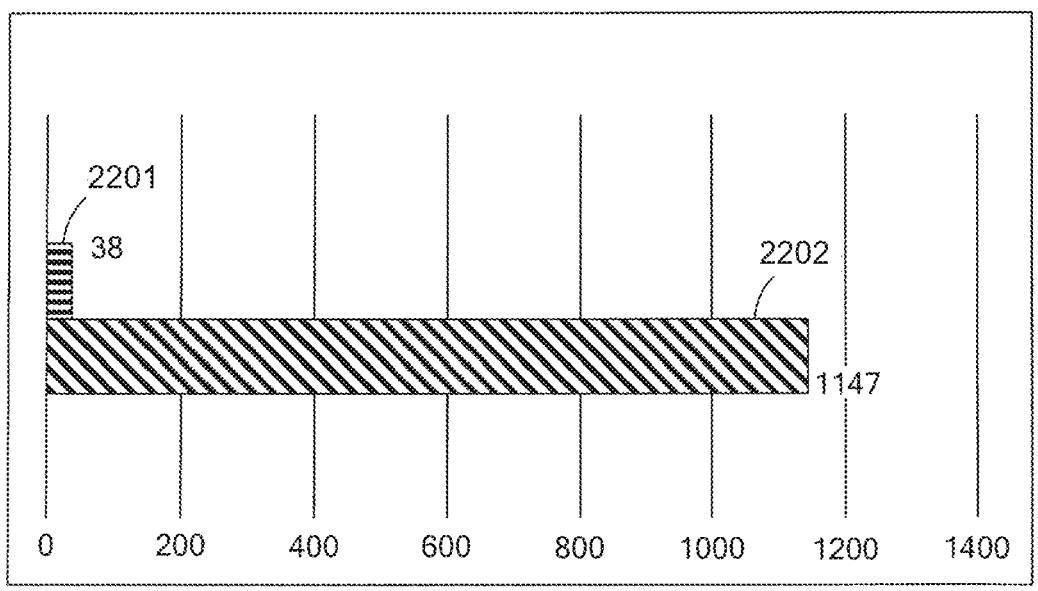
FIG. 22 is a chart showing the decrease in soil fungal species *Sclerotinia* and *Botrytis* Necrotrophic count in soils treated with biochar produced in accordance with the present invention.

FIG. 22 provides a chart showing an example of the treated biochar decreasing *Sclerotinia* and *Botrytis* necrotrophic fungal plant pathogens. Thus, the pathogen count for soil with biochar 2201 (count of 38) is substantially lower than the count 2202 (count 1147) without biochar. Because *Sclerotinia* and *Botrytis* can cut harvests by typically 30% to 40%, but may be as high as 100%, when mitigating these pathogens, using treated biochar has the ability to substantially increase harvests.

Figure 23:
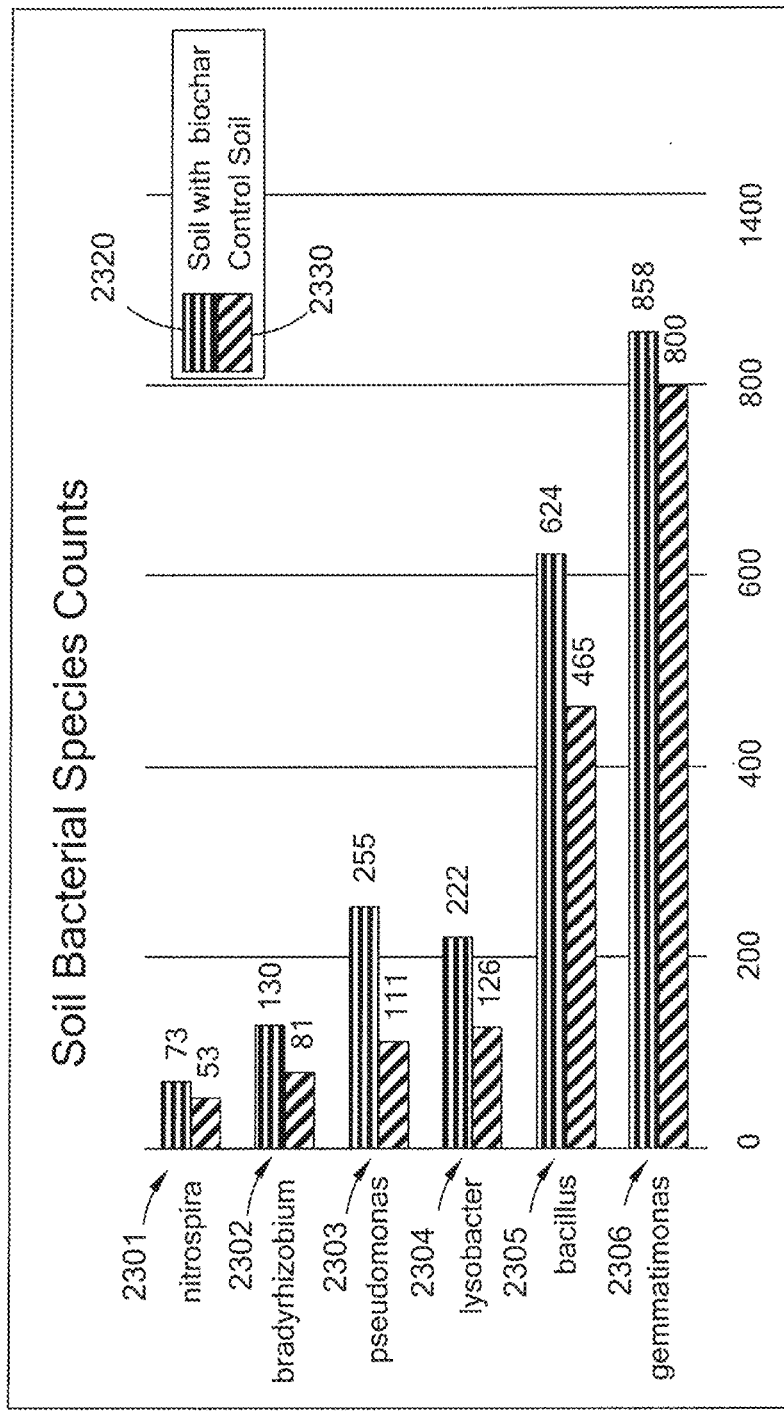
FIG. 23 is a chart comparing the soil bacterial species count for a control soil compared to a soil incorporating biochar produced in accordance with the present inventions.

FIG. 23 shows another example of biochar increasing the amount of beneficial bacterial species. Thus, the soil with biochar is shown with cross hatching 2320, and the control sample with cross hatching 2330. Thus, as seen in FIG. 23, *Nitrospira* 2301, *Bradyrhizobium* 2302, *Pseudomonas* 2303, *Lysobacter* 2304, *Bacillus* 2305, *Gemmatimonas* 2306 all show increases with the use of biochar.

Figure 24:
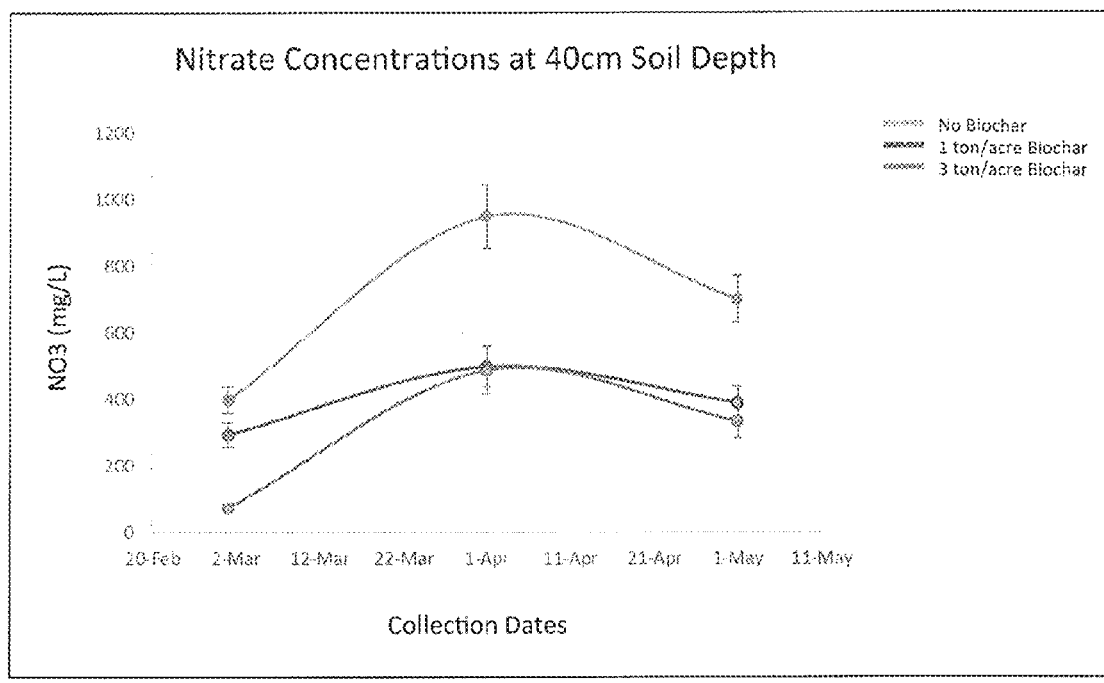
FIG. 24 is a chart showing nutrient levels comparing examples of the present invention, compared to untreated soil, in accordance with the present inventions.

Turning to FIG. 24 there is shown a chart showing the amount of nutrient (nitrogen in the form of NO3) that has leached below the root level and thus, is no longer useable or beneficial to the plants in the field. Thus, as illustrated in FIG. 24, samples of soil at 40 cm depths were measured for nitrates over time. The soils having 1 ton/acre (of the present biochar) and 3 ton/acre (of the present biochar) shows that substantially less nutrients were leached (e.g., lost) from the root zone into lower levels of the soil.

Thus, farming using the present biochars can provide for, where a 100 acre or more field, a 200 acre or more field, a 500 acre or more field, a 1,000 acre or more field, and a 10,000 acre or more field, retains over time, e.g., a growing cycle, or set period, (e.g., about 3 to 9 months, or more depending on climate, crop and location) a substantial amount of the added nutrients, e.g., fertilizer, in the root zone, and an amount greater than untreated fields, or fields treated with prior biochar. Similarly, these methods can reduce leaching of nutrients from the root zone or other layers of the soil by at least a substantial amount and an amount greater than untreated fields or fields treated with prior biochars, over a growing period or set time. Thus, the present invention provides the ability to greatly reduce the amount of nutrients that migrate to unneeded and undesirable locations, e.g., runoff. It being understood that longer and shorter periods of time may be used for these analysis and measurements, and that larger and smaller agriculture activities can benefit from and utilize these practices.

Figure 25:
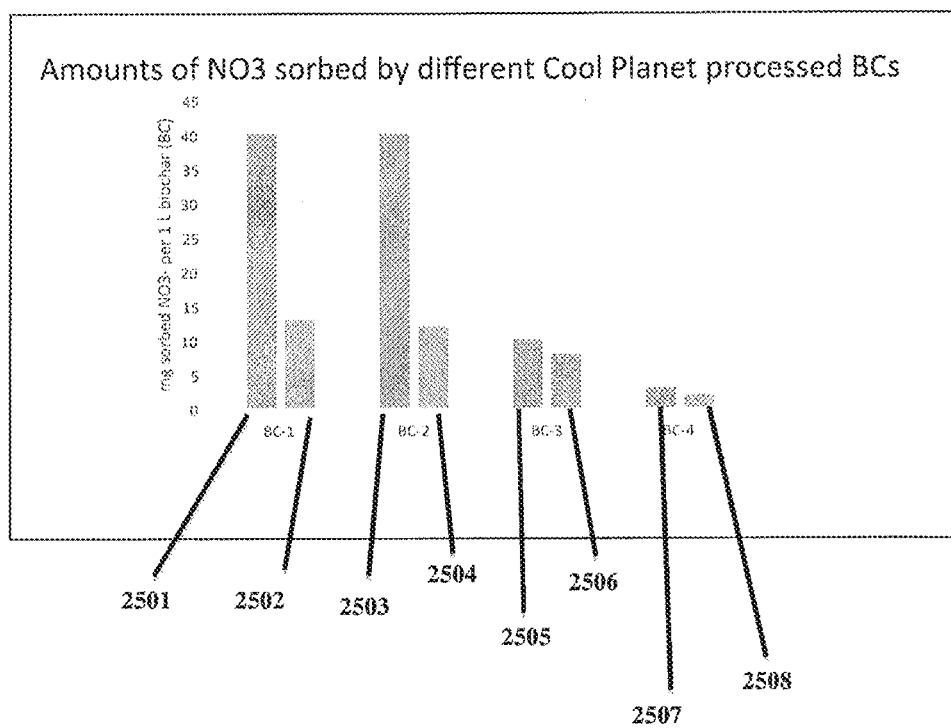
FIG. 25 is a chart showing the increase in nutrient retention for examples of treatments and biochars in accordance with the present inventions.

Turning to FIG. 25 there is shown amount of NO3 that can be absorbed by utilizing treated biochar. Thus, biochar BC-1 untreated 2502, treated 2501, shows about a 4× increase, biochar BC-2 untreated 2504, treated 2503, shows greater than a 4× increase, biochar BC-3 untreated 2506, treated 2505, shows about an increase, and biochar BC-4 untreated 2508, treated 2507 shows an increase.

E. Examples of Various Implementations

The following examples are provided to illustrate various examples of, among other things, porous carbonaceous structures, materials and compositions, methods to treat, process and affect the properties of those structures, materials and compositions, and applications for these structures, material and compositions. These examples are for illustrative purposes, and should not be viewed as, and do not otherwise limit the scope of the present inventions.

Example 1

By way of illustration, 2000 pounds of a starting biochar are processed in the system of FIG. 5. The starting biochar is made up a biochar obtained from coconut shells (pH 7.4). The biochars are vacuum infiltrated with 0.23 molar acetic acid, and held for an infiltration time of 5 minutes. The biochar is then vacuum infiltrated with a bacteria solution and held for an infiltration time of 5 minutes. The infiltrated biochar is dried to less than 25% moisture, to provide a treated biochar having a substantially uniform pH of 6.8, with less than 1% of particles having a pH greater than 7.5. The acid infiltration process and drying may also reduce phytotoxins from the starting material biochar particles, and their pore morphology and their pore surfaces. Thus, the pore surfaces may be substantially free from any phytotoxic materials.

Example 2

Figure 26C:
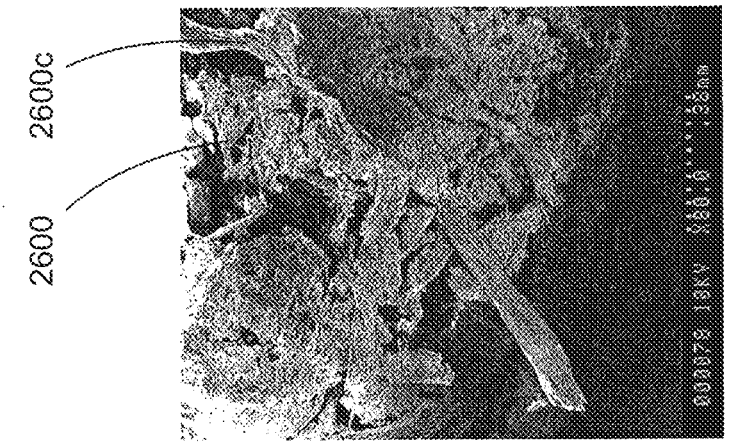
FIG. 26C is a SEM (10 KV×80 0.38 mm) of a biochar pore morphology and roots in accordance with the present inventions.
Figure 26B:
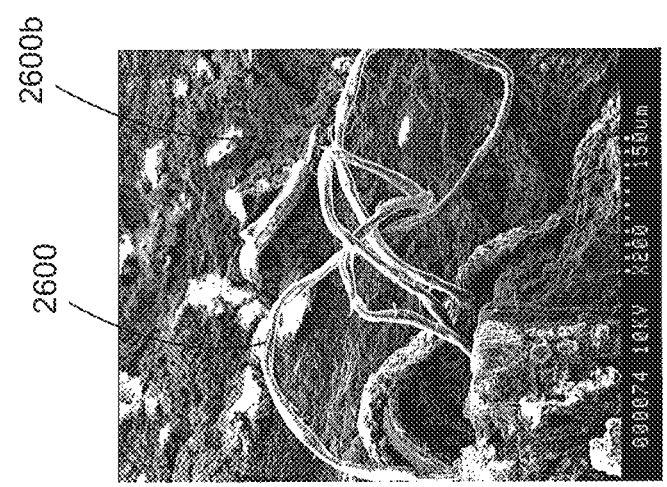
FIG. 26B is an SEM (10 KV×200 150 J·lm) of a biochar pore morphology and roots in accordance with the present invention.
Figure 26A:
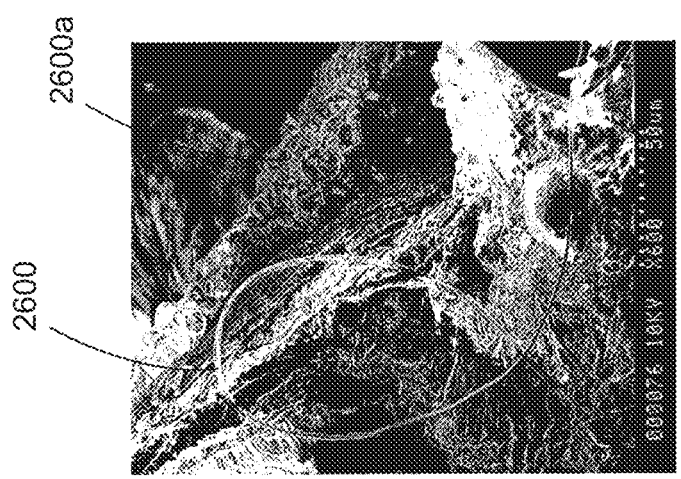
FIG. 26A is an SEM (10 KV×600 50 J·lm) of a biochar pore morphology and roots in accordance with the present invention.

FIGS. 26A, 26B, 26C show scanning electron photomicrographs (SEMs) of treated biochar with a uniform pH at or below 7 that has had lettuce micro root growth 2600a, 2600b, 2600c throughout and into the biochar pore morphology 2600. Root hair or micro root growth that is integral with the pore morphology provides water and nutrient uptake. The growth of the root hairs into and throughout the pore morphology is one of the many advantages and benefits of biochars in the soil and may promote plant growth and increase yields. The pockets of gas and water space in the biochar pores may allow for both gas exchange and nutrient uptake as well as plant-microbial signaling to occur.

Example 3

The process of Example 1 is performed using organic (OMRI (Organic Materials Review Institute) or other certification body) acetic acid, e.g., vinegar, instead of an industrial acid, and only fresh water is used, e.g., no grey water, no recycled or reprocessed waste water is used. The treated biochar may be a certified organic product that can be used in organic farming and the production of organic crops.

Example 4

Figure 27:
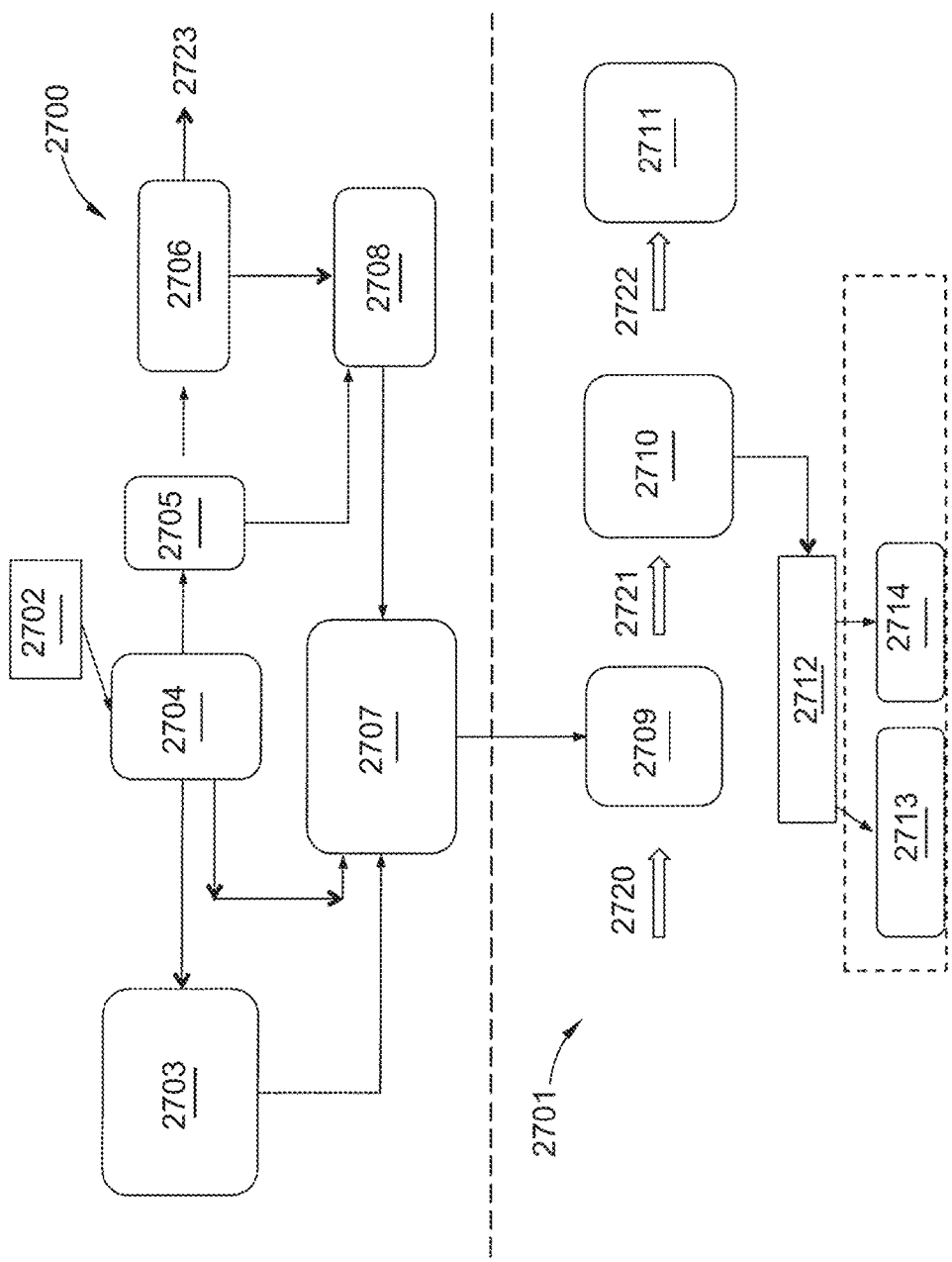
FIG. 27 is a schematic flow diagram of one example of an implementation of the invention.

Turning to FIG. 27 there is provided a schematic flow chart of one example of a process for making biochar batches having predetermined and uniform properties. The process has a fluid system 2700 and a solids system 2701. The fluid system 2700 has a source of city water 2702, an acetic system 2703, a granular activated carbon bed 2704, a R/O (reverse osmosis) Deionized water system 2705, a compost extraction system 2706, an inoculant preparation system 2708, infiltrant makeup and delivery system 2707 for infiltrant containing acid and inoculant. The dry system 2701 combines the infiltrant with the starting biochar. The dry system 2701 has a source of starting biochar 2720, a vacuum infiltration system 2709, pH adjusted and infiltrated biochar 2721, a centrifugal dewatering system 2710, dewatered treated biochar 2722, packaging and post processing system 2711. Fines and waste from the centrifugal dewatering system 2710 may be processed by a belt press 2712 to provide for disposal or sale permeate 2713, and cake 2714.

Example 5

In operation, in the process of Example 4, the vacuum tumbler is used in the vacuum infiltration system 2709 to draw water, acid and microbial inoculant into the starting biochar pores (preferably into the macro-, meso- and micro pores) by placing the biochar under vacuum and tumbling it. It is theorized that water renders the pore surfaces hydrophilic, increasing water holding and nutrient retention capacities of the treated biochar. The dewatering step of the process of Example 4, removes excess water from the biochar. This dewatering step may also reduce or substantially removes the inorganic compounds such as sodium, magnesium, and calcium from the pores, e.g., the pore morphology. These compounds above certain concentrations can be toxic to soil microbes and plants, and contribute to the undesirably high pH seen with starting biochar. The process of Example 4, and in particular, the dewatering and the acid treatment, may serve to reduce the pH of the biochar from inside out. This reduction in pH can adjust the pH to a level that is more suitable for microbial and plant growth. The dewatering system 2710 may have the capability to reduce the moisture content of the treated biochar, e.g., infused and pH adjusted biochar, to moisture levels that may be more suitable for use in existing farm implements, with minimal or no modification to those farm implements. Typically, the moisture contents may be less than 10%.

Example 6

A treated biochar batch from the following process: (i) 2200 lbs of starting biochar; (ii) 0.8 molar acetic acid infiltration, at vacuum of 0.4 atm for vacuum hold time of 60 seconds; (iii) drying to moisture content of 20-30%; (iv) vacuum infiltration with inoculant containing compost liquid extract, at vacuum of 0.4 atm for vacuum hold time of 60 seconds; and (v) drying to moisture content of 20-30%.

Example 7

A treated biochar batch from the following process: (i) 10,000 lbs of starting biochar; (ii) 0.25 molar acetic acid infiltration, at vacuum of −8 psig for vacuum hold time of 5 minutes to yield a biochar with a pH of 6.5; (iii) drying to moisture content of 30%; (iv) vacuum infiltration with 65 gallons inoculant containing *Bacillus* spp, at vacuum of −8 psig for vacuum hold time of 5 minutes; and (v) drying to moisture content of 20%.

Example 8

A treated biochar batch from the following process: (i) 10,000 lbs of starting biochar; (ii) 0.25 molar acetic acid infiltration, at vacuum of −8 psig for vacuum hold time of 5 minutes to yield a biochar with a pH of 6.5; (iii) drying to moisture content of 30%; (iv) vacuum infiltration with 65 gallons inoculant containing *Bacillus* spp. ($10^4$ cfu/ml) bacteria known for rapid organic decomposition, at vacuum of −8 psig for vacuum hold time of 5 minutes; and (v) drying to moisture content of 20%.

The biochar was blended with 1000 cubic meters of compost and incubated for 30 days in covered aerated static piles. The *Bacillus* spp. colony count increased slightly rather than the expected rapid decomposition.

Example 9

A treated biochar batch from the following process: A sufficient amount of corn stovers were pyrolyzed at 400° C. to produce 700 kg of starting biochar. The resulting biochar exhibited a mean surface area of 250 m$^2$/g with 50% macroporosity. Half of the resulting biochar was pyrolyzed in a second step to 750° C. to produce a biochar with a mean surface area of 475 m$^2$/g with 37% macroporosity. The biochar with the greater macroporosity was exposed to a solution of ammonium phosphate nitrate and potassium sulfate in vacuum system at 0.7 atm. The fertilizer impregnated biochar and the high surface biochar were mixed in a 50:50 v/v ratio and applied on sandy soil.

Example 10

A treated biochar batch from the following process: (i) 4,000 lbs of starting mixed feedstock biochar; (ii) 0.8 molar phosphoric acid and inoculant containing a microbial fertilizer mixture infiltration, at vacuum of 0.5 atm for vacuum hold time of 2 min; and (iii) drying to moisture content of 20%.

Example 11

A treated coconut based biochar batch having the following essentially uniform properties: (i) pH of 6.7; (ii) particle size of about 5 mm; (iii) processed in accordance with the present invention and dried to 15% moisture or less; and (iv) applied to a soil subsurface using a drill spreader in bands 2-3 inches adjacent to transplant lines and 2-6 inches below the soil surface at a rate of 1 cubic yard/acre for an celery crop.

Example 12

A treated coconut based biochar batch having the following essentially uniform properties: (i) pH of 6.7; (ii) particle size of about 5 mm; and (iii) processed in accordance with the present invention and dried to 15% moisture or less; and (iv) applied to a soil subsurface using a drill spreader in bands 2-3 inches adjacent to transplant lines and 2-6 inches below the soil surface at a rate of 6 cubic yard/acre for a strawberry crop.

Example 13

A treated biochar batch of mixed coconut and pine feedstock: (i) treated to a final pH of 6.8; (ii) 20% moisture; (iii) total porosity of 0.38 cm$^3$/cm$^3$; (iv) inoculant loading 25,000 micrograms of fungi tog of biochar; and (v) non-phytotoxic organic compound of less than 1% (weight percent).

Example 14

A treated biochar batch originating from pine having the following substantially uniform properties: (i) pH of 6.5; (ii) particle size 5 mm to 8 mm; (iii) 20% moisture; (iv) total porosity of 0.41 cm$^3$/cm$^3$; (v) inoculant loading 11,000 micrograms of fungi and 80,000 micrograms of bacteria to 1 g of biochar, with an inoculant of compost liquid; and (vi) stored in a warehouse at ambient conditions of 75 degrees Fahrenheit for 8 weeks has at time of application 9,000 micrograms of fungi and 90,000 micrograms of bacteria to 1 g of biochar.

Example 15

A treated biochar batch from the following process: (i) 6m3 of starting biochar; (ii) acetic acid solution with pH=3.0 is infiltrated at vacuum of −8 psig for vacuum hold time of 5 minutes; (ii) A second vacuum filtration step using a worm casing bio extract containing fungi and microbes is used to modify the biochar; drying to moisture content of 20%; and stored in ambient conditions for 12 months and appears to still retain substantially the same microbial activity as before the storage.

Example 16

Turning to FIGS. 4, 4a and 4b, raw biochar 402 pH>7.0 is treated with pH=7.0 water via vacuum infiltration 405.

After vacuum treatment for 2 minutes the biochar moisture is adjusted in step 407 and then processed for shipment 412.

Example 17

Treated biochars may include a biochar skeletal framework and a microbial community embedded on the surface of this skeletal framework. The microbial community may also be on the surface of the biochar, although there is substantially greater area within the pores than on the surface. Additionally, the pores protect, e.g., hold on to, shield, the microbial community preventing it from being inadvertently removed. The biochar can be derived from the pyrolysis of cellulosic or lignocellulosic containing feedstock to create the skeletal framework upon which the microbial community is contained in, embedded in, on the surface of and combinations and variations of these. This biochar can be useful as a soil amendment, soil modifier, soil growth agent, soil conditioner, plant growth enhancer, plant booster, vegetative plant enhancer, reproductive plant enhancer, flowering plant enhancer or plant root enhancer.

The biochar skeletal frame element can be derived from the pyrolysis of cellulosic or lignocellulosic containing material in an oxygen starved environmental temperatures typically ranging from 350° C. to 700° C. This process serves to create a porous cellular structure which provides a skeletal framework for the microbial element. The cellulosic or lignocellulosic containing material is feedstock typically biomass and includes any material derived or readily obtained from plant sources. Such material can include without limitation: (i) plant products such as bark, leaves, tree branches, tree stumps, hardwood chips, softwood chips, grape pumice, sugarcane bagasse, switchgrass; and (ii) pellet material such as grass, wood and hay pellets, crop products such as corn, wheat and kenaf. This term may also include seeds such as vegetable seeds, sunflower seeds, fruit seeds, and legume seeds. The feedstock can also include: (i) waste products including animal manure such as poultry derived waste; (ii) commercial or recycled material including plastic, paper, paper pulp, cardboard, sawdust, timber residue, wood shavings and cloth; (iii) municipal waste including sewage waste; (iv) agricultural waste such as coconut shells, pecan shells, almond shells, coffee grounds; and (v) agricultural feed products such as rice straw, wheat straw, rice hulls, corn stover, corn straw, and corn cob.

Example 18

Figure 28:
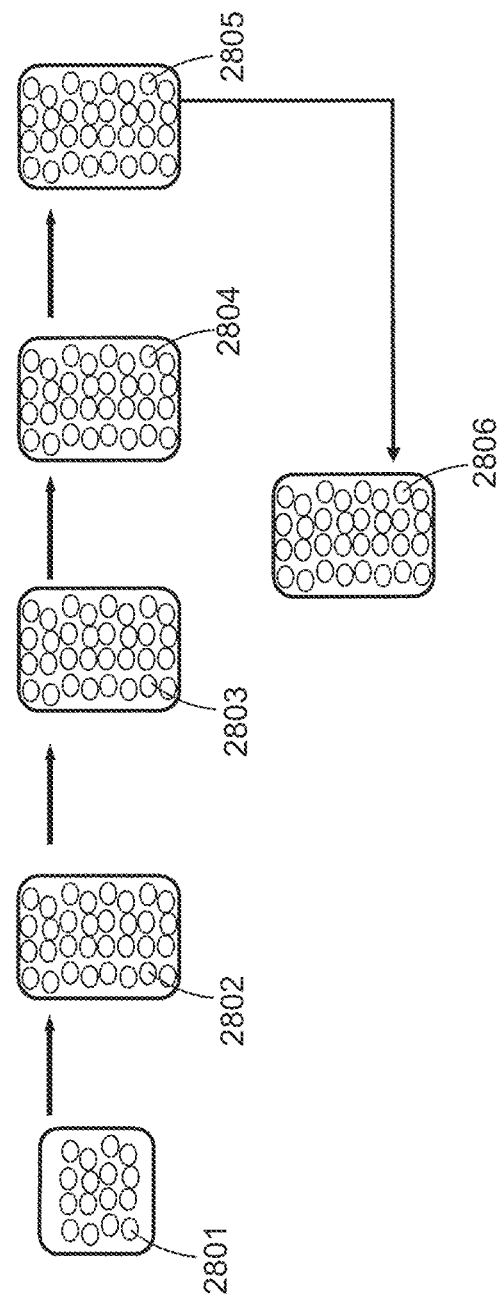
FIG. 28 is schematic flow diagram of another example of an implementation of the invention.

One example of a method for making a treated biochar uses a system shown in FIG. 28. A raw biochar 2801 is introduced into a reactor 2802 (Reactor 1) that adjusts pH of the incoming biochar. This adjustment may be made through acidification of the biochar with inorganic or organic acids. Inorganic acids may include nitric, sulfuric, and phosphoric acids. Organic acids may include formic or acetic acids. After the acidification, the biochar is dewatered in a reactor 2803 (Reactor 2), such as centrifugal machine. Following the water removal is the inoculation step in reactor 2804 (Reactor 3), which introduces microbes, preferably in the preferred ratios and ranges set forth in this specifications, however other ratios and ranges may be used. This step may be accomplished by a variety of methods, including a method that introduces vacuum to the entire reactor and then exposes the biochar to the inoculum.

After the bio-inoculation step, dewatering step may occur in reactor 2805 (in Reactor 4), to bring the biochar moisture levels to desired levels for transport, use, and both. The infiltrated biochar is then bagged by proposing equipment 2806.

Example 19

An example of a lettuce field application in sandy loam soil can be as follows. Biochar: pH 7.82, total porosity 0.30 $cm^3/cm^3$, impregnation capacity 0.30 $cm^3/cm^3$, fixed carbon 75%, residual organic compounds 17%. The total fungi to total bacteria ratio is measured as 0.62. A randomized block design within an area of approximately 0.25 acres has the following treatments: (i) No biochar application at 100% growers' standard N application rate; No biochar application at 50% growers' standard N application rate; No biochar application at 25% growers' standard N application rate; Biochar application at 100% growers' standard N application rate; Biochar application at 50% growers' standard N application rate; and, Biochar application at 25% growers' standard N application rate.

The three nitrogen fertilizer application rates are 100 lbs nitrogen/acre, 50 lbs nitrogen/acre, and 25 lbs nitrogen/acre. A drip irrigation system with direct injection of water soluble nitrogen fertilizer along each bed is set up. The application rate of biochar is 30% v/v within each plot measuring 5 ft×3 ft×0.33 ft. Special research lysimeters are installed at two different soil depths (4 inches and 8 inches). Seven sets of lysimeters are located at different reps of the six treatments.

Soil solution samples are collected from the lysimeters along with leaf tissue samples, soil samples, and water source samples at specific time points during the growing cycle. Ten romaine green lettuce transplants are placed in each control and experimental plots along each side of the drip line tapes.

Sample Collection Timepoints—Prior to ground preparation and biochar application of the present invention, soil samples (4) and water source sample (1) are taken. Soil samples (4) are taken again 10-15 days after biochar application of the instant invention and (4) after harvest to check physical and chemical properties. There are six lysimeter sampling periods, one prior to first Nitrogen application and two after each Nitrogen application to determine nutrient holding capacity against leaching and contribution of invention biochar. Last samplings are coordinated right before harvest. Each of these sampling periods will encompass soil solution samples from 2 lysimeters of each monitoring set.

Two fertigation events one month apart inject 100, 50, or 25 pounds of soluble nitrate fertilizer into the drip lines. During the first fertigation event, however, the nitrate concentrations from the drip lines for the 50 lbs of nitrate fertilizer treatment (50N) show concentrations similar to the 100 lbs of nitrate fertilizer treatment (100N). The large dosage of nitrate fertilizers in the 100N and 50N treatments is reflected in the nitrate concentrations at the 4 inch and 8 inch soil depths.

In each of the biochar treatments, total soil organic matter increases significantly over controls. Analysis of biochar after inoculation with compost liquid extract shows high levels of total and active bacteria and fungi (data not shown). After the first fertigation event, total soil nitrogen begins to increase in both the control and treatments. Nitrogen concentrations, however, in the biochar treatments are greater than the controls, indicating an increase in nutrient retention. By the end of the experiment, total soil nitrogen concentrations in the biochar treatments are at least 15% greater than the concentrations found in the control treatments. In the 25N biochar treatment, the increase in total soil nitrogen concentration over control treatments is over 20%.

Leaf samples collected from the biochar and control treatments at mid-harvest are analyzed for nitrogen and phosphorous content. Biochar treatments show higher percentages of both nitrogen and phosphorous in the leaves compared to control treatments. Biochar in the 50N treatments show a greater difference to controls than in the 100N and 25N treatments. Increase plant uptake of nitrogen and phosphorous in the biochar 50N treatment compared to the control treatments is attributed to the increase availability of nitrates in the biochar soil.

Biochar treatments increase the total yields of lettuce plants at the time of harvest. In the 50N treatments, biochar increases yield by more than 75% over controls. Reduction in nitrogen fertilizer rates exhibit a positive effect on control plants.

In the 25N control treatments, lettuce yields increase by more than 25% when compared to 100N control treatments. Although 100N is the standard fertilization rate for commercial lettuce growers, the soil nitrate concentrations from the lysimeter data show sufficient nitrate concentrations in the 25N treatments. At the lower nitrogen fertilization rates, 50N and 25N, biochar treatments increased nutrient uptake and utilization, leading to increased lettuce yields.

Thus, in the foregoing example, the application of biochar can increase nutrient utilization and uptake. Lettuce plants grown in 30% v/v biochar amended soil can show increase percentages of nitrogen and phosphorous, in addition to a significant increase in plant yields. Despite reduced nitrogen fertilization rates, the ability of biochar to retain more nutrients in the rhizosphere can contribute to an increase in plant biomass. The biochar may also able to promote bacterial and fungal species beneficial for nutrient mobilization and uptake.

Example 20

The following sets out one example of characteristics of a treated biochar. It being understood that other features and broader, and different, ranges of the listed features are contemplated, and in some applications may be preferred: (i) Bulk density of about 0.04 to about 0.75 g/cm$^3$; solid density of about 0.3 to about 1,200 g/cm$^3$; impregnation capacity of about 0.2 to 0.45 cm$^3$/cm$^3$; particle sizes distributions of 95% or more of a batch being from 500 microns to 100 microns in size. Particle surface area of about 100 to about 900 m$^2$/g. Total porosity of about 0.2 to about 0.45 cm$^3$/cm$^3$. Ash content of about 2% to about 25%. Organic compounds from about 0% to about 35%. Fixed carbon content from about 55% to about 85%. Water content from about 10% to about 45% (lower moisture may be preferred in product as shipped and handled by farm implements).

As set forth above, the treated biochar of the present invention may be used in various agriculture activities, and the fields of edaphology and pedology, as well as other activities and in other fields. Additionally, the treated biochar may be used, for example, with: farming systems and technologies, operations or activities that may be developed in the future; and with such existing systems, operations or activities which may be modified, in-part, based on the teachings of this specification. Further, the various treated biochar and treatment processes set forth in this specification may be used with each other in different and various combinations. Thus, for example, the processes and resulting biochar compositions provided in the various examples provided in this specification may be used with each other; and the scope of protection afforded the present inventions should not be limited to any particular example, process, configuration, application or arrangement that is set forth in a particular example or figure.

Although this specification focuses on agriculture, soil modification and plant growth, it should be understood that the materials, compositions, structures, apparatus, methods, and systems, taught and disclosed herein, may have applications and uses for many other activities in addition to agriculture for example, as filters, additives, and in remediation activities, among other things.

It being understood that one or more of these may be preferred for one application, and another of these may be preferred for a different application. Thus, these are only a general list of preferred features and are not required, necessary and may not be preferred in all applications and uses.

It is noted that there is no requirement to provide or address the theory underlying the novel and groundbreaking functionality, performance or other beneficial features and properties that are the subject of, or associated with, embodiments of the present inventions. Nevertheless, to the extent that various theories are provided in this specification to further advance the art in this important area. These theories put forth in this specification, and unless expressly stated otherwise, in no way limit, restrict or narrow the scope of protection to be afforded the claimed inventions. These theories many not be required or practiced to utilize the present inventions. It is further understood that the present inventions may lead to new, and heretofore unknown theories to explain the functionality, performance or other beneficial features and properties that are the subject of, or associated with, embodiments of the methods, articles, materials, and devices of the present inventions; and such later developed theories shall not limit the scope of protection afforded the present inventions.

Those skilled in the art will recognize that there are other methods that may be used to treat biochar in a manner that forces the infusion of liquids into the pores of the biochar without departing from the scope of the invention. The foregoing description of implementations has been presented for purposes of illustration and description. It is not exhaustive and does not limit the claimed inventions to the precise form disclosed. Modifications and variations are possible in light of the above description or may be acquired from practicing the invention. The claims and their equivalents define the scope of the invention.

We claim:

1. A method for treating a porous carbonaceous material having pores, the method comprising the steps of:
   placing the porous carbonaceous material in a tank, where the porous carbonaceous material is made of particles having a diameter greater than 0.037 mm;
   adding a solution to the tank, where the solution contains a surfactant; and
   mixing the solution with the porous carbonaceous material.

2. The method of claim 1 where the solution is a liquid solution containing 0.1-20% surfactant.

3. The method of claim 2 where the surfactant is a *yucca* extract.

4. The method of claim 2 where the solution further includes an additive.

5. The method of claim 4 where the additive is selected from the group consisting of water, liquid inorganic and organic compounds of different composition and polarity, water solutions of salts, water solutions of acids, water solutions of bases, water solutions of organic compounds, water solutions of inorganic compounds, liquid organic compounds, liquid inorganic compounds, solvents, mineral oils, organic oils, turpentine, olive oil, palm oil, mineral extracts, organic extracts, extracts containing organic compounds, extracts of inorganic compounds, slurries, suspensions, slurries comprising solid phases including inorganic oxides, hydroxides, salts, organometallic complexes, nano-dispersed solids, micro-dispersed solids, carbon-based clusters, and fine particles, and supercritical liquids.

6. The method of claim 1 further comprising the steps of moisture adjusting the porous carbonaceous material by at least partially drying the porous carbonaceous material.

7. The method of claim 6 where the step of moisture adjusting the porous carbonaceous material is performed by pulling a vacuum on the tank, applying positive pressure on the content of the tank, heating the content of the tank, applying centrifugal force and/or creating a pressure gradient in the tank to remove excess liquid.

8. The method of claim 6 further comprising the step of inoculating the pores of the porous carbonaceous material with an additive.

9. The method of claim 8 where the porous carbonaceous material is inoculated by placing the porous carbonaceous material in a tank; adding inoculate solution to the tank; and impregnating at least a portion of the pore volume of the pores of the porous carbonaceous material with an infiltrate.

10. The method of claim 9 where the step of impregnating at least a portion of the pore volume of the pores of the porous carbonaceous material with an infiltrate includes forcing the infiltrate into the pores of the porous carbonaceous material by changing the pressure in the tank, using a surfactant or both.

11. A method for treating a porous carbonaceous material having pores, the method comprising the steps of:
placing the porous carbonaceous material in a tank;
adding a solution to the tank, where the solution contains a *yucca* extract; and
mixing the solution with the porous carbonaceous material.

12. The method of claim 11 where the solution is a liquid solution containing 0.1-20% of the *yucca* extract.

13. The method of claim 11 where the solution further includes an additive.

14. The method of claim 13 where the additive is selected from the group consisting of water, liquid inorganic and organic compounds of different composition and polarity, water solutions of salts, water solutions of acids, water solutions of bases, water solutions of organic compounds, water solutions of inorganic compounds, liquid organic compounds, liquid inorganic compounds, solvents, mineral oils, organic oils, turpentine, olive oil, palm oil, mineral extracts, organic extracts, extracts containing organic compounds, extracts of inorganic compounds, slurries, suspensions, slurries comprising solid phases including inorganic oxides, hydroxides, salts, organometallic complexes, nano-dispersed solids, micro-dispersed solids, carbon-based clusters, and fine particles, and supercritical liquids.

15. The method of claim 11 where the porous carbonaceous material is made of particles having a diameter greater than 0.037 mm.

16. The method of claim 11 further comprising the steps of moisture adjusting the porous carbonaceous material by at least partially drying the porous carbonaceous material.

17. The method of claim 11 further comprising the step of changing the pressure in the tank.

* * * * *